United States Patent
Gosney et al.

(10) Patent No.: US 11,872,333 B1
(45) Date of Patent: Jan. 16, 2024

(54) CASSETTE APPARATUS UTILIZING VENTING FOR PROCESSING OF BLOOD TO REMOVE PATHOGEN CELLS THEREIN

(71) Applicants: William M. Gosney, Lucas, TX (US); Dale B. Nixon, Dallas, TX (US)

(72) Inventors: William M. Gosney, Lucas, TX (US); Dale B. Nixon, Dallas, TX (US)

( * ) Notice: Subject to any disclaimer, the term of this patent is extended or adjusted under 35 U.S.C. 154(b) by 3 days.

(21) Appl. No.: 17/814,549

(22) Filed: Jul. 25, 2022

(51) Int. Cl.
| | |
|---|---|
| *A61M 1/36* | (2006.01) |
| *A61M 60/36* | (2021.01) |
| *A61M 60/279* | (2021.01) |
| *A61M 60/113* | (2021.01) |
| *A61M 1/14* | (2006.01) |

(52) U.S. Cl.
CPC ........ *A61M 1/1562* (2022.05); *A61M 1/3672* (2013.01); *A61M 1/36226* (2022.05); *A61M 60/113* (2021.01); *A61M 60/279* (2021.01); *A61M 60/36* (2021.01)

(58) Field of Classification Search
CPC .............. A61M 1/156; A61M 1/36226; A61M 1/1562; A61M 1/1565; A61M 1/362265; A61M 1/3622
See application file for complete search history.

(56) References Cited

U.S. PATENT DOCUMENTS

| | | | |
|---|---|---|---|
| 4,786,812 A | 11/1988 | Humphreys | |
| 6,127,507 A | 10/2000 | Santerre | |
| 6,746,613 B2 | 6/2004 | Korenev | |
| 6,872,198 B1 | 3/2005 | Wilson et al. | |
| 6,998,076 B2 | 2/2006 | Ohshiro | |
| 7,112,916 B2 | 9/2006 | Goh et al. | |
| 7,229,427 B2 | 6/2007 | Mallett | |
| 7,346,205 B2 | 3/2008 | Walker, Jr. | |
| 7,758,208 B2 | 7/2010 | Bailey | |
| 7,837,897 B2 | 11/2010 | Zhang et al. | |
| 7,889,154 B2 | 2/2011 | Araki et al. | |
| 8,242,832 B2 | 8/2012 | Ochi et al. | |
| 8,258,899 B2 | 9/2012 | Feng et al. | |
| 8,624,968 B1 | 1/2014 | Hersee et al. | |
| 9,141,885 B2 | 9/2015 | Yang et al. | |
| 9,387,286 B2 | 7/2016 | Kelly et al. | |
| 9,420,209 B2 | 8/2016 | Ahn et al. | |
| 2002/0076744 A1 | 6/2002 | Koller | |
| 2003/0153825 A1 | 8/2003 | Mooradian | |
| 2011/0021966 A1 | 1/2011 | Eonard | |
| 2016/0041094 A1 | 6/2016 | Lei | |
| 2016/0171686 A1 | 6/2016 | Du | |
| 2017/0049889 A1 | 2/2017 | Felder et al. | |
| 2020/0179929 A1 | 6/2020 | Sherman | |

(Continued)

*Primary Examiner* — Leslie R Deak

(57) ABSTRACT

An apparatus for locating and venting pathogen cells in blood. A cassette has a plurality of thin holding chambers that are filled with blood drawn from a patient. A light source illuminates each of the holding chambers and passes light to an underlying sensor array such that the cells in the blood produce shadow images of the cells in the sensor array. A processor performs pattern recognition to identify and locate the pathogen cells by use of an image library. After the pathogen cells are located, a pump is operated to move the identified cells to a processing zone. When each identified cell reaches the processing zone, a control voltage is generated to open a valve to vent the identified pathogen cells. The pump refills the cassette holding chambers, returns the processed blood to the patient, and the procedure is repeated for a treatment time period.

20 Claims, 41 Drawing Sheets

(56) References Cited

U.S. PATENT DOCUMENTS

2020/0305783 A1 10/2020 Baker
2021/0333211 A1 10/2021 Chen
2022/0012456 A1 1/2022 Knowles

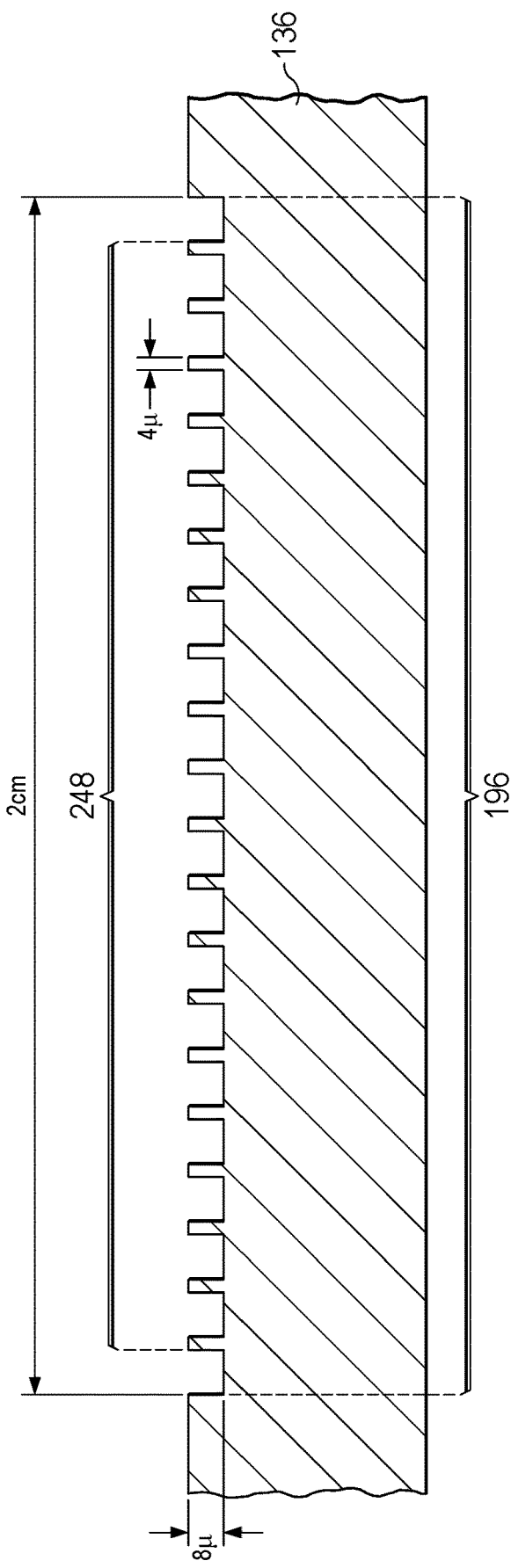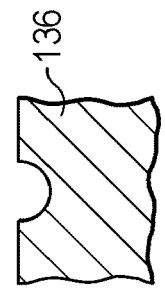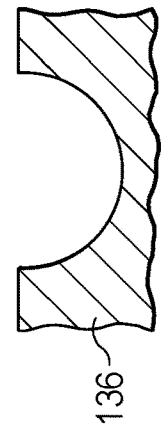
FIG. 10
FIG. 12
FIG. 11

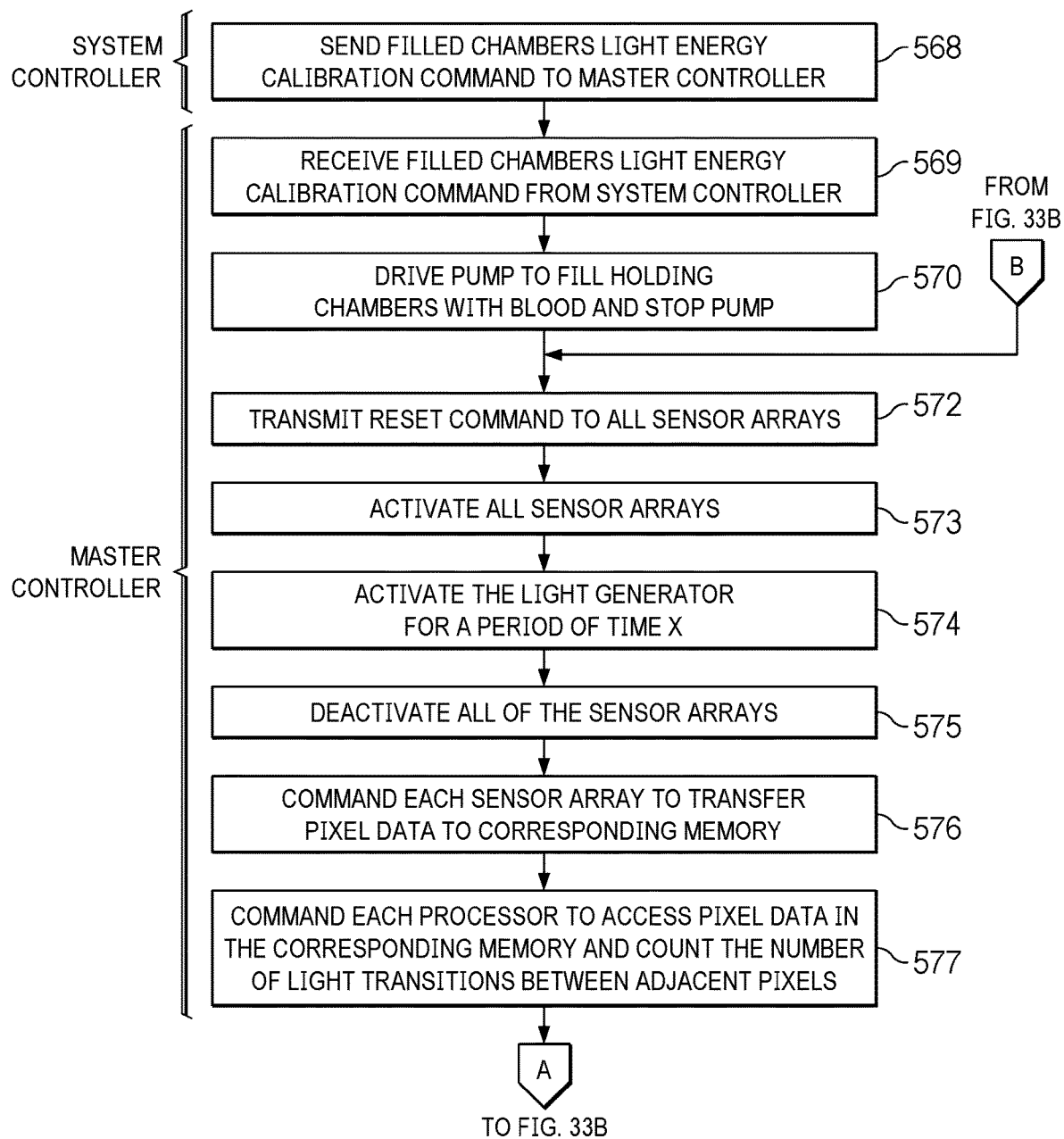

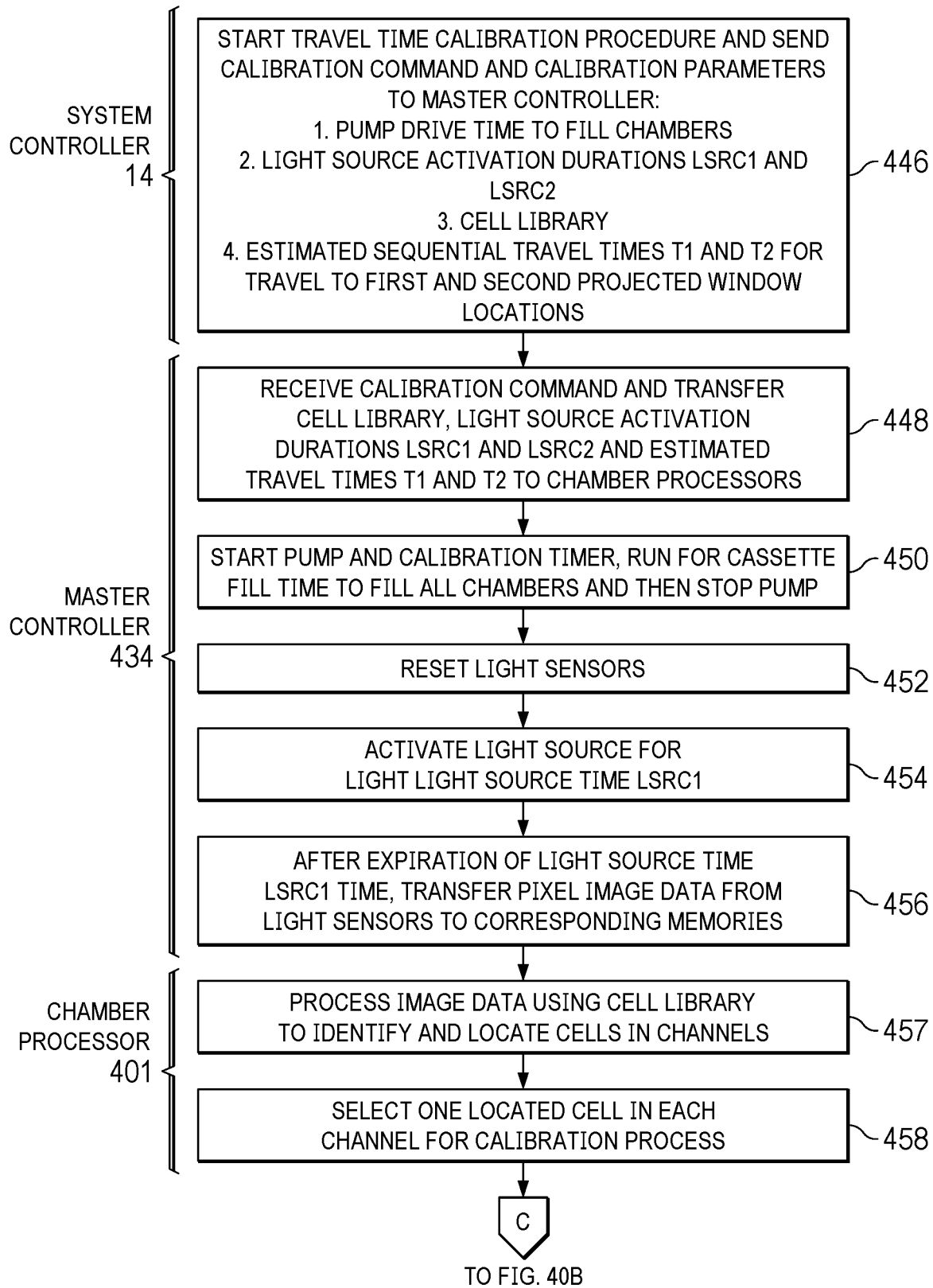

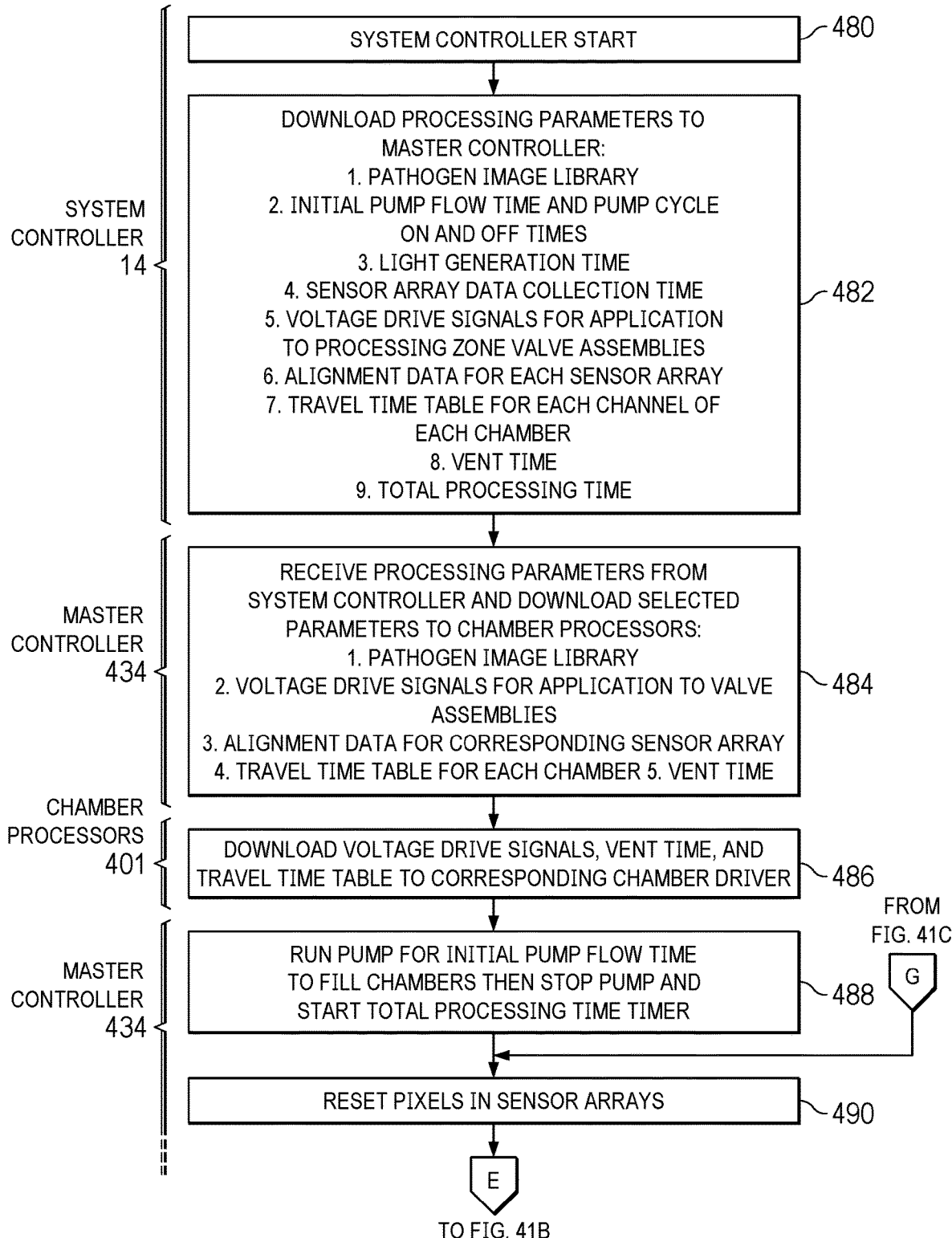

CASSETTE APPARATUS UTILIZING VENTING FOR PROCESSING OF BLOOD TO REMOVE PATHOGEN CELLS THEREIN

CROSS REFERENCE TO RELATED APPLICATIONS

Applicants have concurrently filed additional applications related to the subject matter of the present application. These are: Ser. No. 17/814,536 filed Jul. 25, 2022; Ser. No. 17/814,537 filed Jul. 25, 2022; Ser. No. 17/814,538 filed Jul. 25, 2022; Ser. No. 17/814,539 filed Jul. 25, 2022; Ser. No. 17/814,541 filed Jul. 25, 2022; Ser. No. 17/814,542 filed Jul. 25, 2022; Ser. No. 17/814,543 filed Jul. 25, 2022; Ser. No. 17/814,545 filed Jul. 25, 2022; Ser. No. 17/814,546 filed Jul. 25, 2022; Ser. No. 17/814,547 filed Jul. 25, 2022; and Ser. No. 17/814,548 filed Jul. 25, 2022.

BACKGROUND

Field of the Invention

The present invention is in the field of biotechnology, semiconductor technology and the medical field of treating individuals who have an infection of pathogen cells in the bloodstream.

Description of the Related Art

The presence of bacteria in human blood is a serious condition termed "bacteremia". This condition can cause an infection that spreads through the bloodstream. This can also be termed "septicemia" which is defined as the invasion and persistence of pathogenic bacteria in the bloodstream. Such an infection can lead to a condition termed "sepsis" which is the body's reaction to the infection. Sepsis is a serious condition that can cause intense sickness including shock, and in some cases, can lead to the death of the infected person. A common pathogenic bacterium causing such infection is *E. coli.*, but infections can also be caused by other pathogenic bacteria and organisms such as the fungus *Candida auris*. The usual treatment for the patient is the application of antibiotics to try to kill the pathogenic cells in the bloodstream. However, this treatment is not successful for many patients with a bloodstream infection.

BRIEF DESCRIPTION OF THE DRAWINGS

For a more complete understanding of the present invention and the advantages thereof, reference is now made to the following description taken in conjunction with the accompanying drawings in which:

FIG. 10 is a section view along line 10-10 in FIG. 9, FIG. 11 is a section view along line 11-11 in FIG. 9, FIG. 12 is a is a section view along line 12-12 of FIG. 9, FIGS. 33A and 33B are a flow diagram illustrating a light source amplitude calibration process, FIGS. 40A, 40B and 40C are a logic flow diagram illustrating a travel time calibration process.

SUMMARY OF THE INVENTION

An embodiment of the present invention comprises an apparatus for first examining blood by imaging a first quantity of blood in a chamber to identify and locate pathogen cells in this quantity of blood. The pathogen cells thus identified are moved to a processing zone of the chamber and are then vented through a valve and transferred to a sump. The first quantity of blood, now processed, is then replaced with multiple subsequent quantities of blood and the process of identifying, locating, moving and venting pathogen cells is repeated for each quantity of blood. After these processing operations are performed repeatedly over a period of time, the count of pathogen cells in the patient blood is decreased.

DETAILED DESCRIPTION OF THE INVENTION

The present invention is an apparatus for identifying pathogen cells in blood and venting the identified cells to reduce the count of such cells in the blood and thereby potentially reducing the harmful effect of the pathogen cells.

Figure 1:
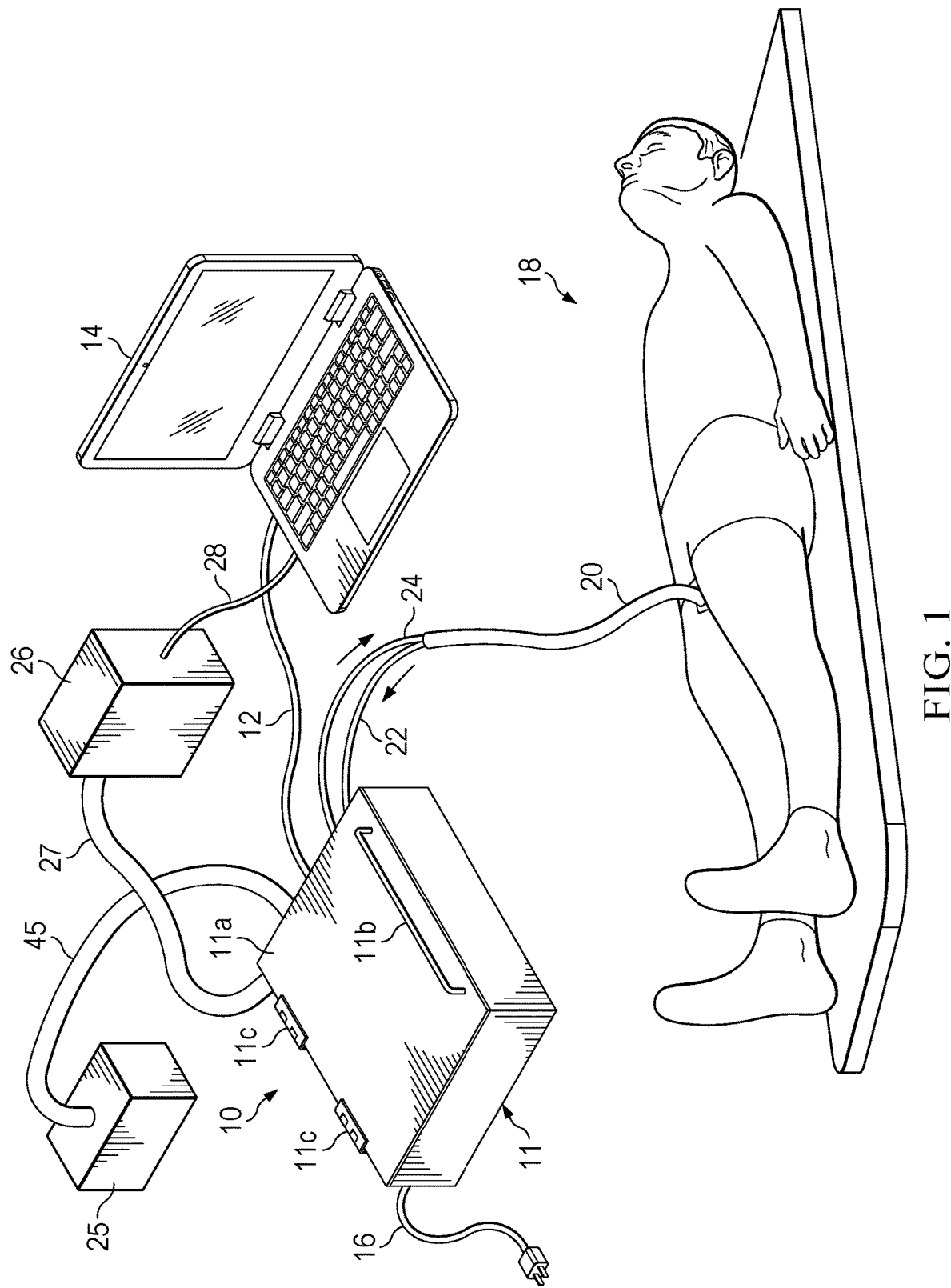
FIG. 1 is a perspective view of an overall system which includes an operational unit and a system control unit.

Referring now to FIG. 1, there is shown a system for processing blood which identifies and determines locations of individual pathogen cells in blood and then venting the identified cells to a sump.

The principal operations performed with the blood are carried out in an operational unit 10 which is connected by a data and control cable 12 to a system controller 14 which can be, for example, a laptop computer or computer work station. The operational unit 10 receives electrical power via a power line 16.

The operational unit 10 is connected to a patient 18 by means of a two-lumen (two fluid channels) catheter 20. The patient 18 can be reclined on a horizontal surface. In this example, the catheter 20 is inserted into an artery in the leg of patient 18 to both receive blood from the patient and return blood to the patient. The catheter 20 has one lumen thereof connected to a blood input line 22 which is connected to operational unit 10 and has a second lumen connected to a blood return line 24 which is also connected to the operational unit 10. The blood of patient 18 flows into the catheter 20, through input line 22 to the operational unit 10 and from the operational unit 10 through the return line 24 and catheter 20 back to the patient 18. A catheter, such as 20, is described in U.S. Pat. No. 6,872,198 issued Mar. 25, 2005 which patent is incorporated herein by reference in its entirety.

Within the operational unit 10 the blood is imaged to identify and locate pathogenic cells in the blood followed by venting the located pathogenic cells to a sump outside of the unit 10. This process continues over a period of time with a flow of blood from the patient for the purpose of reducing the number of pathogenic cells in the patient's blood.

The operational unit 10 includes an enclosure 11 having a top lid 11a which can be opened by use of a handle 11b which rotates the lid 11a on hinges 11c.

Further referring to FIG. 1, there is included a sump 25 that is coupled via a drain line 45 to the interior of the unit 10. The sump 25 receives blood fluid that has been vented from the blood flow in the operational unit 10. The system shown in FIG. 1 further includes a heater/cooler thermal control 26 which provides temperature-controlled air through a duct 27 to within the enclosure 11.

Figure 2:
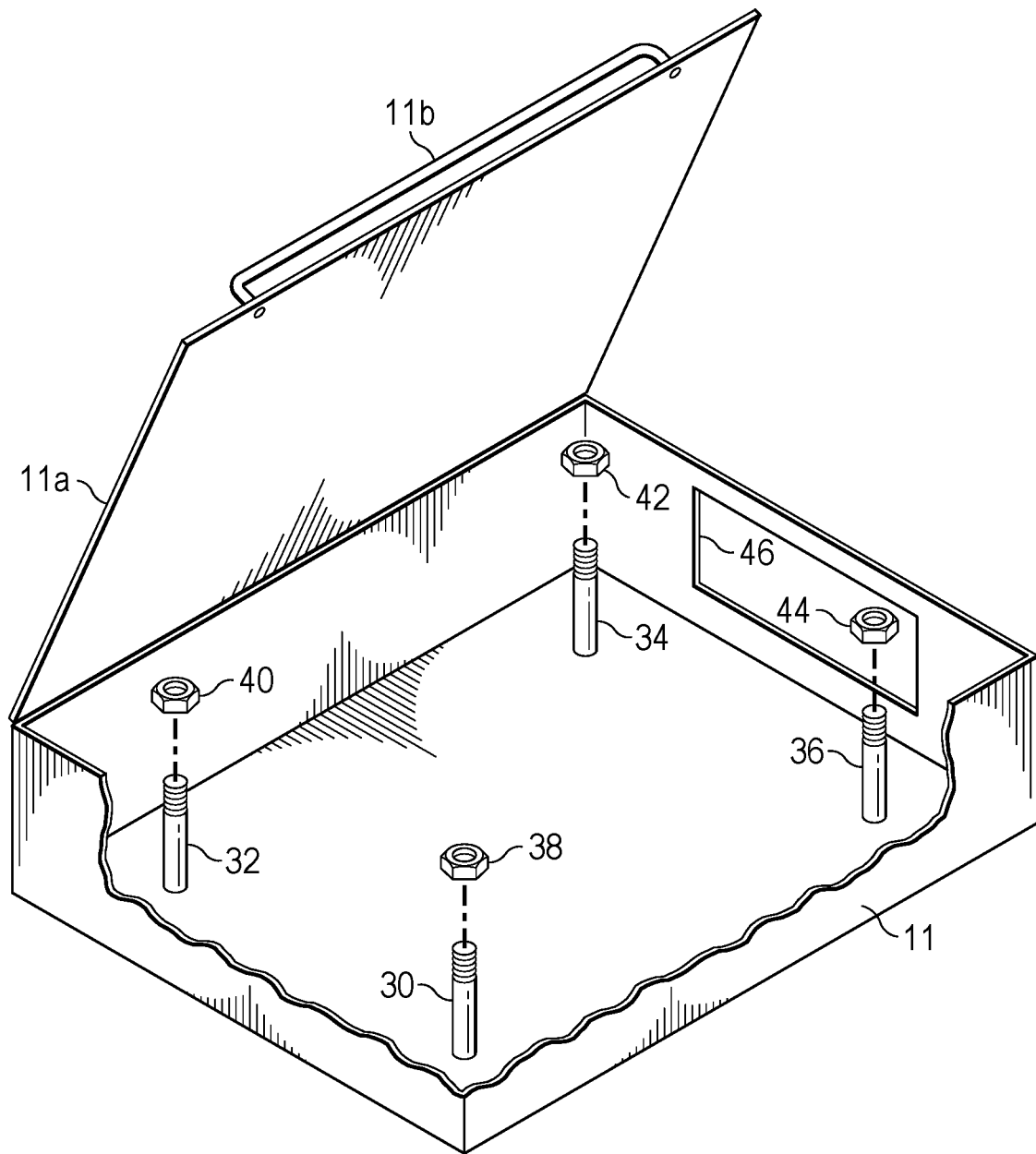
FIG. 2 is a perspective view showing the interior of the enclosure 11 shown in FIG. 1.

The interior of the enclosure 11, shown in FIG. 1, is illustrated in FIG. 2 without operational components. A set of four rods 30, 32, 34 and 36 are mounted on the interior bottom surface of the enclosure 11. These rods project upward, perpendicular to the bottom surface of the enclosure 11. The top end of each of the rods 30, 32, 34 and 36 are threaded to receive respective nuts 38, 40, 42 and 44. The nuts 38, 40, 42 and 44, when mounted on the corresponding rods, engage the top surface of a compression plate 51 shown in FIGS. 3 and 4. The enclosure 11 can include a thermostat and be connected to an air heater/cooler thermal control unit 25 (see FIG. 1 and FIG. 8) to maintain the interior of the enclosure 11 within a selected temperature range to avoid thermal damage to the blood in the enclosure 11. The enclosure 11 has an opening 46 for passage therethrough of flow tubes and electrical conductors.

Figure 3:
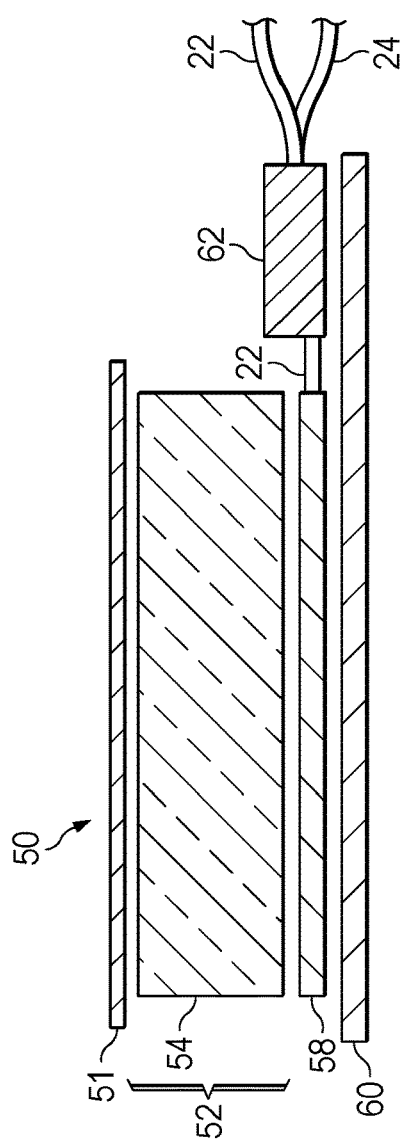
FIG. 3 is an elevation, section view of components inside the operational unit shown in FIG. 1.

An embodiment of the present invention is shown in FIG. 1, and described in the corresponding text, with specific internal components 50 of an operational unit 10 as shown in FIG. 3. The operational unit 10 has multiple components 50 inside the enclosure 11. These components include the compression plate 51 and a light source 54. The unit 50 further includes a cassette 58 and an imager and processor unit 60. Line 22 extends through a pump 62 to the input of the cassette 58. Pump 62 draws blood from patient 18 through input line 22 into the operational unit 10 and the blood leaves unit 10 through return line 24 and through catheter 20 back to patient 18. The components 54, 58 and 60 have planar configurations and, in operation, are pressed together with limited spacing between them and secured by the nuts 38, 40, 42 and 44 to limit relative movement. The return line 24 is connected to the output port of cassette 58 and does not pass through the pump 62.

Figure 4:
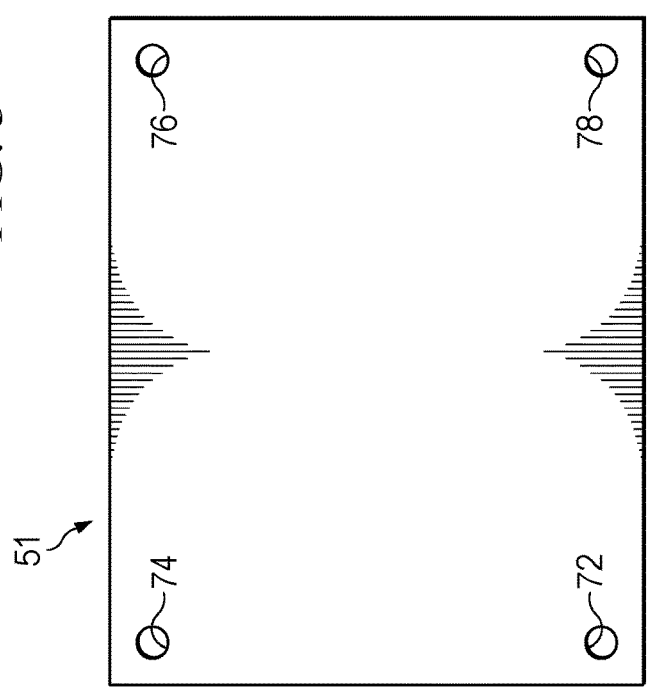
FIG. 4 is a plan view of the compression plate 51 shown in FIG. 3.

The compression plate 51 is shown in FIG. 4. Plate 51 includes holes 72, 74, 76 and 78 which are positioned to receive the respective rods 30, 32, 34 and 36, see FIG. 2. All of the elements 51, 54, 58 and 60 are provided with colinear holes for receiving the rods 30, 32, 34 and 36. When the nuts 38, 40, 42 and 44 are affixed to the rods 30, 32, 34 and 36, with all of the noted components 50 (see FIG. 3) in place and having the rods 30, 32, 34 and 36 passing therethrough, the nuts are tightened on the rods to cause the compression plate 51 to apply force to the stacked elements 51, 54, 58 and 60 to clamp them together and substantially limit relative movement, either horizontally or vertically, between these components.

Figure 5:
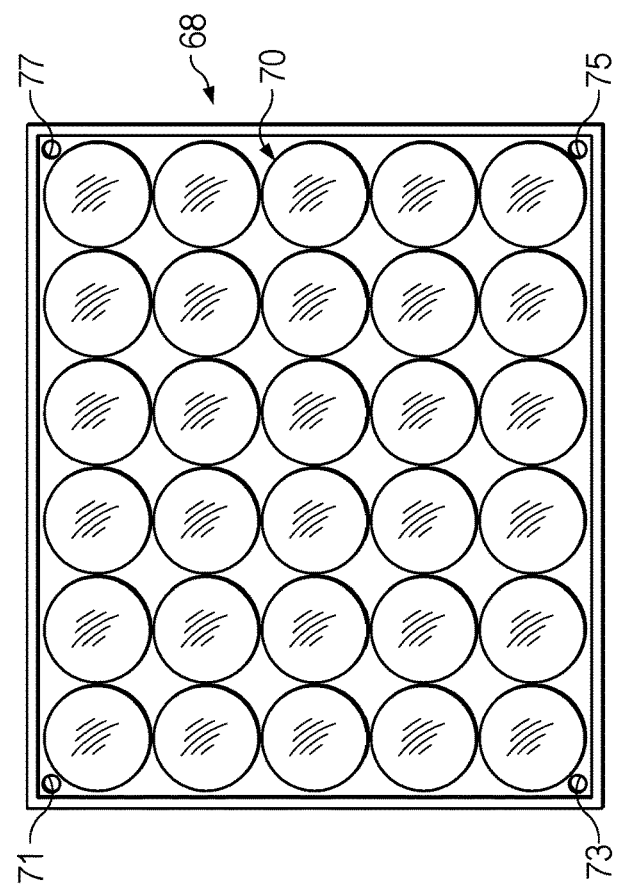
FIG. 5 is a bottom view of the light source shown in FIG. 3 with an array of light generators.

A planar, bottom view of the light source 54 is shown in FIG. 5. Source 54 includes a 5×6 array 68 of light generators, which includes a light generator 70 which is representative of all of the light generators in the array 68. Each of the light generators, including 70, produces a collimated beam of light directed perpendicular to the cassette 58. The light generator 70 is further shown in an elevation view in FIG. 6. Light source 54 includes holes 71, 73, 75 and 77 for receiving the rods 30, 32, 34 and 36.

Collimated light sources are well known in the art. Multiple embodiments of collimated light source generators are usable with the present invention. A collimated light generator is described in U.S. Pat. No. 7,758,208 filed Dec. 26, 2007 which patent is incorporated herein by reference in its entirety.

Figure 6:
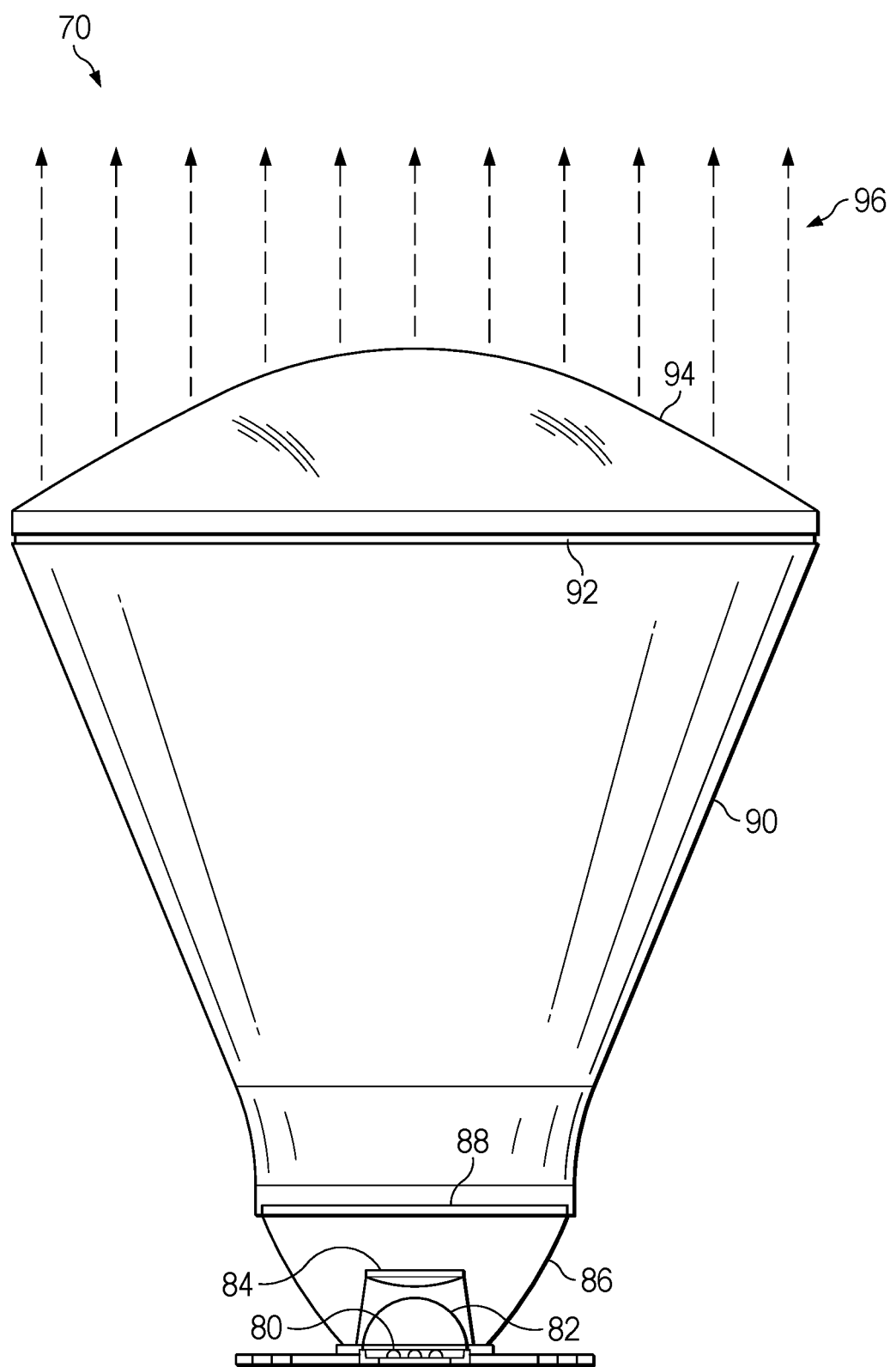
FIG. 6 is an elevation, sectional view of a collimated beam light generator, as shown in FIG. 5.

Referring to FIG. 6, the light generator 70 includes a light engine 80, an extraction lens 82, a collimator lens 84, a collimator lens 86, a lenslet array 88, a profile reflector 90, a secondary lenslet array 92 and a secondary collimator lens 94. The light generator 70 produces a collimated beam of light 96.

Figure 7:
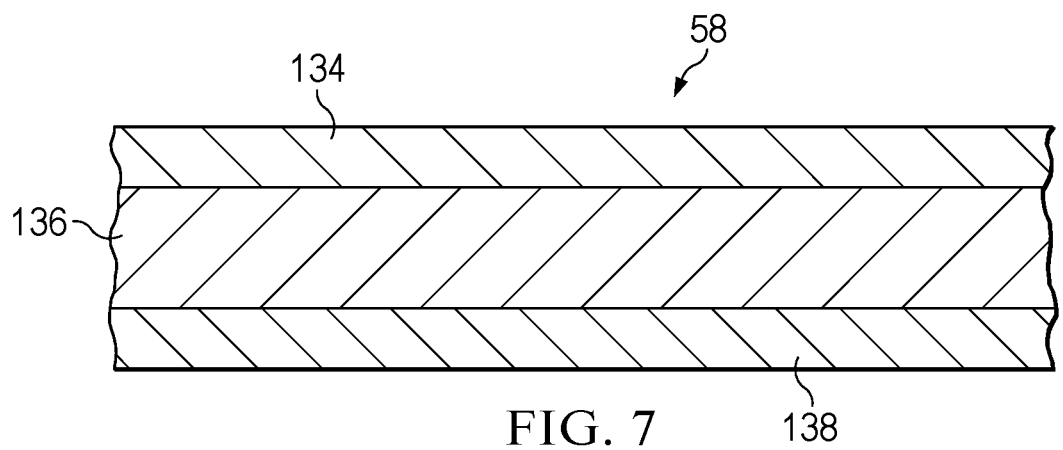
FIG. 7 is an elevation section view of the cassette 58 shown in FIG. 3.

The cassette 58 is shown in an elevation section view in FIG. 7. Cassette 58 comprises a top layer 134, a middle layer 136 and a bottom layer 138. After fabrication as separate layers, the layers 134, 136 and 138 are bonded together to form the cassette 58. All of these layers are made of a transparent, non-electrical-conducting material, such as a polymer plastic.

Figure 8:
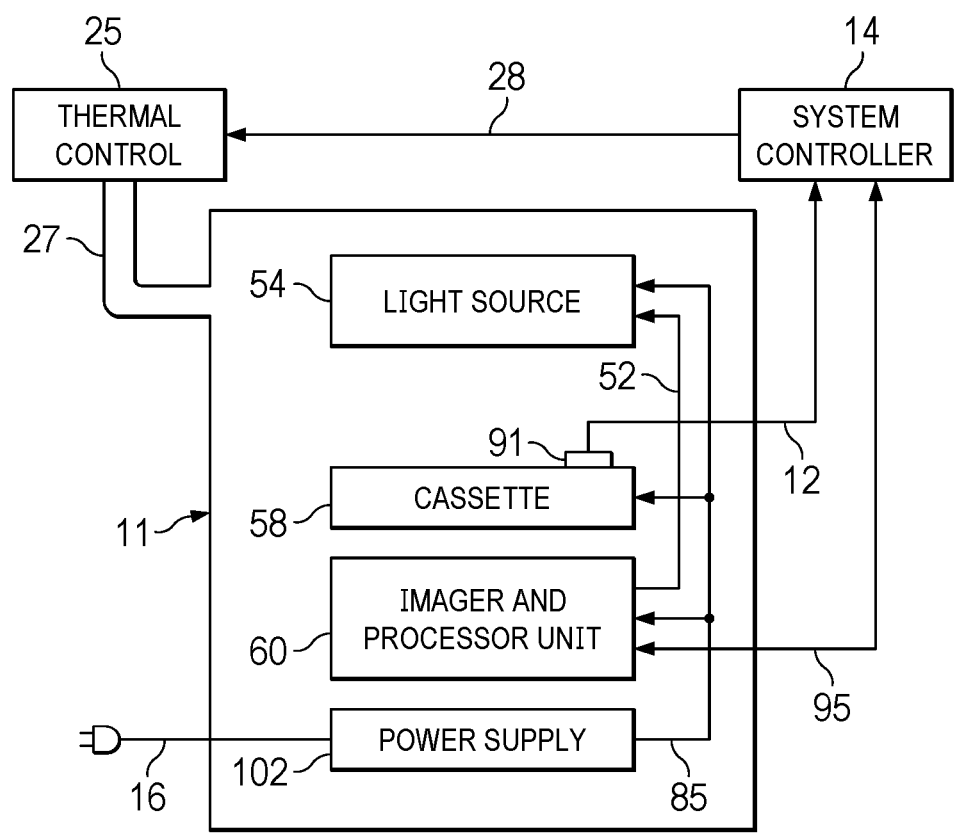
FIG. 8 is a functional block diagram including additional components for the system shown in FIG. 1.

The operational unit 10, shown in FIG. 1, is further shown in FIG. 8 with additional operational components. On the interior of enclosure 11 there is the light source 54, cassette 58, and imager and processor unit 60. Further included is a power supply 102 which receives power from line 16 and provides power via power cable 85 to the processor unit 60, the light source 54 and the cassette 58. A temperature sensor 91 is mounted on the cassette 58 to measure the temperature of the cassette 58. The temperature sensor 91 is connected to the system controller 14 via a cable 95 to provide a temperature measurement of the cassette 58 to the controller 14. A thermal control 25 is coupled by cable 28 to the controller 14. Cable 28 can be included with cable 12. The controller 14 measures the temperature of the cassette 58 by the temperature sensor 91 and activates the thermal control unit 26 to provide warmer air or cooler air to within the enclosure 11 via a duct 27 to drive the temperature of the cassette 58 to a selected temperature, for example, typical human body temperature.

The above embodiment in FIG. 8 has a power line that is directly connected to the cassette 58. An alternative configuration has a light power transmitter on the unit 60 for each chamber of the cassette 58. In this alternative configuration there is adjacent to each chamber of the cassette 58 a light power receiver that receives the light power beam from the underlying transmitter and converts the light power to electrical power that is provided to a chamber driver 318 shown in FIG. 21. By use of the light power transmission, there is no requirement to have any power electrical connection to the cassette 58. The unit 60 controls the light source 54 via a line 52.

Figure 9:
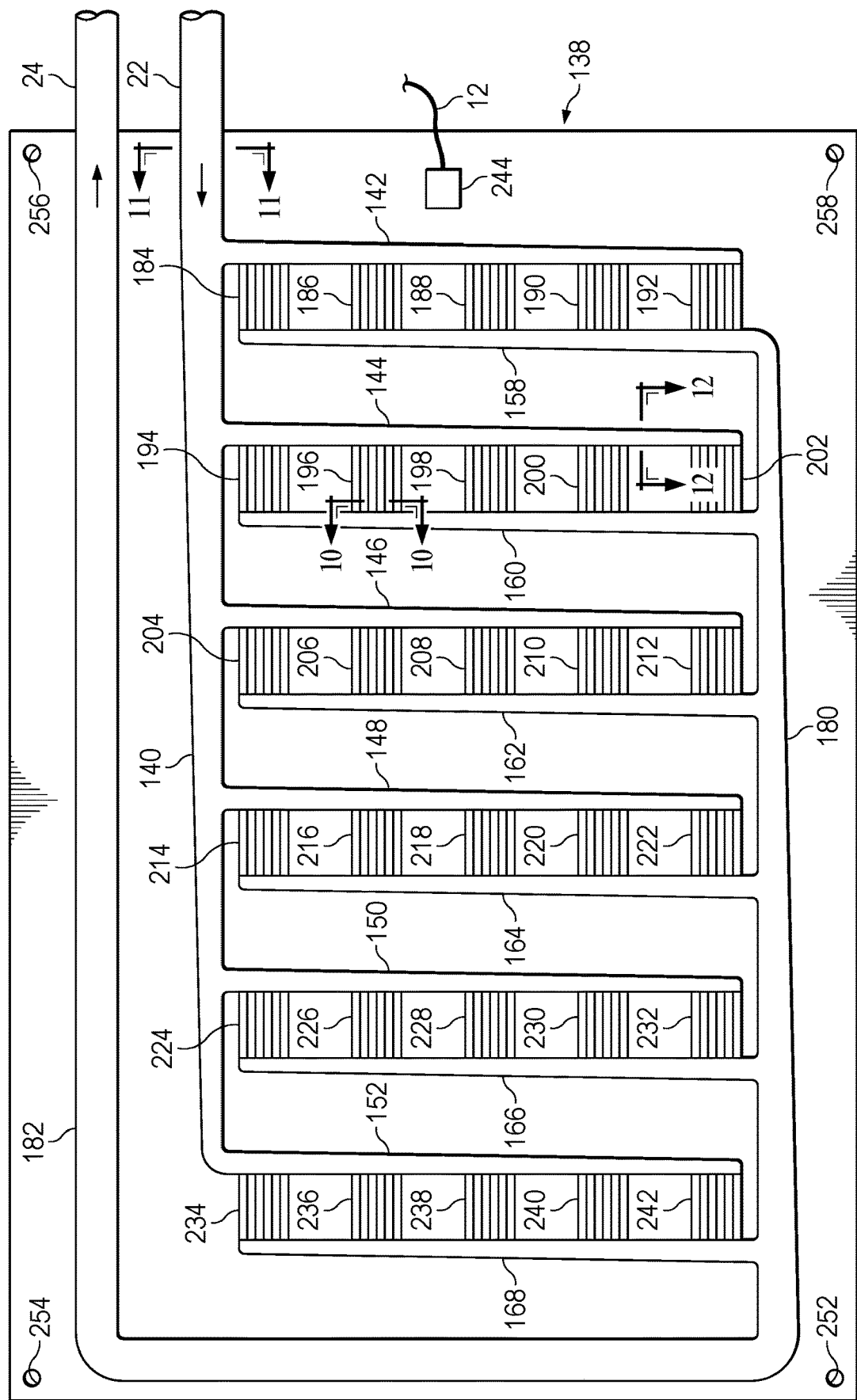
FIG. 9 is a bottom view of the primary blood flow through the cassette 58 shown in FIG. 3.

The cassette 58 has an array of holding chambers. One embodiment of the cassette 58 has an array of 30 holding chambers, as shown in FIG. 9. This is a top-down view of layer 136. The chambers and flow lines shown are molded into the bottom region of layer 136. The cassette 58, as shown in FIG. 9 for an embodiment of the invention, has 30 holding chambers 184, 186, 188, 190, 192, 194, 196, 198, 200, 202, 204, 206, 208, 210, 212, 214, 216, 218, 220, 222, 224, 226, 228, 230, 232, 234, 236, 238, 240 and 242. The cassette 58 input manifold comprises distribution line 140 and chamber input lines 142, 144, 146, 148, 150 and 152. The output manifold comprises chamber output lines 158, 160, 162, 164, 166 and 168, the collection line 180 and the return line 182. This manifold configuration provides approximately the same blood flow path distance from the input of line 140 to the output of line 182 for the blood flowing through each of the holding chambers. This configuration contributes to a more uniform flow of blood through the holding chambers and more uniform fluid flow pressure gradient through the cassette 58. The bottom layer 138 forms a closing surface for all of the chambers and lines in the layer 136. See FIG. 7.

Figure 15:
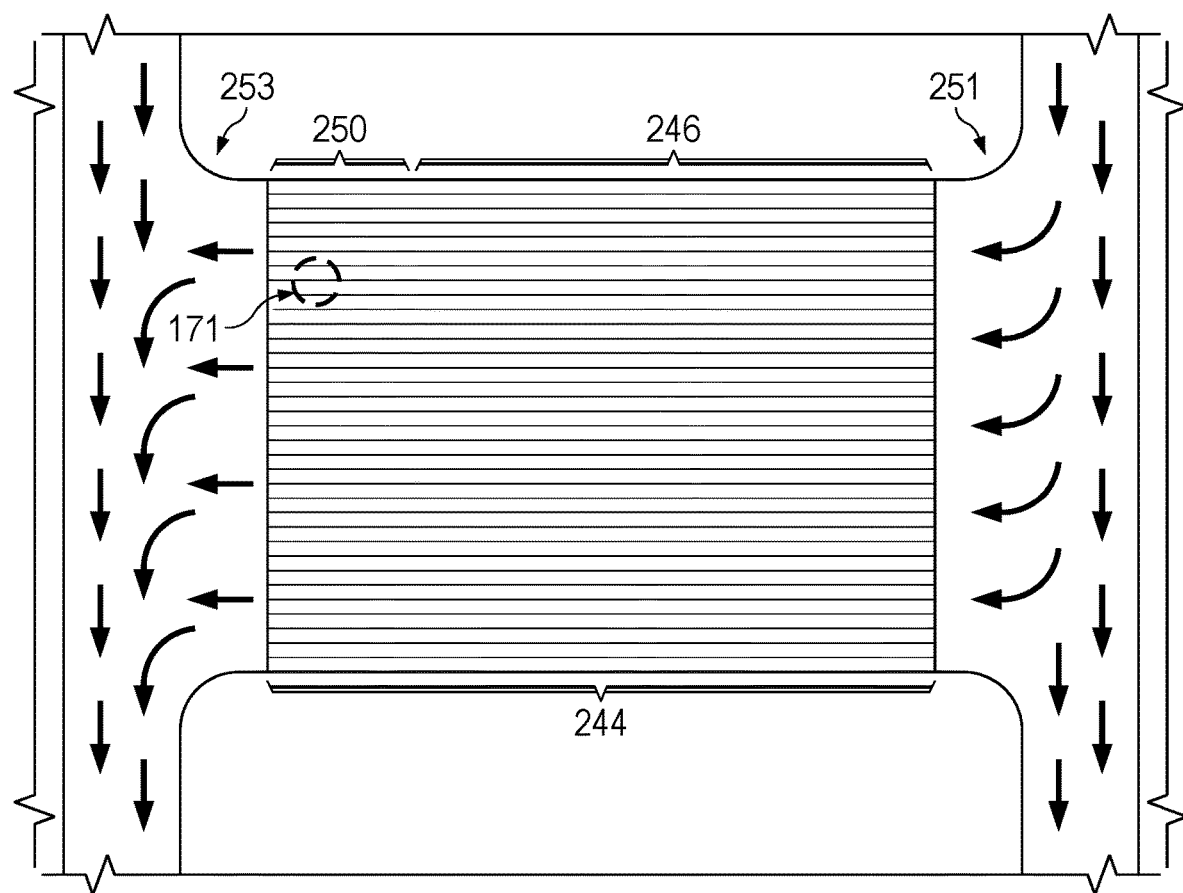
FIG. 15 is a view of a cassette 58 holding chamber having a plurality of parallel ridges therein and multiple zones.

Input line 142 supplies blood to each of the chambers 184, 186, 188, 190, 192. Each chamber in cassette 58 can have, for example, an X dimension of 2 centimeters, a Y dimension of 2 centimeters, and a thickness (Z dimension) in the range of 8-12 microns. An example value is 8 microns. A selected range of thickness is 10 microns or less. The facing area of each chamber is therefore 4 square centimeters. The opening width from the input line 142 into chamber 184 is the same as the Y dimension of the chamber, in this example, 2 centimeters. Likewise, the output from each chamber, such as 184, is the Y dimension, in this example, 2 centimeters. A chamber, as viewed at the input, is relatively wide (2 centimeters) and relatively thin (8 microns). This configuration is the same for all of the remaining holding chambers in cassette 58. Each of the chambers has an input port and an output port. See FIG. 15. Between the input line, such as 142, and the input port to a chamber, such as 184, there is a flow path having the same width and height as the chamber and a length of, for example, 0.1 to 0.4 centimeters. There is a similar flow path at the output port of each chamber. These flow paths can assist in providing a uniform fluid flow through the chamber. These flow paths are shown in FIG. 15 as flow path regions 251 and 253.

Further referring to FIG. 9, the blood fluid leaves the holding chambers 184-242 and moves into the corresponding connected chamber output lines 158-168. The exit passageway from a chamber is the same configuration as the input passageway, that is, for this embodiment, the exit passageway is 2 centimeters wide and 8 microns thick. The blood flows through the output lines 158-168 into the collection line 180 and then into the return line 182.

As a flow example, referring to FIG. 9, blood is driven into distribution line 140 and then into chamber input line 150 and at the far end of this line, into chamber 232. After the blood in this chamber is processed, the blood in chamber 232 is driven out of the chamber by pump 62 into the chamber output line 166 and from the end of line 166 into the collection line 180. From line 180, the blood flows into the return line 182 and then into the blood return line 24. The blood travels through the cassette input manifold to all of the chambers and returns from all of the chambers through the cassette output manifold.

Further referring to FIG. 9, the cassette 58 is provided with alignment holes 252, 254, 256 and 258. The cassette 58 is lowered onto the corresponding upward facing rods 30, 32, 34 and 36 (See FIG. 2), mounted inside the operational unit 10, which pass through corresponding aligned holes in the imager and processor unit 60 (See FIG. 3). The rods pass through the holes in the cassette 58 to provide alignment of the cassette 58 with the imager and processor unit 60. The light source 54 (FIG. 3) has corresponding alignment holes to receive the rods 30, 32, 34 and 36 so that the imager and processor unit 60, cassette 58, and light source 54 are aligned with each other. The top ends of the rods are threaded so that nuts 38, 40, 42 and 44 (See FIG. 2) can be applied to each rod and tightened so that all three of these units are pressed together and held in alignment with each other.

FIG. 9 shows a top, planar view of the middle layer 136 of cassette 58. Each of the holding chambers 184-242 comprises a recessed region into the bottom side of the middle layer 136. Each chamber recess, in one embodiment, is approximately 8 microns thick, 2 centimeters long and 2 centimeters wide. Referring to FIG. 10, each holding chamber includes a plurality of long, thin ridges 248, illustrated as horizontal lines in each chamber in FIG. 9, and shown in detail in FIG. 10, which is a section view along line 10-10 of a representative holding chamber 196 in FIG. 9. The ridges 248 are formed as a part of the middle layer 136. Example dimensions for a holding chamber and the ridges 248 are shown in FIG. 10. The holding chamber 196 is approximately 2 centimeters wide, as shown, and 2 centimeters long, not shown. The ridges 248 extend for the length (2 centimeters) of the holding chamber 196. Each ridge, in one embodiment, is, for example, 8 microns high and 4 microns wide. The height of the ridges matches the thickness of a chamber. In this embodiment, each of the holding chambers 184-242, has a thickness of, for example, 8 microns. In this example, there are 20 of the elongate ridges spaced in parallel across a distance of 2 centimeters. Therefore, the spacing (channels) between the ridges is approximately 950 microns. Each of the ridges 248 serves as a support for the bottom layer 138 (See FIG. 7) which is pressed against the top of the ridges 248 shown in FIG. 10. The ridges 248 also function as spacers to maintain an essentially uniform 8-micron thickness over all of the area of each holding chamber. The ridges 248, in the illustrated configuration, further form 21 flow channels through the chamber. There can be more ridges to make the channels narrower. These channels reduce the lateral flow of blood in a chamber and support a more straight-through fluid flow from the input to the output of each chamber.

FIG. 11 is a section view taken along lines 11-11 in FIG. 9 in the distribution line 140. The distribution line flow channel has a flat-bottom with semi-circular cross section that has been pressed or molded into the middle layer 136. The flat, and sealing, surface of the flow line 140 is provided by the top surface of the bottom layer 138. FIG. 12 is a section view take along lines 12-12 in FIG. 9 located in the input line 144. It is likewise pressed or molded into the middle layer 136 and covered with the bottom layer 138. The cross-sectional area of line 144 at 12-12 is substantially smaller than that of line 140 at 11-11. There is a greater volume of blood flow through line 140 at 11-11 than through line 144 at 12-12.

All of the layers 134, 136 and 138 are fabricated of, for example, transparent polycarbonate plastic, produced by a pressing or molding process such as described in U.S. Pat. No. 6,998,076 issued Feb. 14, 2006 which patent is incorporated herein by reference in its entirety. As an example embodiment, the top layer 134 and middle layer 136 can each be approximately 2-3 millimeters thick, bottom layer 138 can be 1-1.5 millimeters thick for a total cassette 58 thickness of approximately 5-7.5 millimeters.

The middle layer 136 of cassette 58 can be fabricated by the use of polycarbonate injection molding and a metal mold. An etched glass master is used to form the metal stamping mold. To make the glass master, the process starts with a sheet of glass. The sheet of glass, approximately 5 millimeters thick, is sequentially masked with photoresist patterns (as done in the manufacture of semiconductors) and an acid is applied to etch the non-masked portions. The acid removes a portion of the glass, producing a recessed pattern in the glass and forming the distribution lines and holding chambers. The final 8 micron etch can be done by plasma etching to produce more vertical sidewalls on the ridges 248. After removing the last photoresist, the surface of the glass mold is treated with a mold-release component, and then is covered with a layer of nickel or silver using an electrodeless plating method. Sputtering can be used, or a colloidal silver method can be used. Then, nickel is electroplated over the surface to a thickness of perhaps 0.5 cm forming a metal mold. After separating the electroformed nickel mold from the glass master, the metal mold has raised areas corresponding to the distribution lines and holding chambers. This process is similar to the manufacturing process for phonograph records, compact discs and DVDs as shown in U.S. Pat. No. 6,998,076 noted above. Heated polycarbonate injection molding is used with the metal mold to form the recessed flow channels and holding chambers in what will be the top layer of the cassette. The polycarbonate flows around the raised areas in the metal mold. When the metal mold and polycarbonate are cooled, the polycarbonate sheet is removed and it has the configuration for the top layer 13, as shown in FIGS. 9-12.

Alternately, a metal mold can be machined or etched to have the configuration to produce the cassette middle layer 136 by applying a sheet of polycarbonate to the mold, heating both the mold and the sheet and allowing the polycarbonate to flow into the metal mold to produce the desired shape for the cassette 58. Top layer 134 is fabricated as described above for middle layer 136. The bottom layer 138 is a flat sheet of the same plastic material as the other layers.

The cassette 58 can be fabricated of a plastic with an included anti-thrombogenic material to reduce the possible adhering of blood that contacts interior surfaces of the cassette 58. Such a material is described in U.S. Pat. No. 6,127,507 issued on Oct. 3, 2000, which patent is incorporated by reference herein in its entirety.

Figure 13:
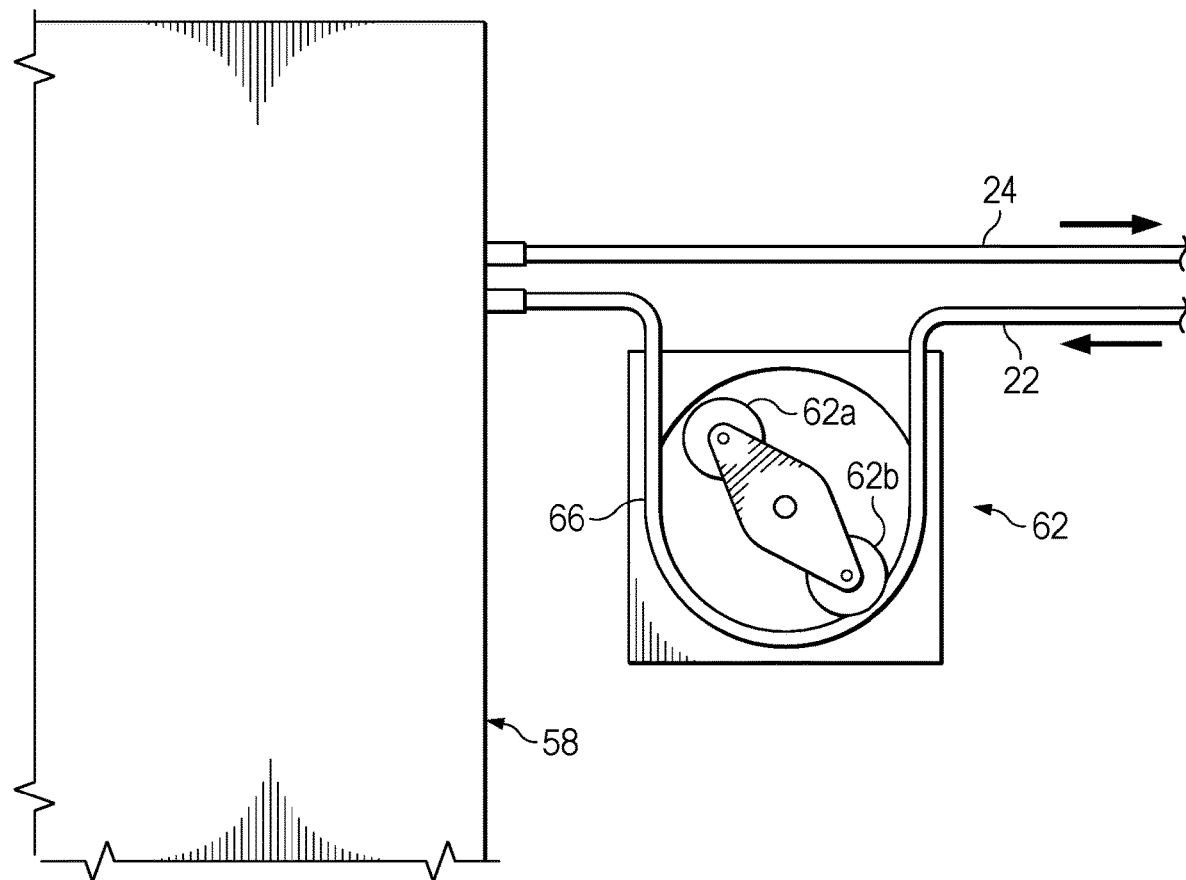
FIG. 13 is a partial cutaway view of cassette 58, pump 62 and flow lines 22 and 24 shown in FIG. 3.

FIG. 13 is an illustration of the cassette 58 together with the peristaltic pump 62 and the blood flow lines. The blood input line 22 is positioned in the pump 62 between pump rollers 62a and 62b and a circular pump pressure plate 66. The rollers rotate about a center shaft and compress the line 22 against the interior curved surface of plate 66. The rollers apply sufficient force to close the flexible line 22 and, as they rotate, they force blood to flow through the line 22 toward the cassette 58. The pump 62 can be started and stopped as needed to pump blood to the cassette 58. After the blood has passed through the cassette 58, it flows through the return line 24 to the catheter 20 and then back to the patient 18. The structure and operation of a peristaltic pump is well known in the art, particularly in the field of kidney dialysis.

Figure 14:
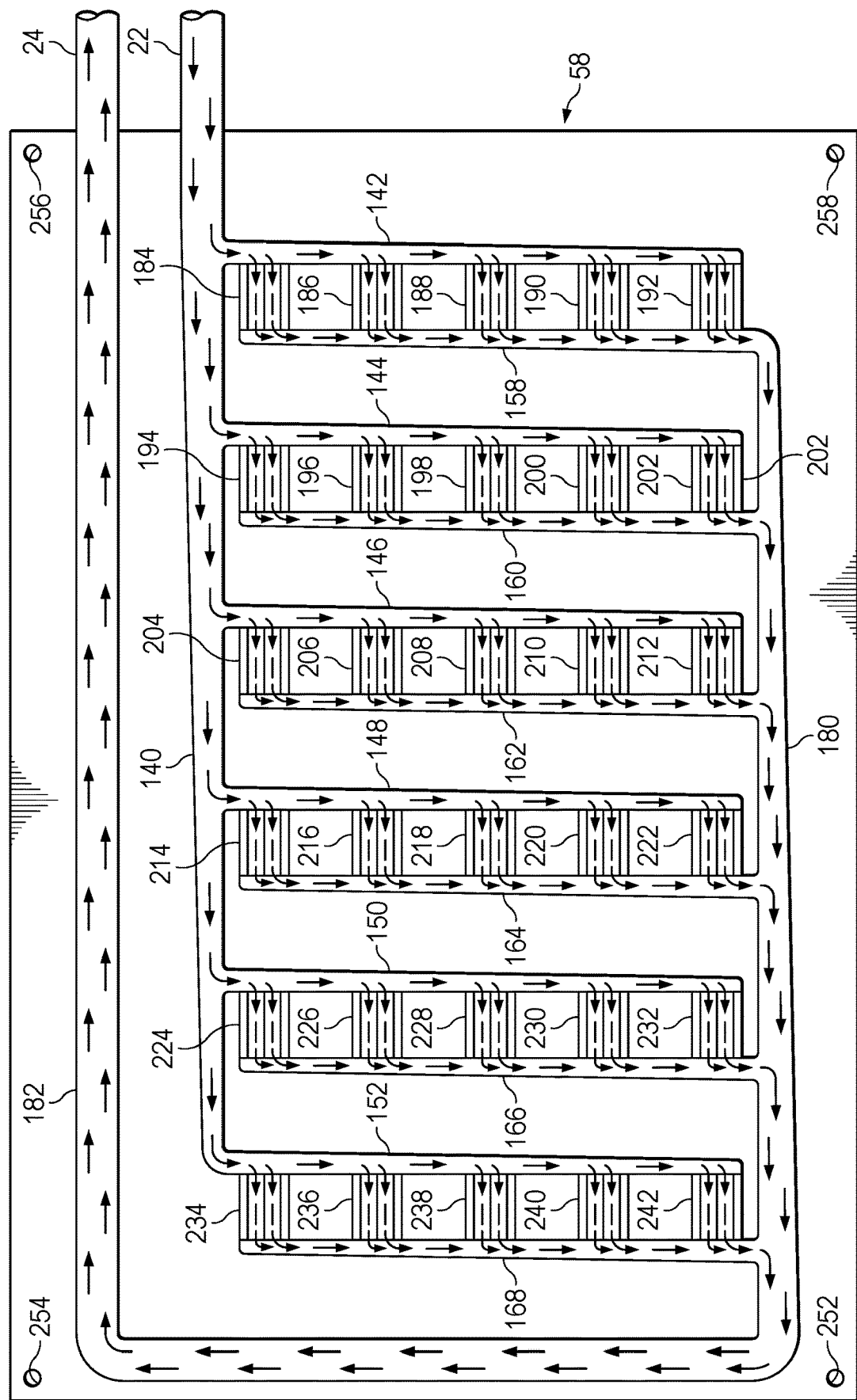
FIG. 14 is a bottom, planar view of the middle layer of the cassette 58, shown in FIG. 3 illustrating the flow of blood through the input manifold channels, holding chambers and output manifold channels.

The flow of blood through the lines and chambers of the cassette 58 is shown in FIG. 14. This is a top view illustrating the bottom of layer 136. Blood enters the input line 22 into distribution line 140 and is sequentially distributed into the chamber input lines 142-152. Note that as the volume of blood flowing through line 140 is decreased, the size of the line 140 is correspondingly decreased. Note that each of the distribution lines 142-152 is tapered so the line size is decreased as the amount of blood flowing in the line decreases. For example, blood flowing in through input line 22 has a portion thereof directed into distribution line 142 and a portion of that flow enters holding chamber 186. As described previously, the chamber 186 is approximately 8 microns high and there are parallel ridges 248 that guide the blood in a uniform flow through the chamber 186. This substantially reduces transverse blood flow in a chamber. At the exit of chamber 186, the blood enters output line 158 where it joins the blood that has passed through chamber 184. The blood from the chambers 184 and 186 flows through output line 158 and is joined sequentially by the blood from chambers 188, 190 and 192. The blood that has flowed through the chambers 184-192 then enters the collection line 180. The blood from all of the holding chambers travels into the collection line 180 from which it flows into the cassette 58 return line 182 to the blood return line 24.

Note in FIG. 14 that the configuration of flow lines and chambers provides approximate the same travel distance for blood flowing through each of the holding chambers 184-242. In each flow path, the blood flows through or beside 10 holding chambers. For example, the blood flow through chamber 206 first passes chambers 184, 194 and 204 then flows through chamber 206 and then passes chambers 208, 210, 212, 222, 232 and 242, for a total distance of 10 chambers. This configuration of chambers and flow lines contributes to uniformity of blood flow and uniformity of pressure gradient reduction for blood flow through the cassette 58.

Referring to FIG. 15, there is shown a chamber 244, which is representative of each of the chambers 184-242 described above. This chamber 244 is formed in the plastic body of the middle layer 136, bottom side, of the cassette 58. (See FIG. 7). The layer 136 has molded ridges which are shown as a group 248 in FIG. 10. The ridges in FIG. 10 are shown as horizontal lines in the chamber. The chamber 244 is subdivided into an identification zone 246 and a processing zone 250. A region 171 of the processing zone 250 is shown in greater detail in FIG. 16. The flow path region 251 functions as an input port to the chamber 244 and the flow path region 253 functions as an output port from the chamber 244.

In operation, blood flows through an input line into the identification zone 246 where it is stopped and an image of this zone is produced by a light source which illuminates the chamber and cell shadow images are detected by a light sensor array on the opposite side. The data from the sensor array is electronically processed by pattern recognition using a reference library of pathogen cell images to locate pathogen cells in the chamber identification zone 246. After the pathogen cells have been located in the channels of the chamber 244, a travel time is taken from a reference database table to specify the travel time for each pathogen cell to a vent line in the processing zone after the pump is started. The pump is started and when each travel time in each channel elapses, a voltage is applied to open a valve in a vent line from the channel in the processing zone to vent the pathogen cell together with a limited amount of surrounding fluid. The blood continues to flow through the processing zone until all of the identified pathogen cells have passed into the processing zone and have been removed by selective venting. The blood flow is then stopped and the process is repeated. Further structure of the processing zone is described below.

Figure 16:
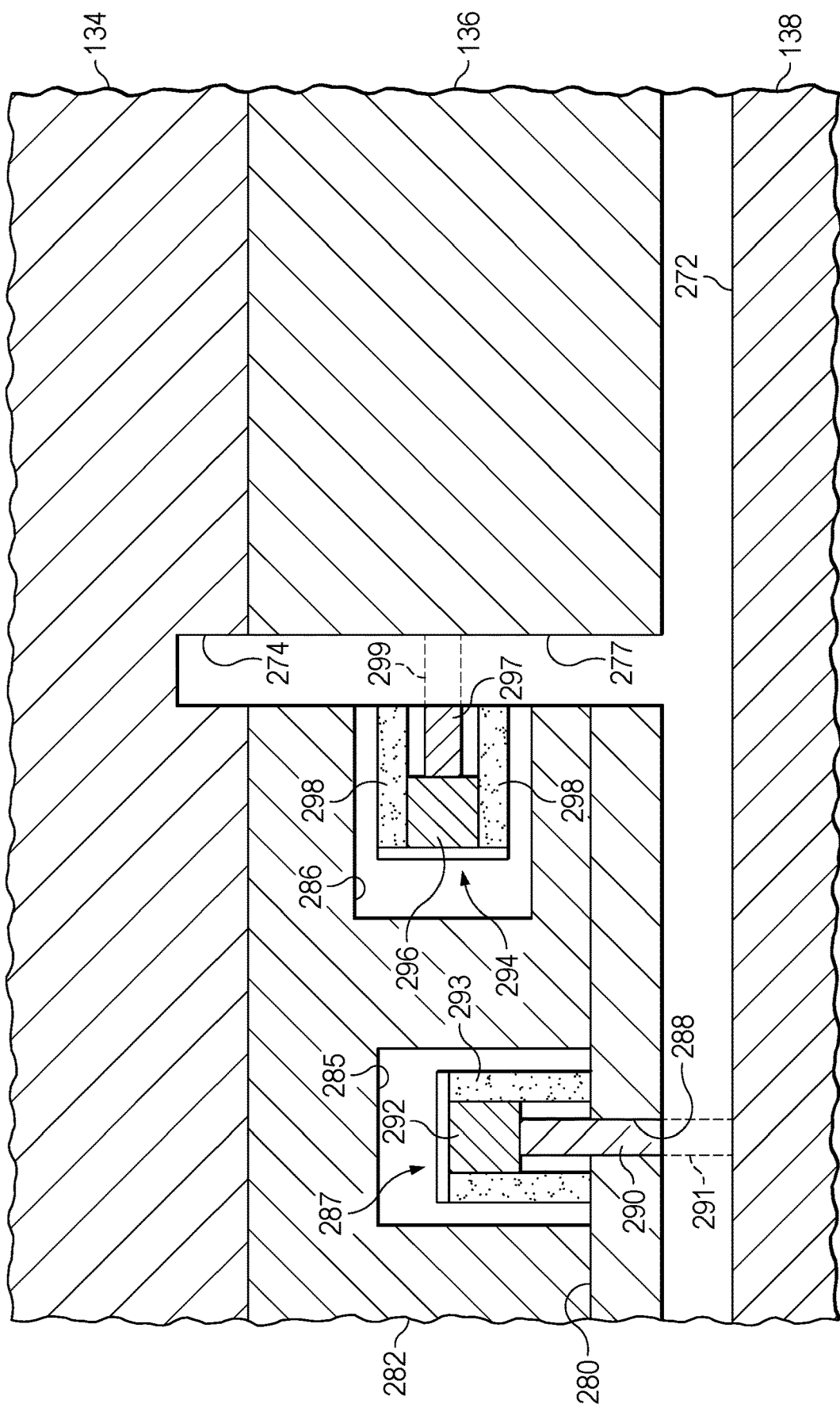
FIG. 16 is a section view of a portion of the cassette chamber shown in FIG. 15 showing a channel valve assembly and a vent line valve assembly.

Referring to FIG. 16, which is a detail view of a region 171 (See FIG. 15) there is shown a section view of the cassette 58. A channel 272 is formed on the bottom surface of layer 136 located between two of the ridges 248 shown in FIG. 10, but not shown in FIG. 16). Fluid flows from right to left in channel 272. A vertical channel vent line 277 in layer 136 extends upward from channel 272 such that fluid can flow from channel 272 into vent line 277. The line 277 opens into a cassette vent line 274 that is molded in the bottom of top layer 134. Further referring to FIG. 16, there is a rectangular molded recess 280 in the upper surface of the layer 136. A valve block 282 is positioned in recess 280. For each channel in the chamber 244 (FIG. 15) there is a vertical channel, such as channel vent line 277 connecting to a corresponding cassette vent line, such as 274, in the upper layer 134. For channel 272 there is a valve assembly 287 in an opening 285 in the valve block 282. Assembly 287 has a moveable element 290 which can be moved through a hole 288 into a region 291 where the element 290 blocks the flow of fluid through channel 272 downstream of the opening into channel vent line 277. The valve assembly 287 has a driver 292 that is coupled to the element 290 for selectively moving the element back and forth between an extended position in region 291 and a retracted position in layer 136 which does not affect fluid flow in channel 272. The assembly 287 has an electric field generator 293 which produces a selectable field that is applied to the driver 292. The driver 292 can be a magnet which is responsive to a first polarity field from generator 293 to drive the element 290 into the region 291 and driver 292, in response to an opposite polarity field from generator 293 retracts the element out of channel 272 into the hole 288. Assembly 287 is a flow channel valve.

Still further referring to FIG. 16, there is an opening 286 in valve block 282 which has a valve assembly 294 in opening 286. The valve assembly 294 has a driver 296 coupled to a moveable element 297. An electric field generator 298 applies a selective electric field to driver 297 to move element 297 into a region 299 or to retract element 297 from region 299. Assembly 294 is a vent valve.

In operation, after blood fluid in channel 272 has been imaged, the pump 62 (FIG. 3) is activated to drive fluid through channel 272 toward valve assemblies 287 and 294. At this time, valve element 290 is retracted and valve element 297 is extended to that no blood fluid flows through channel vent line 277. When a total travel time period for a detected pathogen cell in channel 272 expires, the valve block 282 drives valve assembly 287 to extend element 290 into position 291 to block the flow of fluid and at the same time activates valve assembly 294 to withdraw element 297 from blocking fluid flow through the channel vent line 277. The pump 62 drives a slug of blood fluid from channel 272 into channel vent line 277 until the valve block activates the valve assemblies 287 and 294 to return corresponding elements to the original positions such that the blood fluid flow continues only through channel 272 downstream from channel vent line 277. Thus, a slug of blood fluid, which includes a detected pathogen cell, is vented from the chamber 244 and flows through a vent line into the sump 25 (FIG. 1). There are two valve assemblies, as shown in FIG. 16, for each channel of the chamber 244 and for each chamber in the cassette 58.

The structure shown in FIG. 16 is representative for all of the channels in each of the chambers in the cassette 58. Each chamber can have hundreds or even thousands of channels with the corresponding structures.

Figure 17:
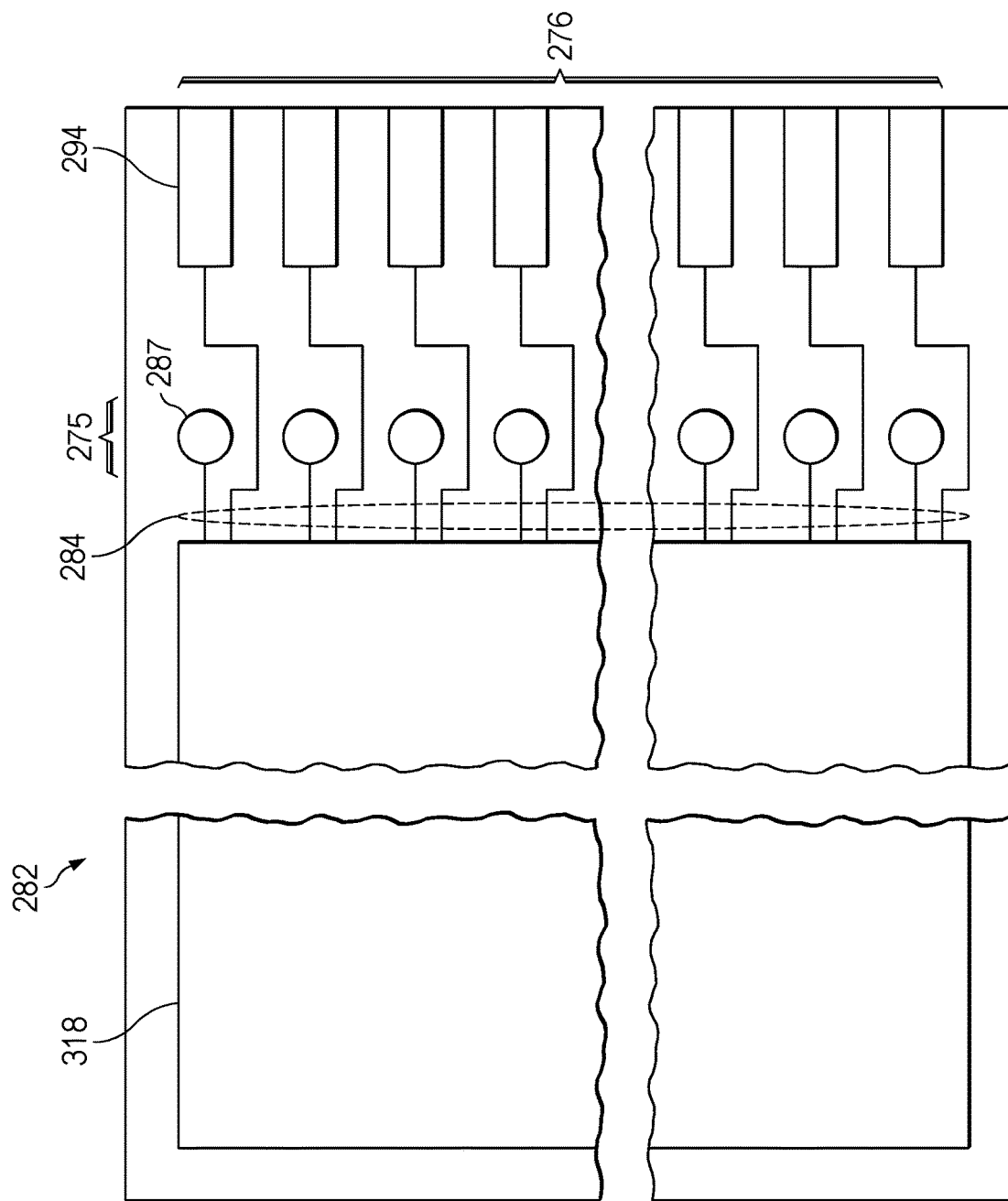
FIG. 17 is a top view of a top view of a valve block shown in FIG. 15, FIGS. 18A and 18B are section views of a valve assembly in the open and closed positions.

The valve block 282 is shown in a top view in FIG. 17. The block 282 includes the chamber driver 318 which is further described in FIG. 21. The driver 318 selectively activates each of a plurality of drive lines 284. Each of the lines 284 comprises two conductors which are coupled to each of chamber channel valve assemblies 275 and vent line valve assemblies 276. One of the channel valve assemblies 275 is valve assembly 287 and one of the vent channel assemblies 276 is valve assembly 294. See FIG. 16.

Figure 18A:
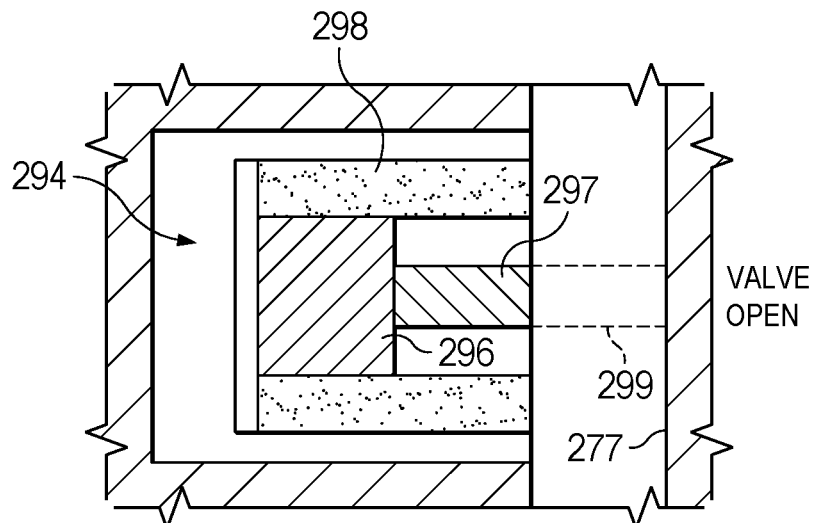
Figure 18B:
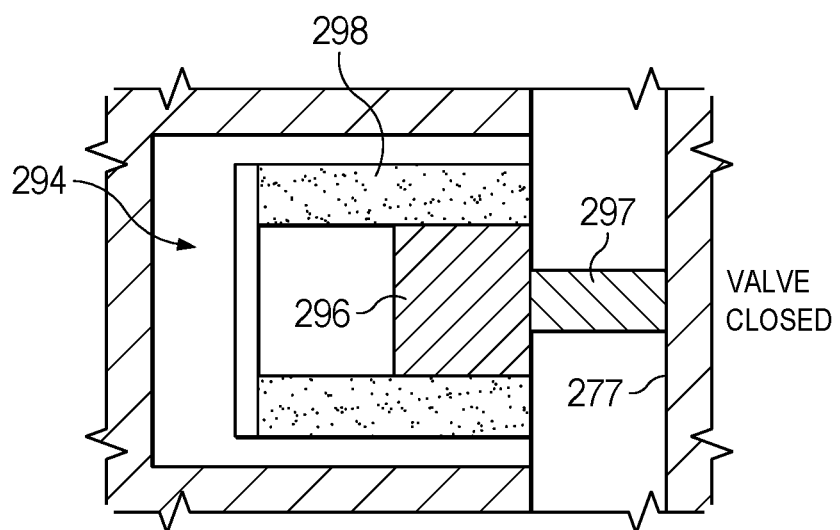

Operation of a representative valve assembly 294 is shown in FIGS. 18A and 18B. Assembly 294 is shown in the open position in FIG. 18A and in the closed position in FIG. 18B. The driver 296 can be a magnetic material which interacts with the electric field produced by the field generator 298. The polarity of the field produced by generator 298 determines the position of the driver 296 and therefore the positions of the valve element 297. Other types of physical actuators can similarly move the element 297 into and out of the channel vent line 277.

The valve assembly 294 is a micro-actuator. There are numerous types of micro-actuators known in the art which can perform as a driver for the valve assemblies 287 and 294. Examples of such micro-actuators are described in U.S.

Pat. No. 8,258,899, which issued Sep. 4, 2012 and which patent is incorporated herein by reference in its entirety.

Figure 19:
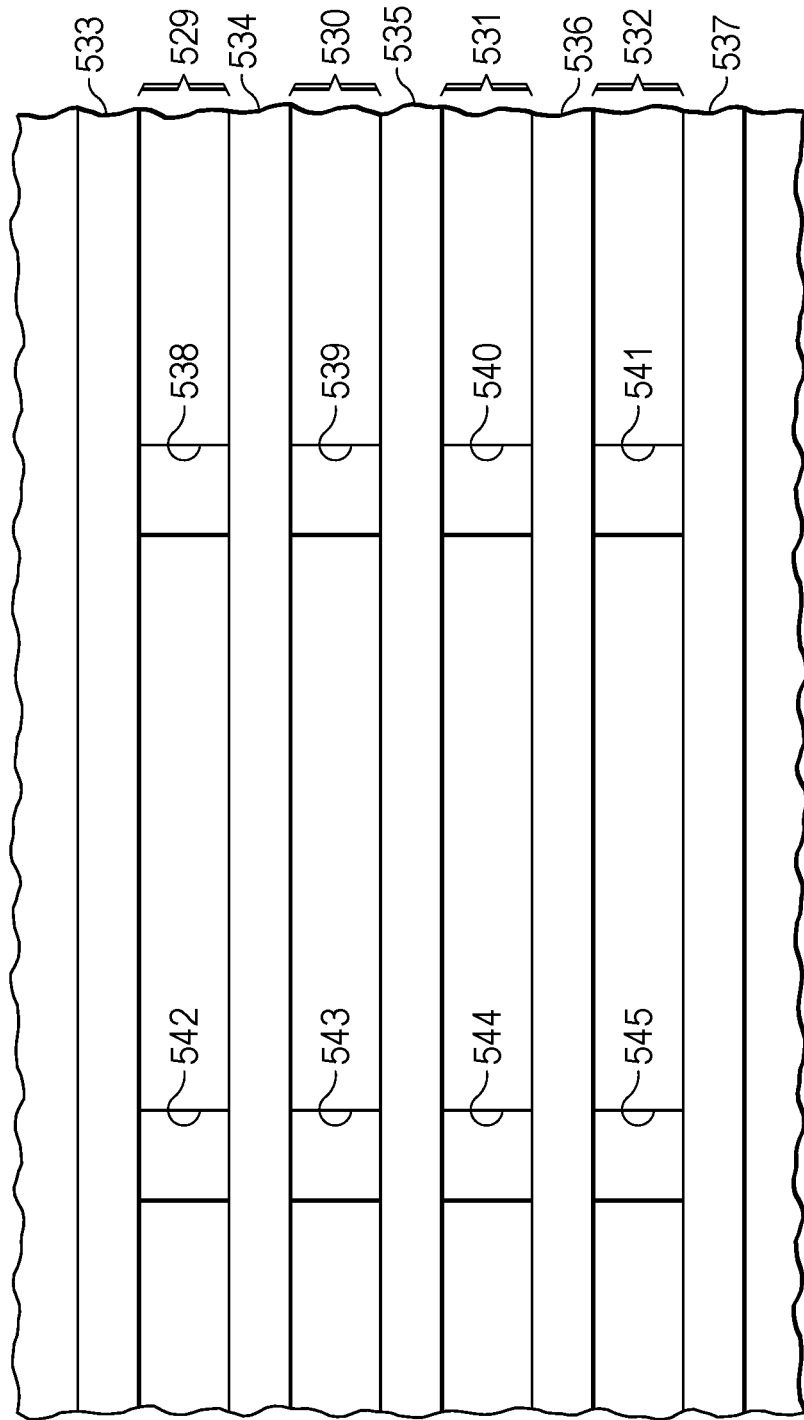
FIG. 19 is a partial bottom view of the middle layer of the cassette 58.

FIG. 19 is a view of the bottom of the middle layer 136 of the cassette 58. Channels 529, 530, 531, and 532 are formed between pairs of ridges 533, 534, 535, 536 and 537. The channels 529, 530, 531 and 532 have channel vent lines 538, 539, 540 and 541. The channels 529, 530, 531 and 532 have respective openings 542, 543, 544, and 545 which receive valve elements which when extended block fluid flow through the corresponding channel. See FIG. 16.

Figure 20:
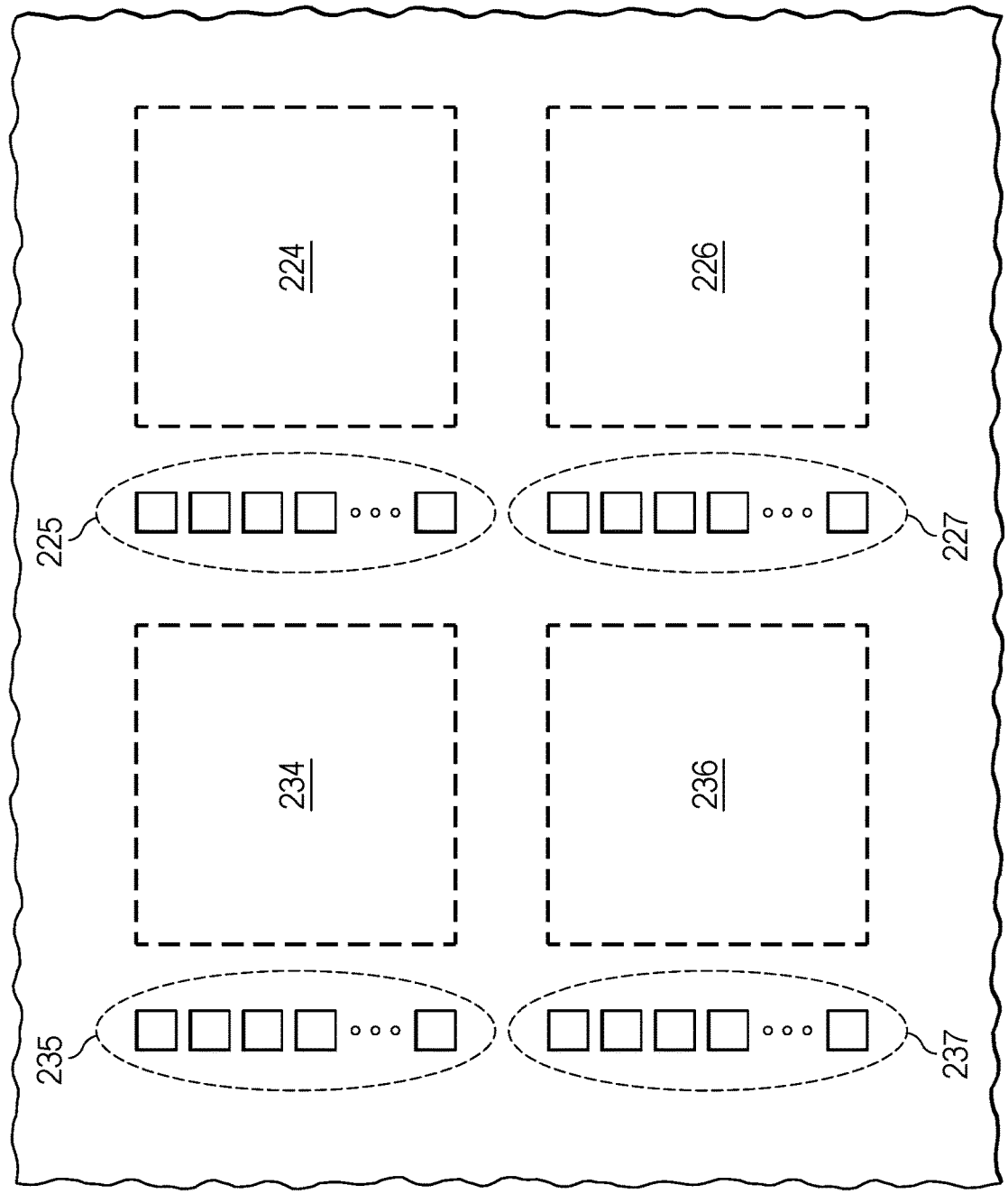
FIG. 20 is a partial top view of the top surface of the cassette shown in FIG. 16.

FIG. 20 (not shown to scale) illustrates the top of the middle layer 136. The dashed boxes represent the locations of holding chambers, for example, chambers 224, 234, 226, and 236 (See FIG. 9). Vent holes 235, 225, 237 and 227 respectively vent fluid from holding chambers 234, 224, 236 and 226. These vent holes are connected to cassette vent lines in the layer 134 and these vent lines empty into the sump 25 via line 45. See FIG. 1.

Figure 21:
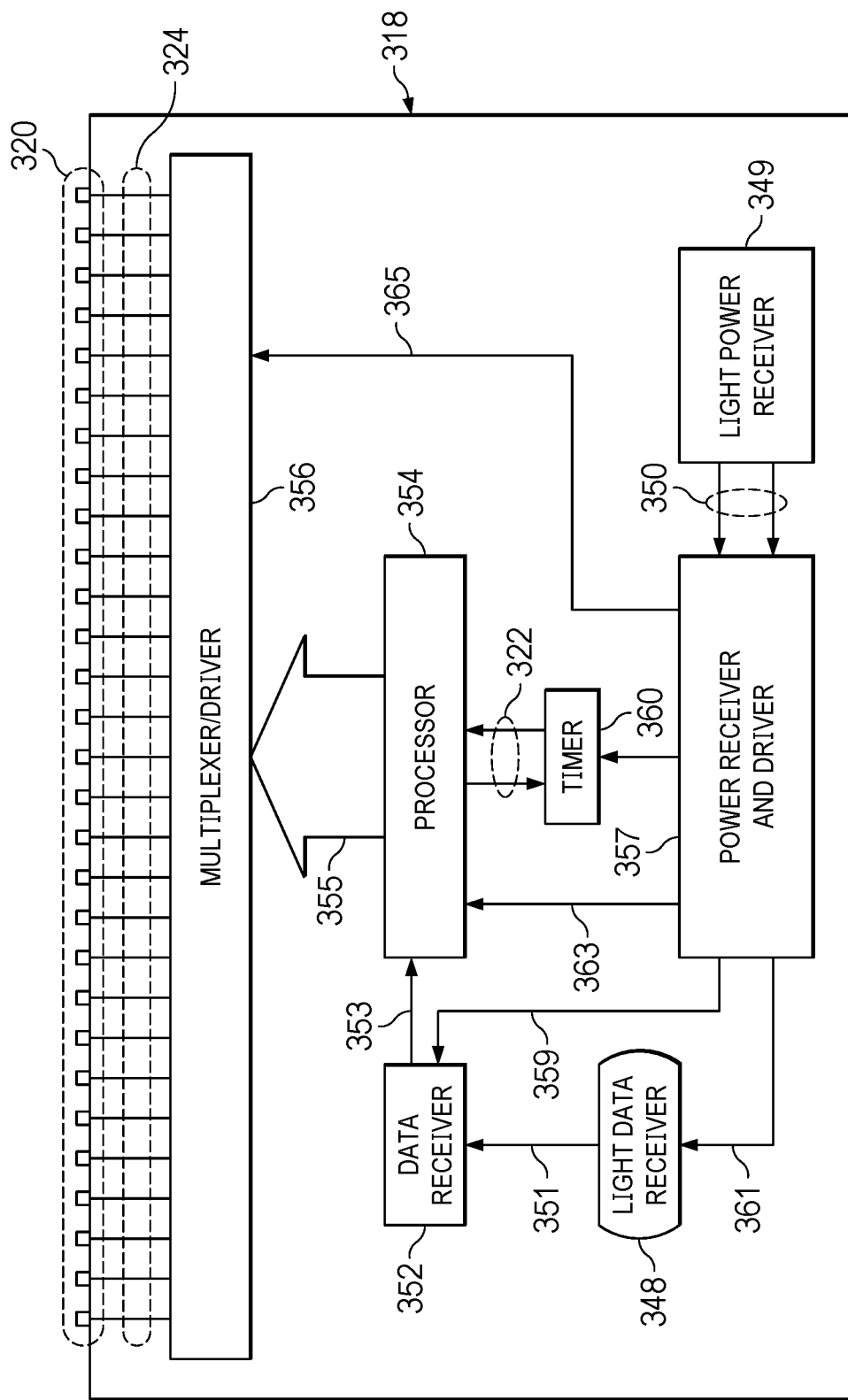
FIG. 21 is an electrical schematic block diagram of the chamber driver shown in FIG. 17.

An electrical block diagram of the driver 318 is shown in FIG. 21. Driver 318 is preferably an integrated circuit. The driver 318 includes a light data receiver 348 which receives pulsed light from an associated processor, described below, with data defining the voltage signals to be applied to the control lines for each valve in each of the channels in the associated chamber. The light data receiver 348 provides a received signal via a line 351 to a data receiver 352. The data receiver 352 provides a digital data stream via a line 353 to a processor 354. The processor 354 is coupled via a bus 355 to a multiplexor/driver 356. Driver 356 is electrically connected to the pads in a set of pads 320. Electrical power to operate the driver 318 is received as light by a light power receiver 349 (such as a photocell) and the electrical power is provided through lines 350 to the power receiver and driver 357. The light for the receiver 349 is transmitted from a light power transmitter 408 shown in FIG. 24. The transmitter 408 receives power via a line 415 which is coupled to the chamber processor 401. The power receiver driver 357 provides electrical power to the data receiver 352 via a line 359, to the light data receiver 348 via a line 361, to the processor 354 via a line 363 and to the multiplexor/driver 356 via a line 365. The driver 318 also include a timer 360 connected to processor 364 via lines 322 to provide clock and timing functions for the processor 364. The multiplexor/driver 356 selectively drives lines 324 which are respectively connected one for one to pads 320. Referring to FIG. 17, the pads 320 are respectively connected to lines 284 whereby multiplexor/driver 356 is electrically coupled to each of the channel valves 275 and vent valves 276. Each illustrated line to a valve is two electrical lines so as to provide a voltage difference. With this connection configuration, the chamber driver 318 can drive each of the channel valves 275 and vent valves 276. The use of power transmission by light eliminates the need for a physical power connection to the cassette 58. An alternative to the power transmission by light is a physical power connection line to the cassette 58.

Figure 22:
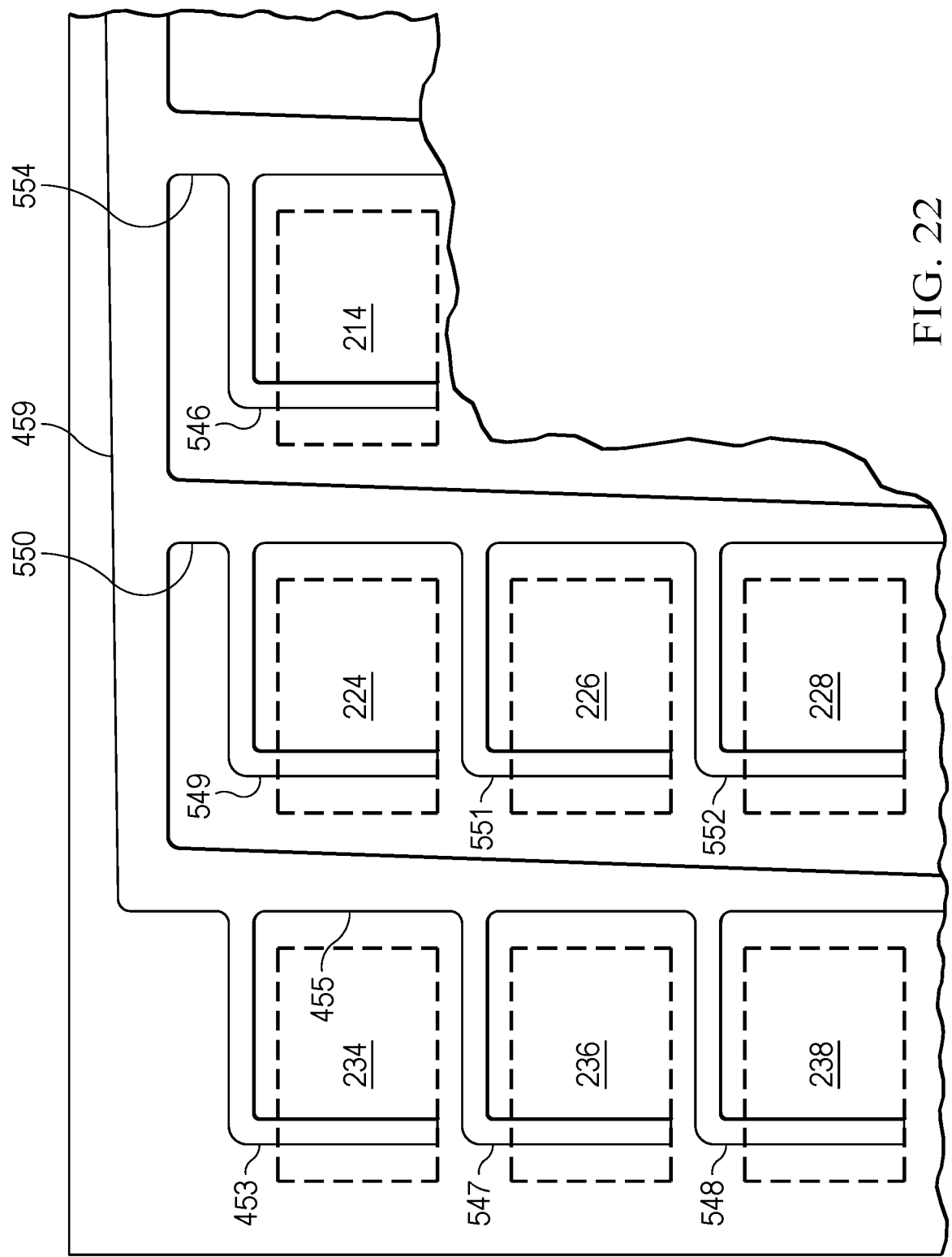
FIG. 22 is a top view of the top layer of the cassette 58 illustrating vent lines.
Figure 23:
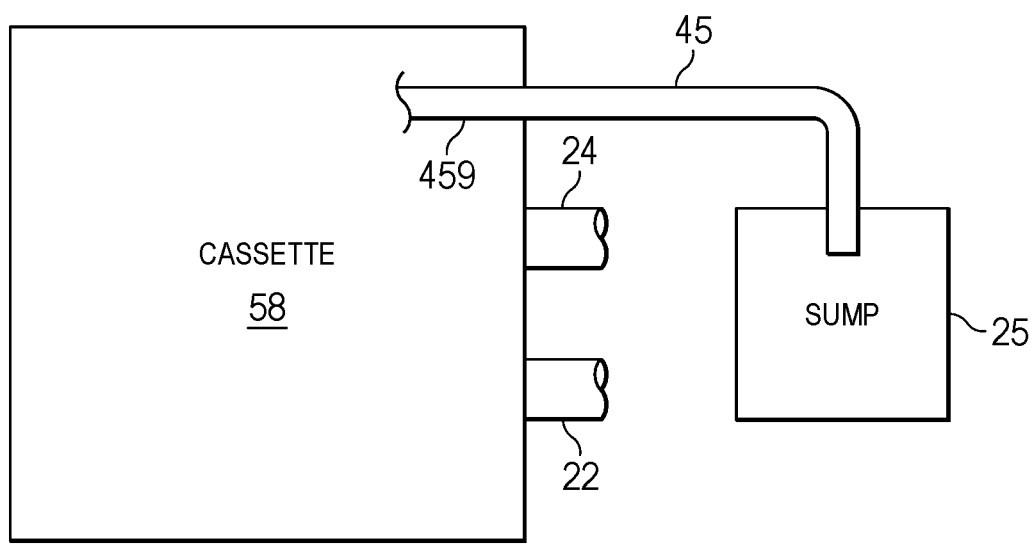
FIG. 23 is an illustration of a vent line and sump in association with cassette 58.

The flow of vented fluid from the chambers of a cassette 58 is shown in FIGS. 22 and 23. A representative chamber 234 (See FIG. 9) has a chamber exit vent line 453 that empties into a collection line 455 which in turn empties into a cassette vent line 459. All of the chambers in the cassette 58 empty into the vent line 459, which is connected to the drain line 45 such that the vented fluid from all of the chambers of the cassette 58 are delivered to the sump 25 (See FIG. 1 and FIG. 23). Chambers 236 and 238 have respective vent lines 547 and 548 that empty into collection line 455. Chambers 224 and 214 have respective vent lines 549 and 546 that empty into vent lines 550 and 554 which in turn empty into vent line 459. Chambers 226 and 228 have vent lines 551 and 552 that empty into vent line 550 which empties into vent line 550. In FIG. 23, vent line 459 is coupled to drain line 45 to convey the vented blood fluid to the sump 25.

There is one channel valve and one vent valve for each channel in each chamber of the cassette 58. The collection of valve assemblies is in the processing zone 250 of chamber 244, shown in FIG. 15.

Figure 24:
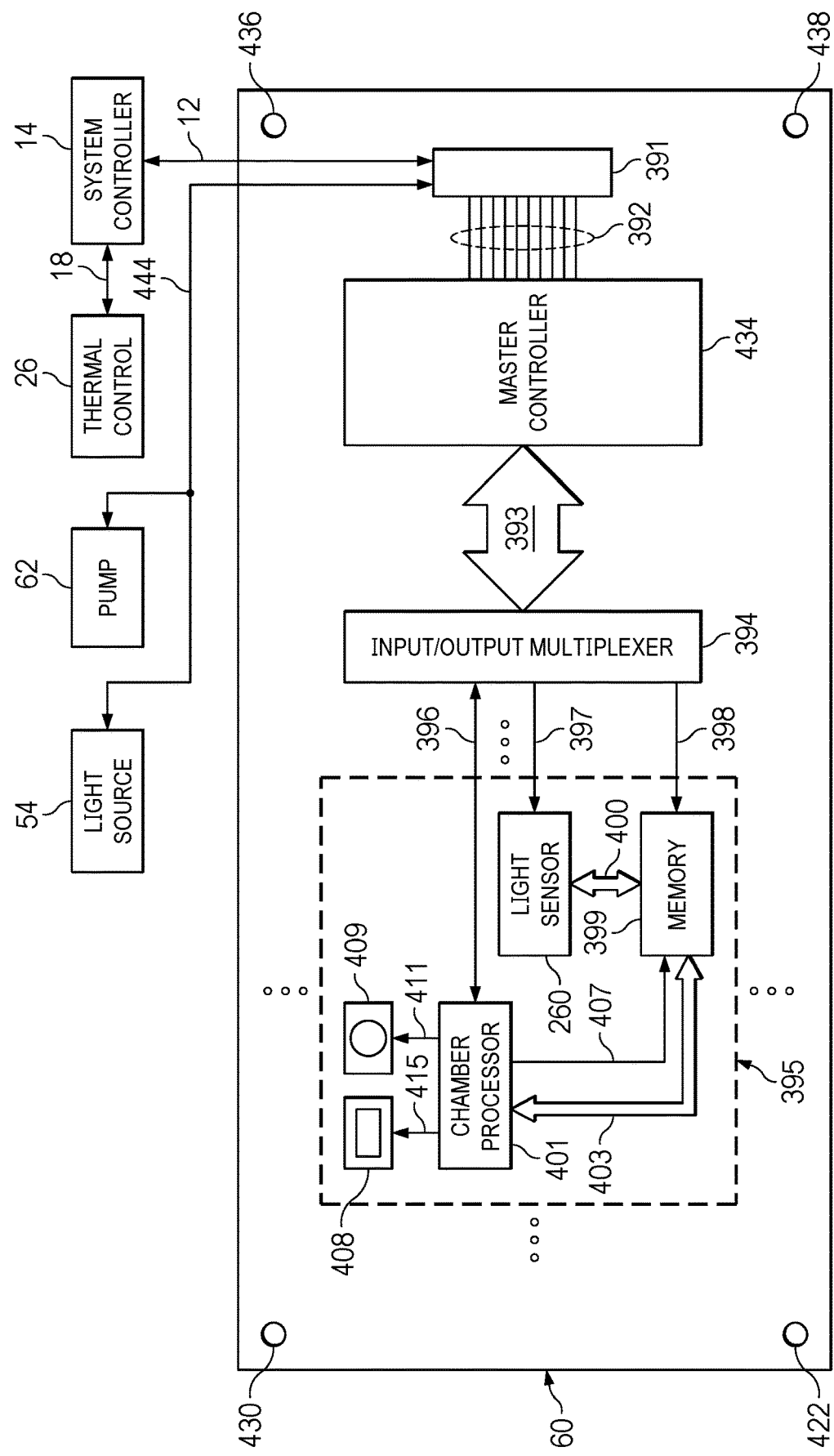
FIG. 24 is a partial electrical block diagram of the system shown in FIG. 1.

FIG. 24 is an electrical block diagram of components in the system illustrated in FIG. 1 with detailed structure shown for the imager and processor unit 60. The unit 60, in one embodiment, includes a printed circuit board with components mounted on it. The system controller 14 (See FIG. 1) is coupled via a cable 12 to the unit 60 by use of a connector 391 and a cable 392 to a master controller 434. The controller 434 can be, for example, a microprocessor, a dedicated gate array or other processing device. The controller 434 can activate and deactivate the light source 54 and pump 62 via a cable 444. The master controller 434 is connected via a cable 393 to an input/output (I/O) multiplexor 394. The multiplexor 394 is connected to each of a plurality of assemblies 395. In an embodiment, there is one of the assemblies 395 for each of the chambers of the cassette 58, such as the 30 chambers 184-242 shown in FIG. 9. The master controller 434 can communicate via the multiplexor 394 to each of the assemblies 395 and can receive communication from each of the assemblies 395. Each assembly 395 includes a light sensor 260 which is positioned below and aligned with a corresponding chamber in the group of chambers 184-242. Each light sensor has an array of light sensitive pixels. See FIG. 25. The multiplexor 394 communicates with the assembly 395 via cables 396, 397 and 398. There is a similar set of cables, such as printed circuit board traces, for each of the other assemblies in the unit 60. Each light sensor array 260 is aligned with a corresponding holding chamber for receiving light which has passed through the corresponding holding chamber. The light sensor 260 array is positioned parallel to but offset from the corresponding holding chamber.

Figure 25:
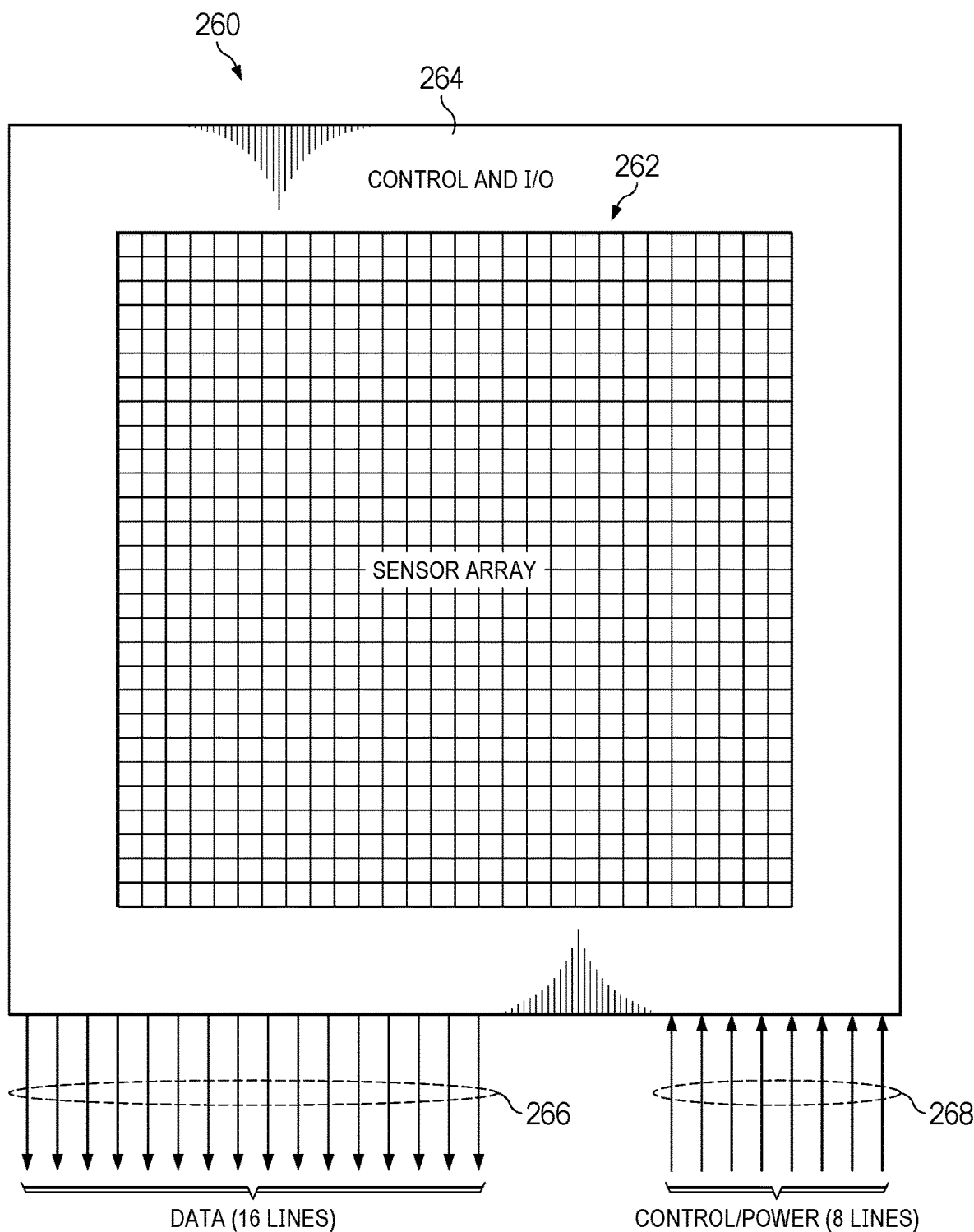
FIG. 25 is a top view of a light sensor array with control and data lines.

Further in reference to FIG. 24, each assembly 395 includes a memory 399 which receives digital data from the light sensor 260 via a cable 400 comprising data and control lines (See FIG. 25). When the light sensor 260 has received light and has a data state for each pixel therein, this data is transferred to the associated memory 399. Each assembly 395 further includes a chamber processor 401 which has a data bus 403 and control line 407 coupled to the memory 399. The processor 401 can command that part or all of the data in memory 399 be transferred to the processor 401 to be processed. The master controller 434 communicates via the multiplexor 394 and cable 396 to the chamber processor 401, the cable 397 to the light sensor 260 and cable 398 to the memory 399. Each assembly 395 further includes a light data transmitter 409, for example a modulated laser beam generator, connected via a data transmission and control cable 411 to processor 401. Receiver 348 shown in FIG. 21 receives the light data.

As shown in FIG. 1, the heater/cooler thermal control unit 26 is controlled by the system controller 14 through line 28.

Light data transmitter 409 sends data to the data light receiver 348 in the chamber driver 318, see FIG. 21.

Referring to FIG. 24, unit 60 has holes 422, 430, 436 and 438 near the corners of the unit for receiving the rods 30, 32, 34 and 36 shown in FIG. 2.

An example of light sensor 260 array integrated circuit for use with the present invention is shown in FIG. 25. A sensor array 260 includes an array 262 of individual pixel cells, each pixel cell further described below. The illustrated pixels are not to scale. Surrounding the array 262 of pixel cells is circuitry termed control and I/O (Input and/or Output) 264 which controls the operation of the sensor array 260 and the transfer of pixel data collected by the sensor array 260. A group of data lines 266, for example 16 parallel lines, transfers pixel data from the pixel array 262 to an associated memory. A set of control and power lines 268, for example 8 lines, controls the operation of the sensor array 260 and provides power for operation of the sensor array 260 circuitry. As further described below, the sensor array receives a reset signal to set an initial charge state in each of the pixels. When the pixels are exposed to light, each pixel is discharged from the initial state to a final state (the pixel data) depending on the amount of light that was received by the pixel. A command is sent through lines 268 which causes the sensor array 260 to transfer the collected pixel data through one or more of the lines 266 to an associated memory.

As an example, the pixel array 262 can have a pixel size of 0.5 micron by 0.5 micron (square configuration) and the light sensitive array has a size of 2 centimeters by 2 centimeters. There is only one bit per pixel, either light or dark, therefore, the pixel data for one image is the size of the number of pixels. These dimensions are exemplary only, and a sensor array larger or smaller than array 262, as shown, may be used.

A circuit for each of the pixels in the array 260, can be any one of many types. A 3-T (three transistor) pixel circuit is shown in FIG. 26 and a 4-T (four transistor) pixel circuit is shown in FIG. 27.

Figure 26:
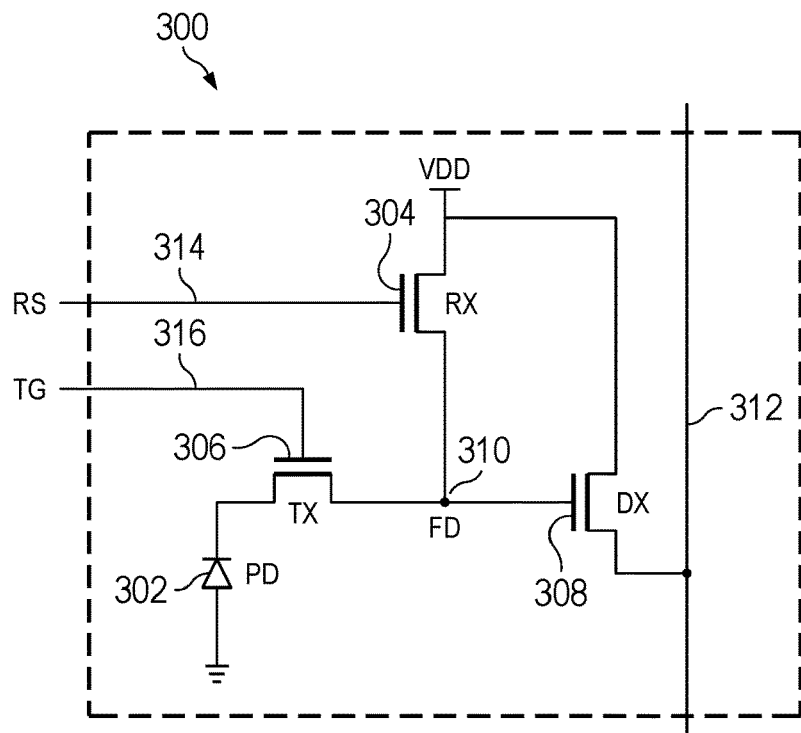
FIG. 26 is an electrical schematic of a 3T image sensor cell.

Referring to FIG. 26, a 3-T pixel circuit 300 includes a photodiode (PD) 302, a transfer transistor 306, a reset transistor 304, a drive transistor 308 and a floating diffusion (FD) 310. A reset signal (RS) is sent through a line 314 to the gate of reset transistor 304. A transfer control signal (TG) is provided through a line 316 to the gate of transistor 306. The image data produced by pixel circuit 300 is transmitted through column line 312.

In operation, the pixel circuit 300 is initially reset by turning transistor 304 (RX) on to charge node FD 310 to VDD. Next the TG signal turns on TX transistor 306 which couples the node FD to the cathode of photodiode 302. Upon receiving light at the photodiode 302, the diode reverse conducts and discharges node FD dependent upon the amount of light received by the diode. The charge on node FD drives the transistor 308 (DX) which applies a corresponding current to the column line 302.

Figure 27:
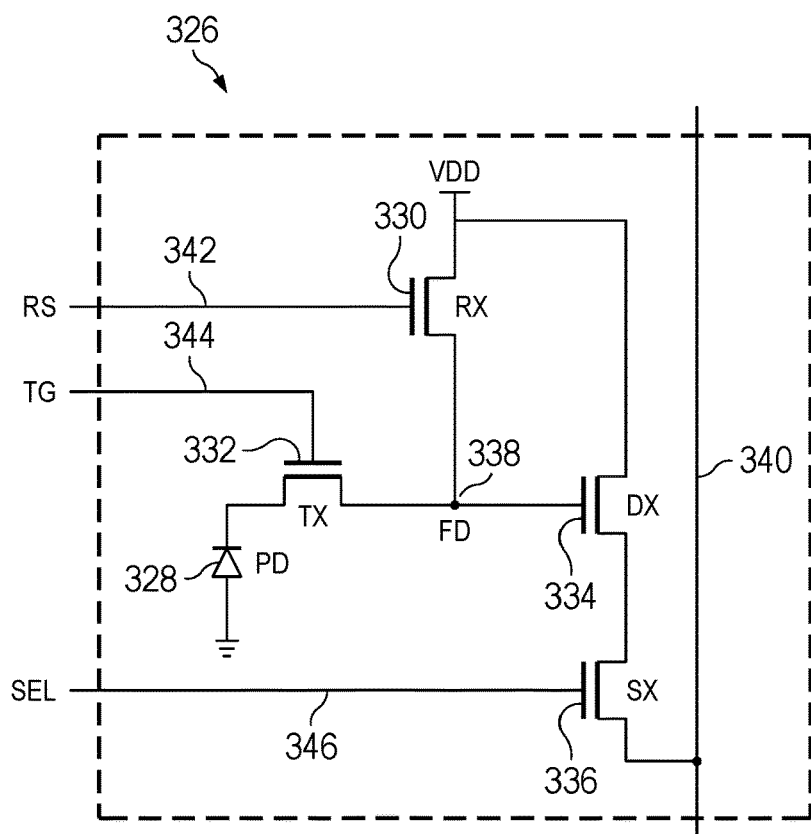
FIG. 27 is an electrical schematic of a 4T image sensor cell.

A 4-T pixel circuit 326 is shown in FIG. 27. This circuit has a photodiode (PD) 328, a reset transistor 330 (RX), a transfer transistor 332 (TX), a drive transistor 334 (DX), and a select transistor 336 (SX). A floating diffusion 338 (FD) is connected to the gate of transistor 334. Transistor 330 (RX) receives a reset signal through line 342. Transistor 332 (TX) receives a drive signal (TG) through a line 344. Transistor 336 (SX) receives at its gate a select control signal (SEL) via a line 346.

The pixel data, which is the measured light, is sent through the column lines 312 and 340 in FIGS. 26 and 27. At the end of these lines there is an analog to digital converter to produce a high or low, 1 or 0, digital signal. This is essentially a threshold detection. Each pixel data represents dark or light, depending on how much light was received at the pixel.

Operation of the pixel circuit 326 (FIG. 27) begins with receipt of a reset (RS) signal at transistor 330 to charge node FD 338 to VDD. Next, the transfer control signal (TG) turns on transistor 332 to couple the cathode of photodiode 328 to node FD. When the photodiode 328 receives light, charge is drawn from node FD to reduce the voltage on node FD, which drives the gate of transistor 334 (DX). For readout of data from the pixel, signal SEL is applied to turn on transistor 336 (SX) to couple transistor 334 (DX) to the column line 340. The column line 340 is sequentially used to transfer data from all of the pixels connected to the column line.

Figure 28:
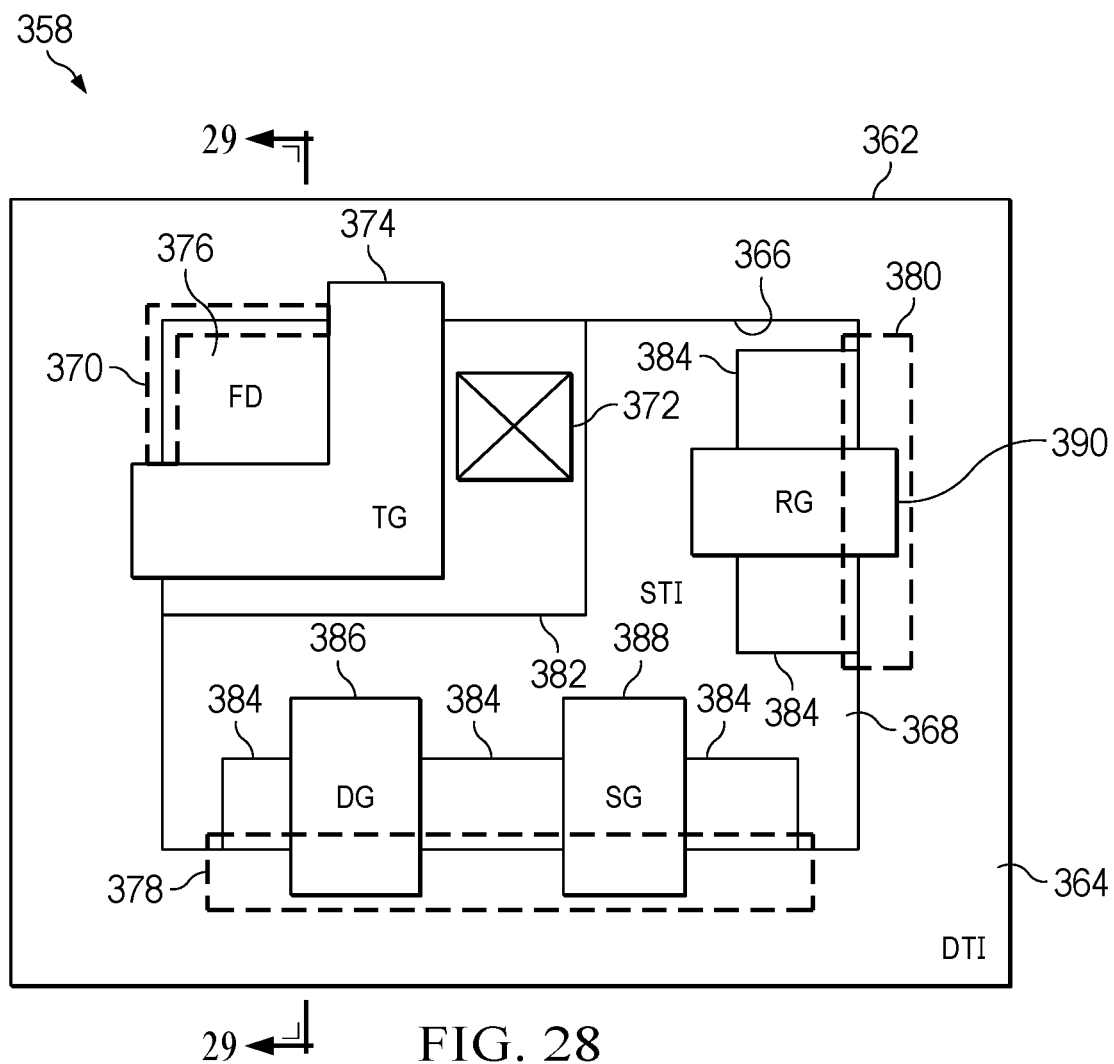
FIG. 28 is a top view of a layout of an image sensor cell.
Figure 29:
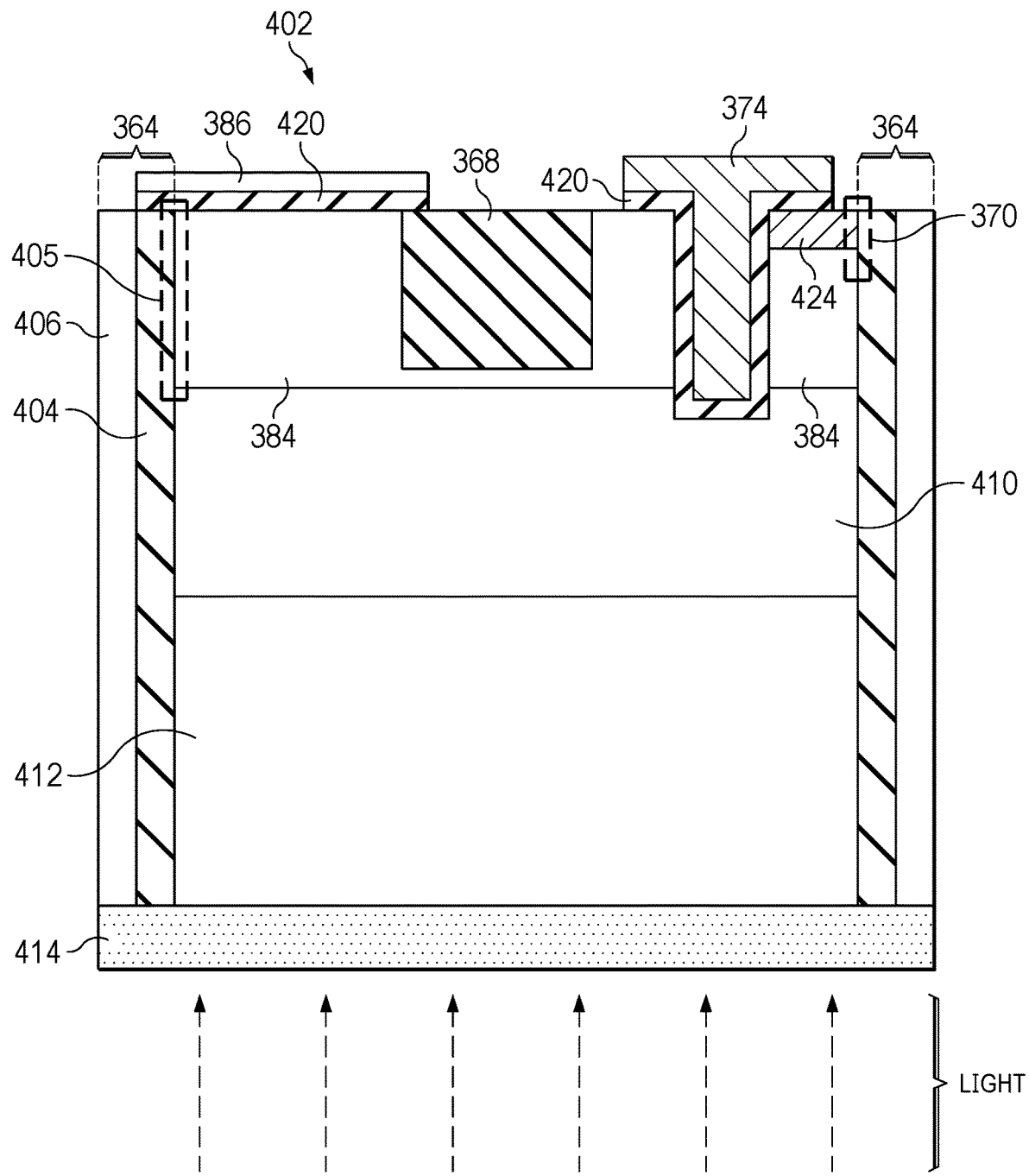
FIG. 29 is a section view of a layout of an image sensor cell.

FIGS. 28 and 29 illustrate a physical integrated circuit structure for implementing the 4-T pixel shown in FIG. 27. Layout 358 in FIG. 28 is a top view. A unit pixel area 362 is the area occupied by the pixel structure. A deep trench isolation (DTI) region 364 serves to isolate each pixel from surrounding pixels. Active area 366 is the area of the pixel which receives light. A shallow trench isolation (STI) 368 separates active elements of the pixel. First border 370, second border 378 and third border 380 serve to isolate elements of the pixel circuit to reduce noise. 372 is a ground element. 374 is a transfer gate. 376 is a floating diffusion. 382 is a p-well. 384 is a p-well. 386 is the drive transistor gate. 388 is the select transistor gate and 390 is the reset transistor gate.

FIG. 29 is a section view layout 402 along line 29-29 of the structure shown in FIG. 28. The common elements in FIGS. 39 and 40 have the same reference numerals. Element 404 is an oxide isolating layer, 405 is a border, 406 is a polysilicon isolation layer and 410 is a photodiode in conjunction with the epitaxial layer 412. Element 414 is an anti-reflection layer. 420 is a gate isolation layer. 424 is a floating diffusion (FD 338 in FIG. 27). Light, shown by the upward pointing vertical arrows in FIG. 29, produced by the light source (54 in FIG. 3), is transmitted to the pixel structure and in particular to the photodiode for measuring the light received by this one pixel.

Figure 30:
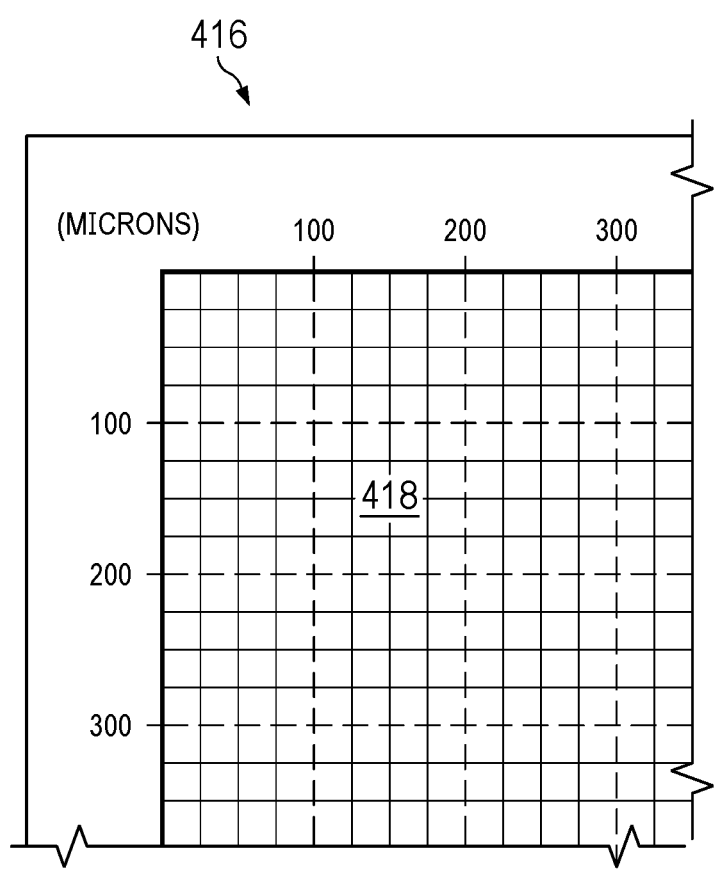
FIG. 30 is an illustration of cassette chamber zones used for physical calibration.
Figure 31:
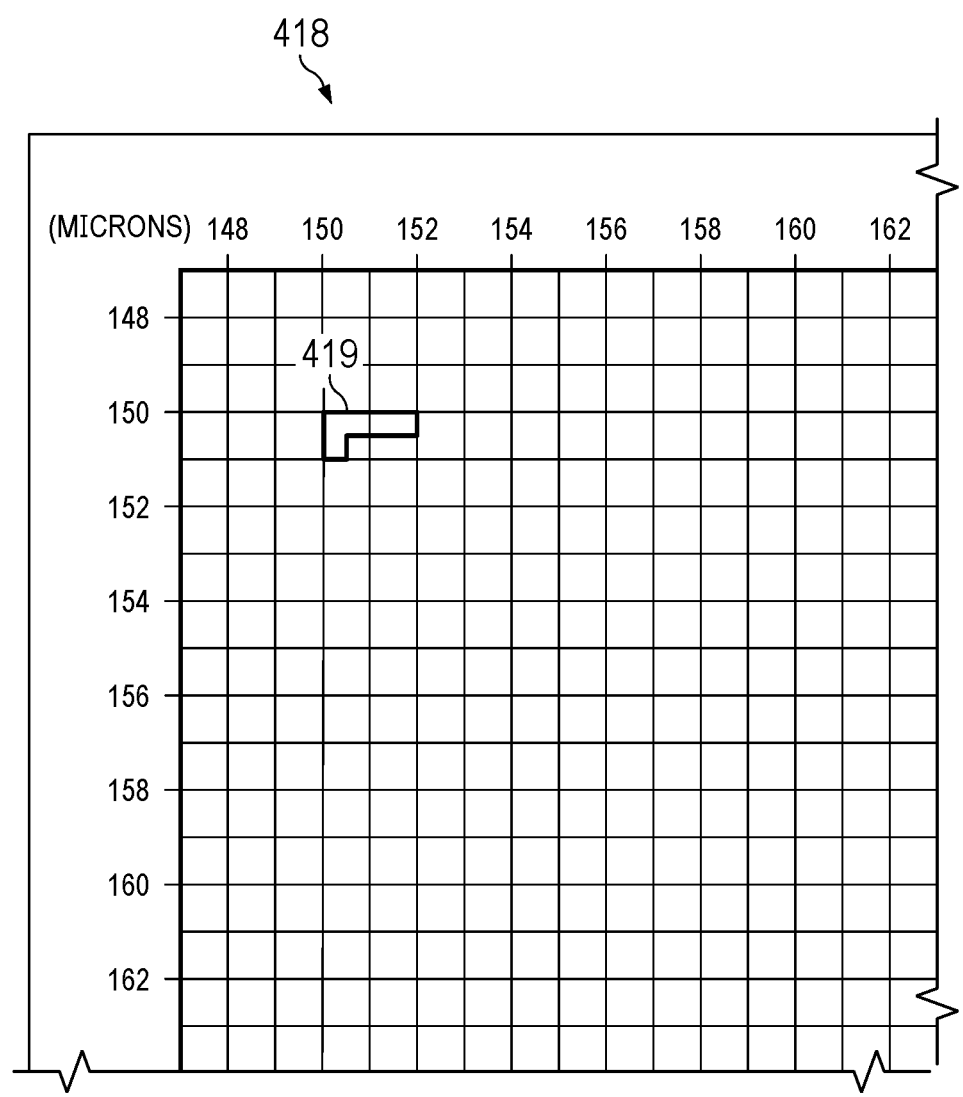
FIG. 31 is an illustration of a cassette chamber zone with a calibration marker.
Figure 32:
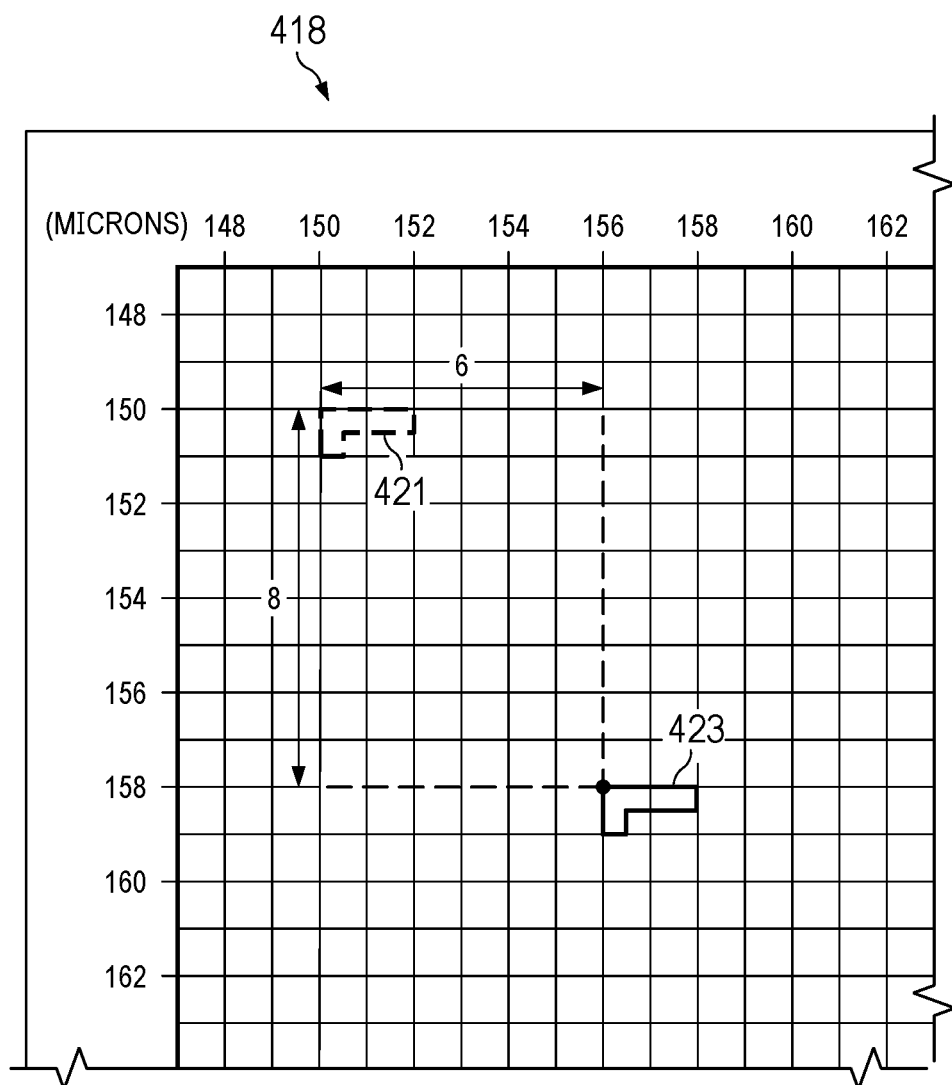
FIG. 32 is an illustration of a portion of a sensor array illustrating physical calibration.

Referring to FIGS. 30, 31 and 32, there is shown physical calibration apparatus and a process for the alignment of a cassette chamber with the underlying light sensor. A segment 416 of a chamber, such as any of chambers 184-242 (FIG. 9) is subdivided into a set of areas, which, in this example, each area has a size of 100 microns by 100 microns. Area 418 is near the corner of a cassette chamber, and FIG. 31 illustrates a middle region of the area 418. A light blocking calibration marker 419 is positioned approximately in the middle of area 418. The upper left corner of the marker 419 is at the position of 150 microns horizontal and 150 microns vertical. The marker 419 is printed on the interior surface of the cassette chamber. The marker, in this example, has a unique L-shape which is 2 microns long, 1 micron wide and the body is 0.50 micron wide. This shape can be readily identified in pattern recognition operation in a processor. FIG. 32 illustrates a region of the light sensor beneath the chamber having the marker 419. If the chamber and underlying light sensor were perfectly aligned, the shadow image of the chamber marker 419 would be at the same position in the light sensor, as shown by the dotted marker outline 421. But, if the chamber and light sensor are not in perfect alignment, the marker 419 could produce a shadow image 423 which is offset from the dotted marker outline 421. In the illustrated example, the shadow image 423 is offset by 6 microns to the right and 8 microns down. Thus, for the area 418, the alignment correction is (−6, −8). Thus, for any image in the 418 area for the light sensor, the position determined in the light sensor is adjusted by −6 microns horizontally and −8 microns vertically. Each of the areas of the cassette chamber is provided with a printed marker, such as 419 and the shadow image of each marker in the light sensor is determined. A physical calibration table is prepared having a pair of correction numbers for each area, such as 418, of the cassette chamber. The corrected position from the sensor array is the actual position in the overlying cassette holding chamber.

Referring to FIGS. 25 and 31-32, the sensor array can be divided into calibrations zones. For a 2 cm by 2 cm sensor array, each calibration zone can be, for example, 100 microns by 100 microns. With these sizes, the array 262 has $4 \times 10^4$ calibration zones. If the calibration zone is larger, there will be fewer calibration zones in the sensor array. Each calibration zone can be calibrated, as described, and the calibration values can be different between calibration zones. This compensates for nonlinearities in alignment across the sensor array 262.

The chamber processors, such as 401 shown in FIG. 24, have one processor used with each sensor array, can be, for example, a microcomputer, a graphic processor or a custom gate array. The master controller can be, for example, a microcomputer or a custom gate array.

The 30 sensor arrays (See FIGS. 9 and 24) are each aligned with a holding chamber in cassette 58. There is a one-to-one relationship. For example, holding chamber 184 (FIG. 9) is positioned over and aligned with a light sensor such as 260 (FIG. 24). Each of the remaining holding chambers (FIG. 9) of the cassette 58 is likewise located over and aligned with a corresponding sensor array (See FIG. 24)

Operation of the apparatus described herein can include an initial calibration of the light energy produced from the light source 54 to be sufficient to activate, but not overdrive, the individual pixels in the light sensors 260 shown in FIGS. 24 and 25. Also referring to FIG. 3, as directed by the master controller 434, after receiving an energy calibration command from the system controller 14, the energy calibration process first resets all of the pixels in all of the sensor arrays 260. Next, it activates all of the pixels in all of the sensor arrays and then activates the light generation from the light generator 54 for a selected time and intensity. The pixels in the light sensors are then deactivated, the pixel data transferred to the corresponding memory and the processor activated to run a light energy calibration routine. If the light energy is sufficient, all of the pixels will be light, that is, no dark pixels since there is nothing in the cassette holding chambers during this calibration process. The markers in the chambers are excluded. The processor counts the number of dark pixels. The master controller polls all of the chamber processors to collect the number of dark pixels. If the number of dark pixels exceeds a preset threshold, such as 0.001%, the calibration process is repeated and the selected time is incrementally increased until the number of dark pixels is less than the preset threshold. If the initial measurement shows the number of dark pixels to be less than the present threshold, the process is repeated with shorter light activation times until the threshold is crossed and the last lower value is selected as the light activation time. The light energy can be varied by changing the length of time the light is on, or by varying the intensity of the light. In either case, a light activation value, either time or intensity, will be produced.

Figure 33B:
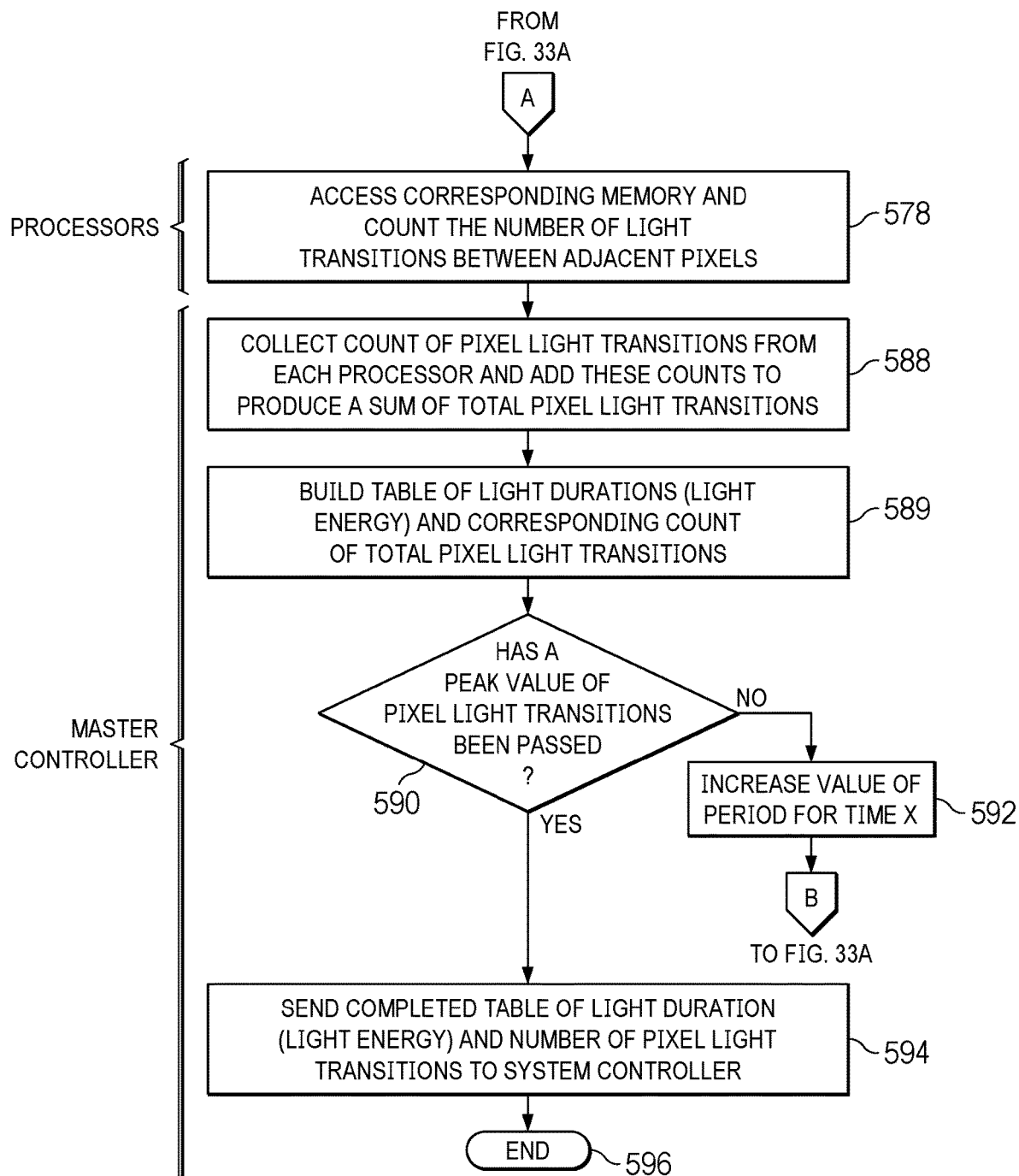

Light energy calibration can also be performed after the blood holding chambers have been filled as shown by the steps in FIGS. 33A and 33B. The system controller 14 initiates the filled chambers light energy calibration operation by sending a command to the master controller 434. See step 568. The master controller 434 receives the calibration command from the system controller at step 569. Referring to FIG. 24, the controller 434 drives the pump 62 to fill the holding chambers in cassette 58 (FIGS. 3 and 9). See step 570. Next, in step 572, the controller 434 sends a reset command to each of the light sensors 260. After the pixels in each sensor are reset, the controller 434 commands (step 573) each light sensor array to be activated. Next, in step 574 the light generator 54 is activated for a period of time X. The controller 434, in step 575, deactivates all of the light sensor arrays, and in step 576 commands each sensor array to download its pixel data to the corresponding memory. Next, in step 577, the controller commands each chamber processor associated with a sensor array to (step 578) access the pixel data in the corresponding memory and perform a light calibration process in which the number of light transitions between adjacent pixels is counted. The transition can be either light to dark or dark to light. Each pixel has four adjacent pixels and each possible transition is examined. For example, a dark pixel surrounded by four light pixels produces four transitions. In step 588, the controller 434 then collects the pixel transition count from each processor and adds them together to produce a total transition count corresponding to the period of time the light generator was on. In step 589, the master controller produces a table of light durations as shown below in Table 1. Next the above process is repeated with an incrementally longer period of time for the operation of the light generator. The number of transitions for this period is determined and recorded. Next, in question step 590, it is determined if the peak value of the number of light transitions has been passed. This is selected, for example, by having 100 sequential transition counts lower than a preceding transition count. If the response to question step 590 is "NO", in step 592, the value of X is increased by a selected increment, and control is returned to step 572. This process is repeated until a peak of transition number is reached, as noted. If the response to question step 590 is "YES", the master controller 434, in step 594 sends the completed table of light duration and count of pixel transitions to the system controller 14. This calibration process terminates at STOP step 596. An example of such data is as follows. The light energy value is a relative measure and the Pixel Transitions number is a truncated value, such as billions of transitions.

TABLE 1

| Relative Light Energy | Pixel Transitions |
| --- | --- |
| 1 | 50 |
| 2 | 65 |
| 3 | 85 |
| 4 | 100 |
| 5 | 120 |
| 6 | 140 |
| 7 | 150 |
| 8 | 165 |
| 9 | 160 |
| 10 | 150 |
| 11 | 135 |
| 12 | 125 |
| 13 | 115 |
| 14 | 105 |
| 15 | 90 |

As seen in the above data listing in Table 1, the optimum light energy value is "8" which corresponds to the pixel transition value "165". The number of pixel transitions is an indicator of the quantity of image information present in the pixel data and is likely the best image data. Therefore, for this instance of testing, the light energy should be set to the relative level of "8" for the process described herein to identify and locate pathogen cells in the blood. As noted above, the light energy can be varied by time duration or by the intensity of the light produced.

Figure 34:
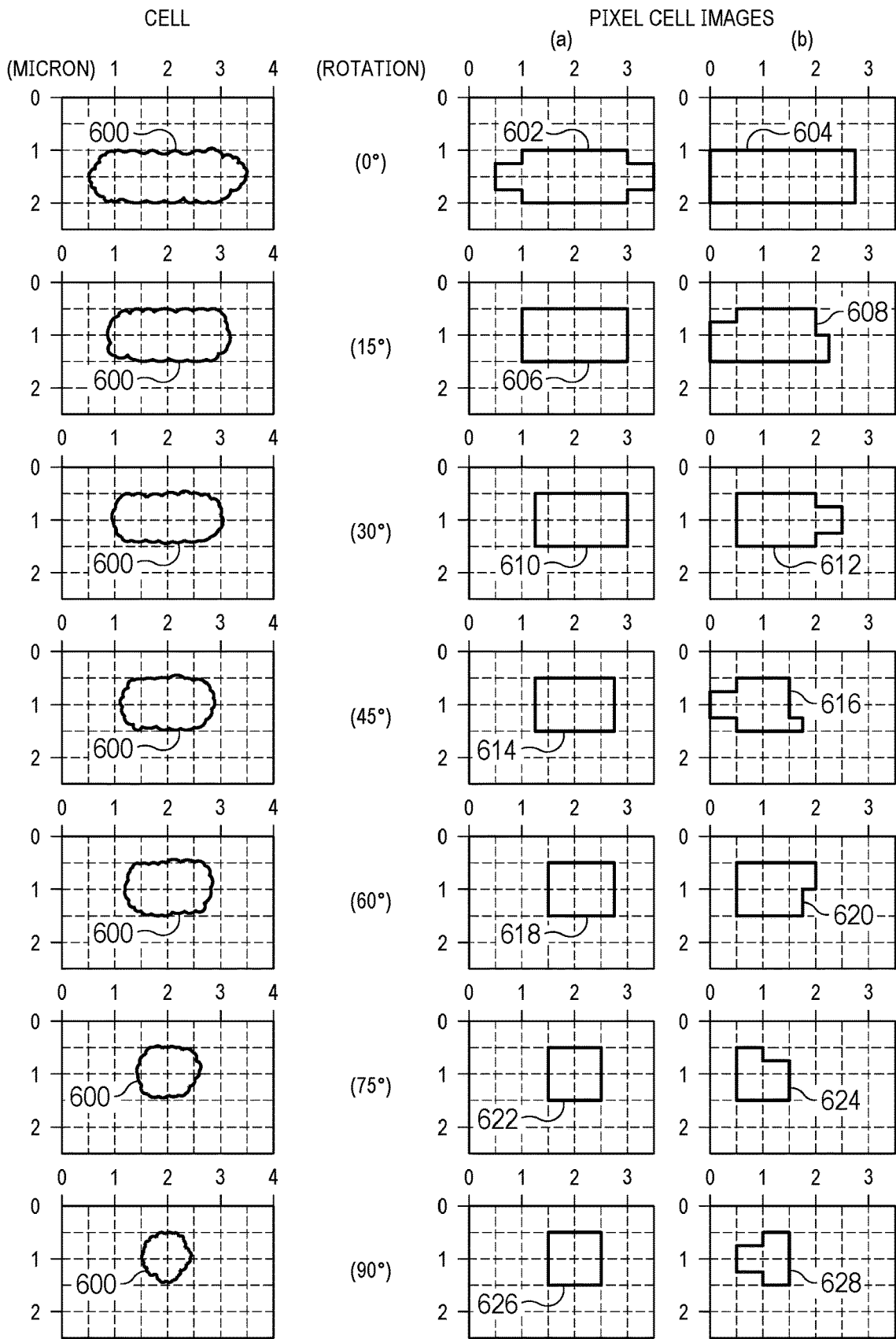
FIG. 34 is a set of pathogen cell image views for pattern recognition.

A pathogen cell, together with a measurement scale, is shown in multiple positions in FIG. 34. *E. coli* is a rod-shaped bacterium. The dimensions for this bacterium can vary but some species can be in the range of 2-3 microns long and 0.25 to 1 micron thick. In FIG. 34, there is shown in the left column an *E. coli* bacterium cell 600. The left column shows an actual view of a cell and the two right columns show shadow images that can be produced by that view of the cell by the sensor arrays (FIG. 25). These views are based on a system as described with 0.50 micron by 0.50-micron sensor array pixels. The right two columns show shadow images produced by the corresponding cell in the left column. The cell 600 is shown at multiple rotations along a vertical axis with angles of 0, 15, 30, 45, 60, 75 and 90 degrees. These multiple views are required because the cell could be at any rotation position as it is viewed in a holding chamber. The right two columns (a) and (b) represent possible variations on the image produced by the cell positioned at the indicated rotation. Images 602 and 604 can be produced by cell 600 at rotation of 0 degrees. These can differ due to edge effects and small threshold differences in pixel sensors. Images 606 and 608 could be produced for rotation 15 degrees, 610 and 612 for rotation 30 degrees, 614 and 616 for 45 degrees, 618 and 620 for 60 degrees, 622 and 624 for 75 degrees and 626 and 628 for 90 degrees. The images 602-628 are in the reference image library for the pathogen cell 600. These images are the search targets in the pixel data for identifying and locating the pathogen cells. These images can be located in the pixel data by the use of pattern recognition. Pattern recognition for detecting predetermined images in a digital data field is well-known technology. An example patent describing such technology is U.S. Pat. No. 9,141,885 issued Sep. 22, 2015 which patent is incorporated herein by reference in its entirety.

Figure 35:
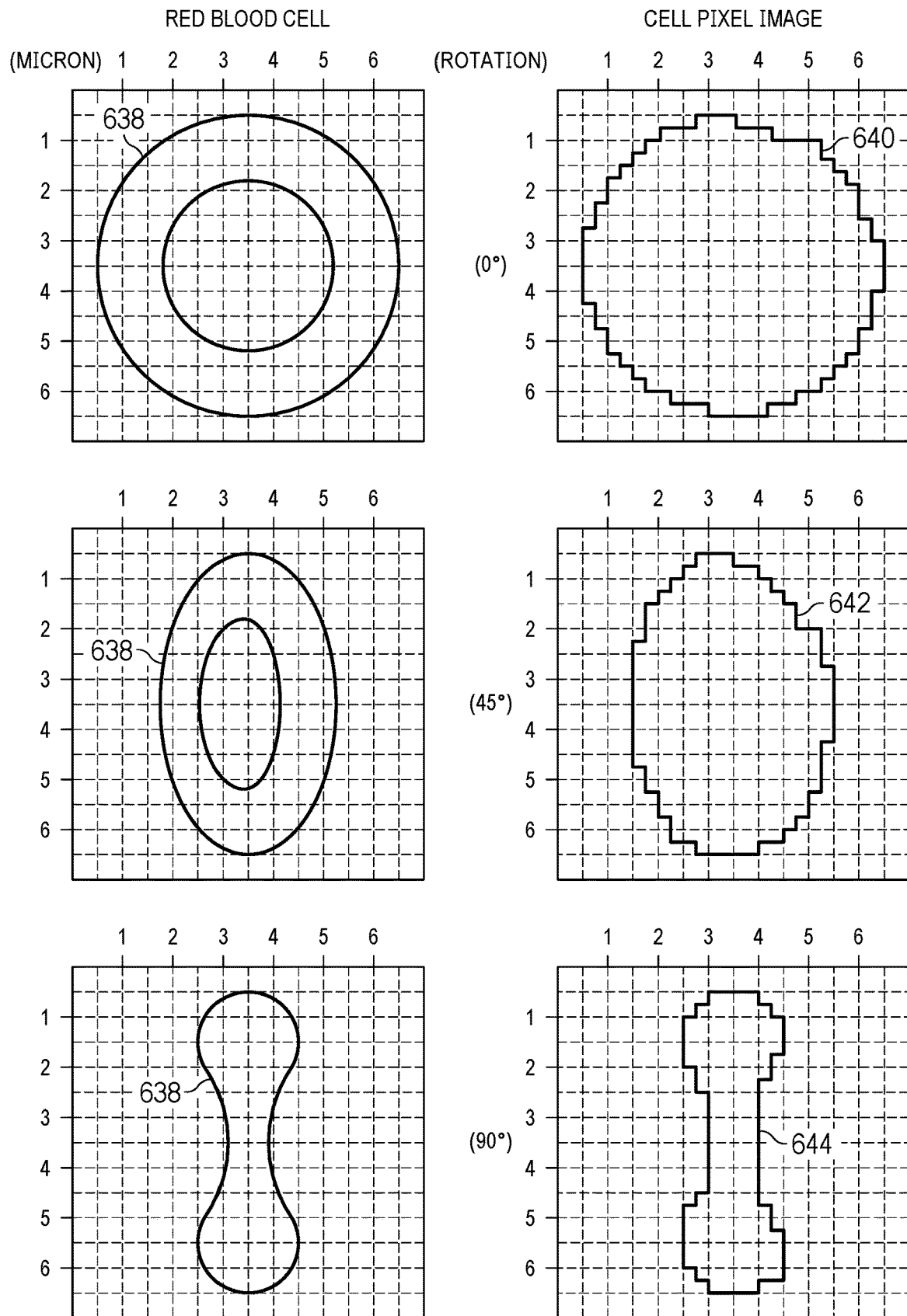
FIG. 35 is a set of red blood cell images for pattern recognition.

Referring to FIG. 35, there are shown views of corresponding shadow images of red blood cells, which comprise the majority of cells in human blood. The size of red blood cells can vary, but can be in the range of 6-8 microns. In FIG. 35, left column, there is shown a red blood cell 638. A red blood cell has a disc shape with a flattened center where the thickness may be 1-2 microns. Cell 638 with a rotation of 0 degrees can produce the shadow image 640, with rotation 45 degrees the shadow image 642 and with rotation of 90 degrees the shadow image 644. These images are included in the image library as being images to be ignored since they are different from the bacteria or other pathogen images that are sought to be found.

Figure 36:
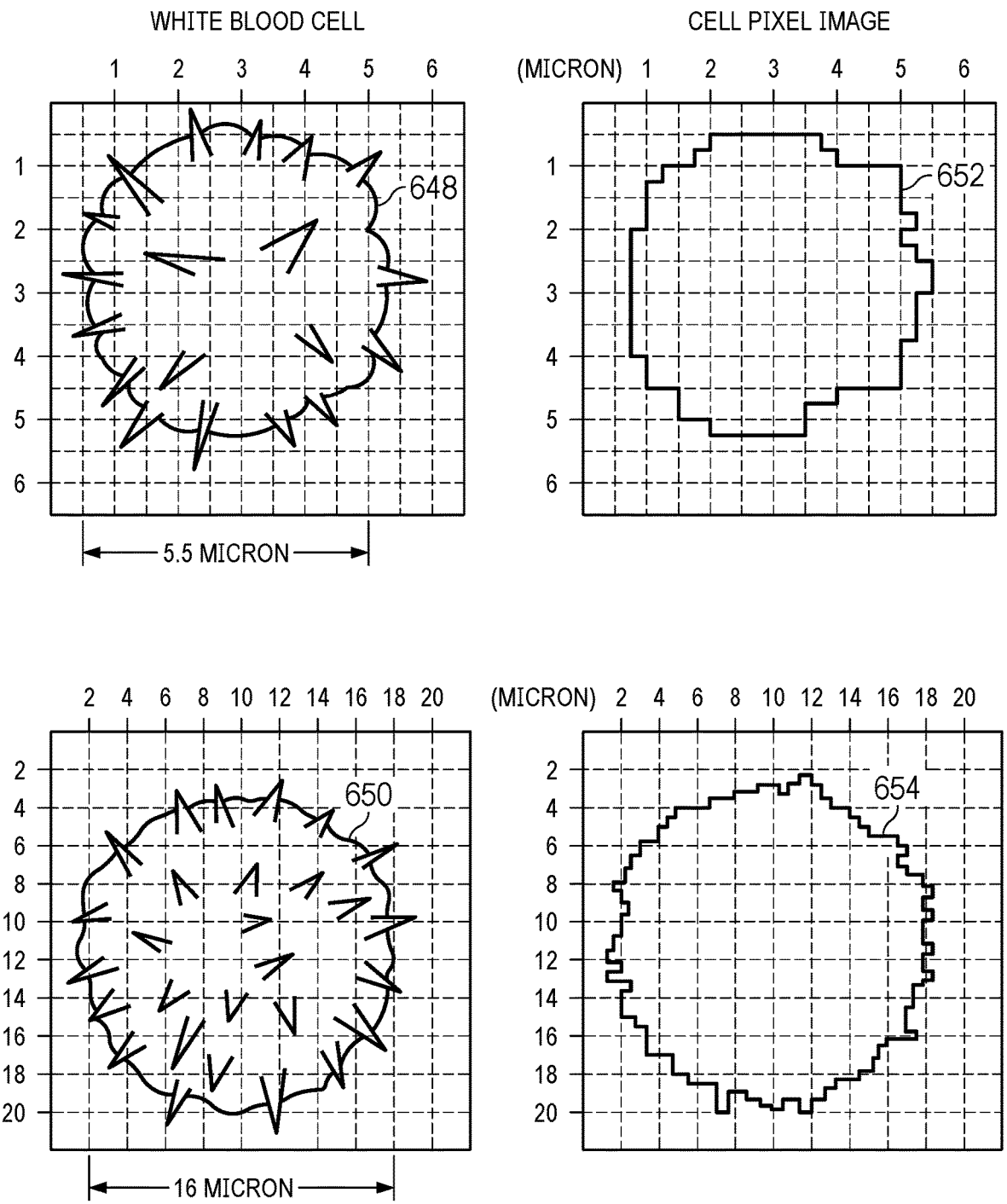
FIG. 36 is a set of white blood cell images for pattern recognition.

FIG. 36 shows a white blood cell 648 having a relatively large size and a white blood cell 650 having a smaller size. These cells are essentially spherical so appear approximately the same at all rotation angles. Cell 648 can produce a shadow image 652 and cell 650 can produce a shadow image 654. Again, these images 652 and 654 can be included in the cell library as images to ignore.

Figure 37:
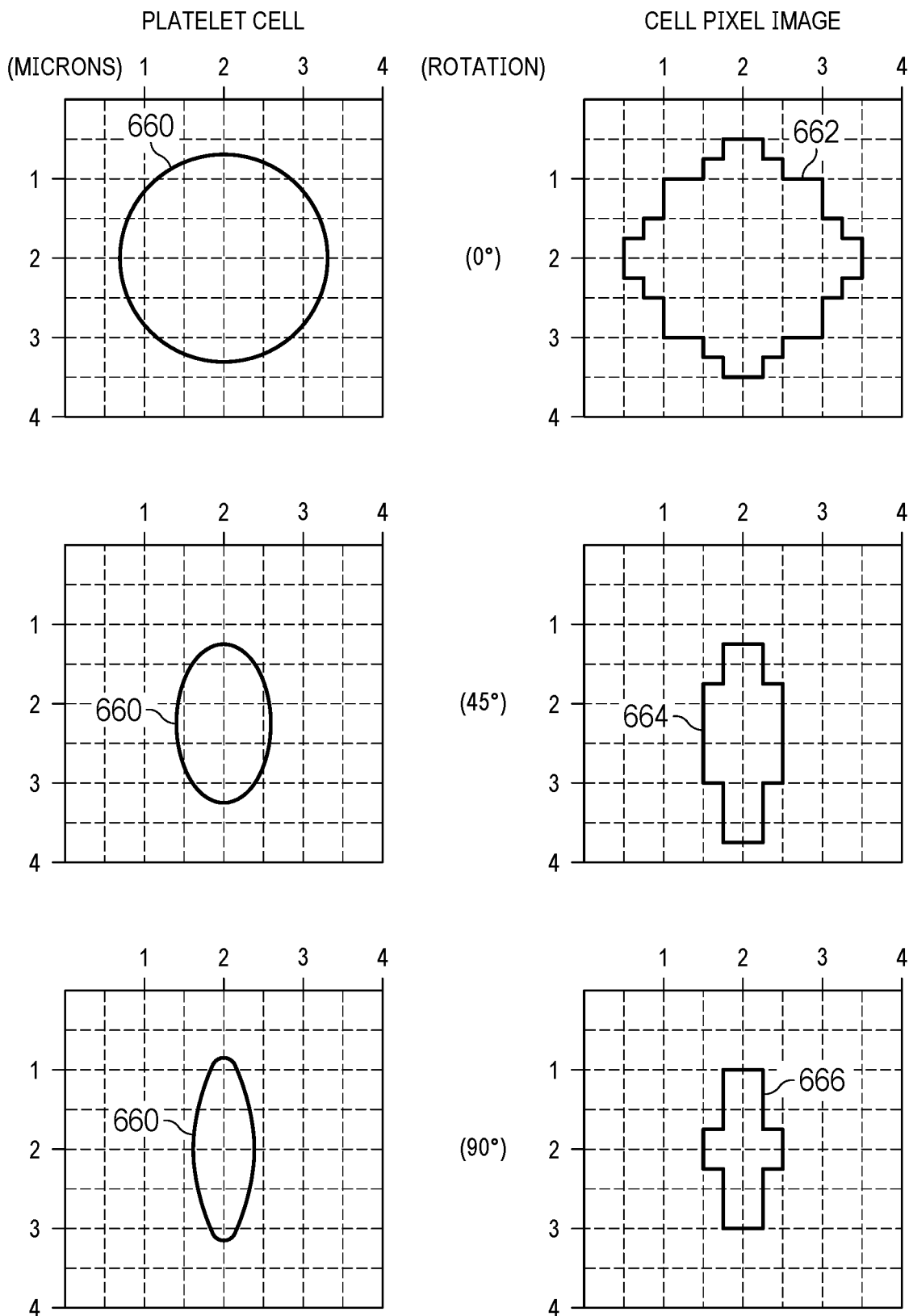
FIG. 37 is a set of platelet cell images for pattern recognition.

A blood platelet cell 660 is shown in FIG. 37. A platelet is a biconvex discoid (lens-shaped) structure, 2-3 micron in greatest diameter. This shape is thin at the edge and thickest in the center. At a rotation of 0 degrees, a cell 660 can produce a shadow image 662, at a rotation of 45 degrees a shadow image 664 and at 90 degrees, a shadow image 666. As with the other normal blood cells, these images are used as recognition of cells to ignore in the image recognition processing operation.

Each of the cells in FIGS. 35, 36 and 37 are shown, for illustration, at a limited number of rotation angles, but the reference library can contain images representing a finer degree of rotation, for example, every 5 degrees of rotation.

The operation of the present disclosure, in a summary description, includes initially determining the static position of pathogen cells in channels in the cassette chamber. Next, the pump and a travel time timer are started simultaneously. The pump operation causes the pathogen cells to move from the initial location toward the processing zone of the chamber. When the travel time expires for a located cell, that pathogen cell is then positioned in the venting region of the processing zone, the region having valves in the channel. When the travel time expires, the chamber driver generates voltage waveforms that are applied to the valve assemblies in the processing zone to activate the corresponding valves. One valve closes to block fluid flow in the channel, and a second valve is opened in a vent line from the channel such that a flow segment of blood (a slug) is driven through a vent line to the sump. This slug of blood includes the previously located pathogen cell. When the vent valve is opened, a small quantity of fluid is vented. A method of determining the travel time between the identification zone where a cell is located and the processing zone where the cell is vented is described in reference to FIGS. 38 and 39 and a logical flow diagram for this process is shown in FIG. 40.

Figure 38:
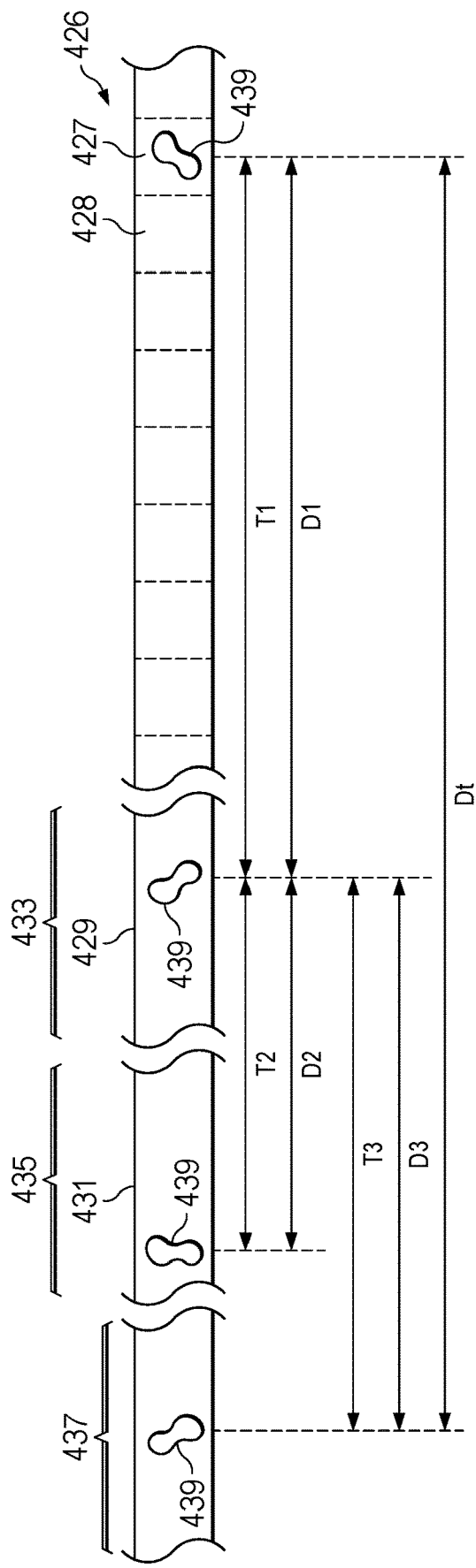
FIG. 38 is an illustration of blood flow in chamber channels for cell travel time calibration.
Figure 39:
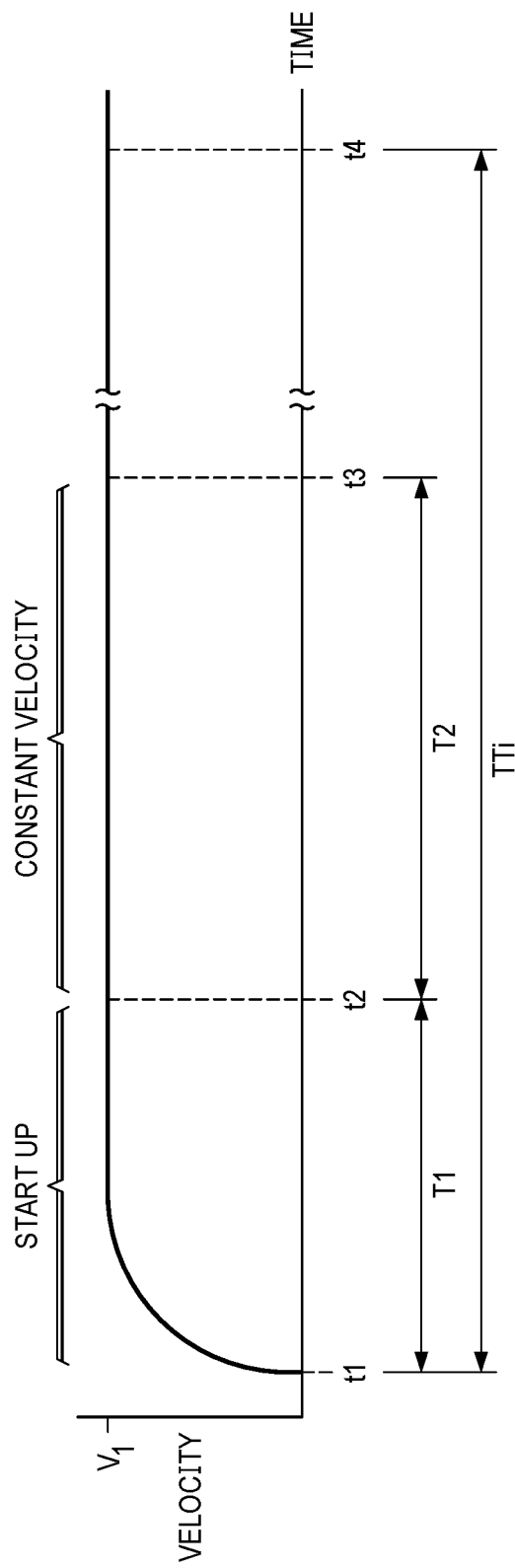
FIG. 39 is a travel time versus fluid velocity chart for cell travel time calibration.

Determination of travel times from specific channel zones to vent locations is shown in FIGS. 38 and 39. A channel 426 is representative of each of the channels shown in the chamber in FIG. 15. The channel 426 is divided into a plurality of sequential and contiguous channel zones, including exemplary channel zones 427, 428, 429 and 431. As an example, the channel 426 can be 8 microns wide and each zone is 6 microns long. The channel zones do not have any physical structure marking the position of each zone, but are defined by longitudinal position. If, for example, a channel is 2 centimeters long, it will have approximately 3333 channel zones. The channel 426 further includes arbitrarily defined sets of channel zones identified as a first window 433 of zones and a second window 435 of zones.

An approximation of the flow rate of blood through the channels in the chambers of the cassette 58 can be calculated using the flow rate of the pump 62 and the geometry of the flow lines and chambers of the cassette 58. The channel zone 427 is selected to be adjacent the input of the chamber. The location of the first window 433 is determined by use of the calculated approximate fluid flow rate of blood in a chamber and is sufficiently wide to accommodate the possible error in that flow rate calculation. The second window 435 is set downstream at a predetermined distance from the first window 433. A processing zone 437 in channel 426 corresponds to the processing zone 250 in FIG. 15. The flow rate calibration process described in FIGS. 38 and 39 more accurately establishes the total travel time from each of the channel zones, where a pathogen cell is initially located, to the valve opening in the processing zone, as compared to a flow rate determined by pump rate, tubing size and cassette geometry. The processing zone is the region of the channel at a channel opening, such as channel 277, to a valve assembly 287. See FIG. 16.

Referring to FIG. 39, there is shown a chart of flow rate of fluid versus time. The pump starts at time $t_1$ where the fluid velocity is zero. After the pump starts, the fluid velocity increases until it reaches a constant velocity. This is shown as velocity v₁. Depending on physical configuration, the time to reach constant velocity could be, for example, approximately 0.01 to 0.02 seconds. A time T1 is selected which is larger than the time for the fluid to reach constant velocity. A time T2 is selected which, when added to time T1, is the approximate travel time from the zone 427 to within the second window 435. The total travel time, from zone 427, to the center of the processing zone 437 is TTi, the "i" representing each zone.

The calibration process, shown in FIGS. 38 and 39, is described in detail in the logic diagram in FIG. 40. In summary, the process begins with pumping fluid into the chambers of a cassette and then stopping the pump. The light sensor below a chamber is activated and the light source is turned on the illuminate the chambers. Pathogen cells in the channels of the chamber create shadow images in the pixels of the light sensor. The data from the light sensor is stored in a corresponding memory. See. FIG. 24. The pixel image data is evaluated by a corresponding processor using pattern recognition with a reference library to identify and locate pathogen cells, such as cell 439 in channel zone 427 (see FIG. 38). The pump is activated and when the cell 439 is in the first window 433, the light sensor is reset and the light source is activated for a short flash, for example a millisecond or less, and the shadow image is created in the corresponding light sensor. The pixel data is processed by the corresponding chamber processor to identify and locate the cell 439, which as shown in this example, is located in channel zone 429. The locations of zones 427 and 429 define a distance D1. The fluid is moving at the constant velocity when the cell is imaged at zone 429, but the light flash is of sufficiently short duration, as compared to the flow rate, such that there is a clear image of the cell. This is essentially a "stop image" shot. The fluid continues to move until the pathogen cell is in the second window 435 where another flash shot image is taken as just described. The cell 429 is then determined to be in channel zone 431 in window 435.

Further referring to FIGS. 38 and 39, the distance between zones 429 and 431 is a known design parameter. T1 and T2 and distance Dt (for each channel zone) are selected in advance. T1 is selected to be less than the smallest total travel time. T3 (FIG. 38) is the flow time from the end of time T1 to the cell 439 arrival at the center of processing zone 437, the opening to the corresponding vent valve. D3 is the distance from zone 429 to the center of zone 437. The total travel time from an initial channel zone to the center of the processing zone is TTi. The constant velocity fluid flow rate (Vcv) between zones 429 and 431 is determined by the equation: Vcv=D2/T2. Therefore, the total travel time (TTi) from any channel zone to the center of the processing zone 437 is: TTi=T1+T3; T3=D3/Vcv, and therefore:

$$TTi=T1+(Dt-D1)(T2/D2).$$

Thus, after the calibration process described above has been performed for a channel in a chamber, the total travel time TTi can be calculated for each channel zone (i) in the identification field of the chamber. The distance Dt is different for each channel zone in a single channel. It is a cassette design parameter. Further, the same calibration process is performed for all of the channels in all of the chambers. A calibration table is prepared for each chamber that provides the travel time from each channel zone to the center of the corresponding processing zone. In operation, after a pathogen cell is identified in the detection zone and located in a specific channel zone, the pump is started and the pathogen cell moves toward the processing zone and when the total travel time, for that specific channel zone, expires, the pathogen cell is located in the processing zone. At that time, a voltage is applied to a first valve assembly in the processing zone to block the flow in the channel and to open a second valve to vent the pathogen cell as it passes through the processing zone. A limited volume of fluid surrounding the pathogen cell is also vented. In this process, the fluid flow is continuous after the pathogen cell has been initially identified and located. After the blood in the chamber has been replaced, the pump is stopped and the process is repeated.

Figure 40B:
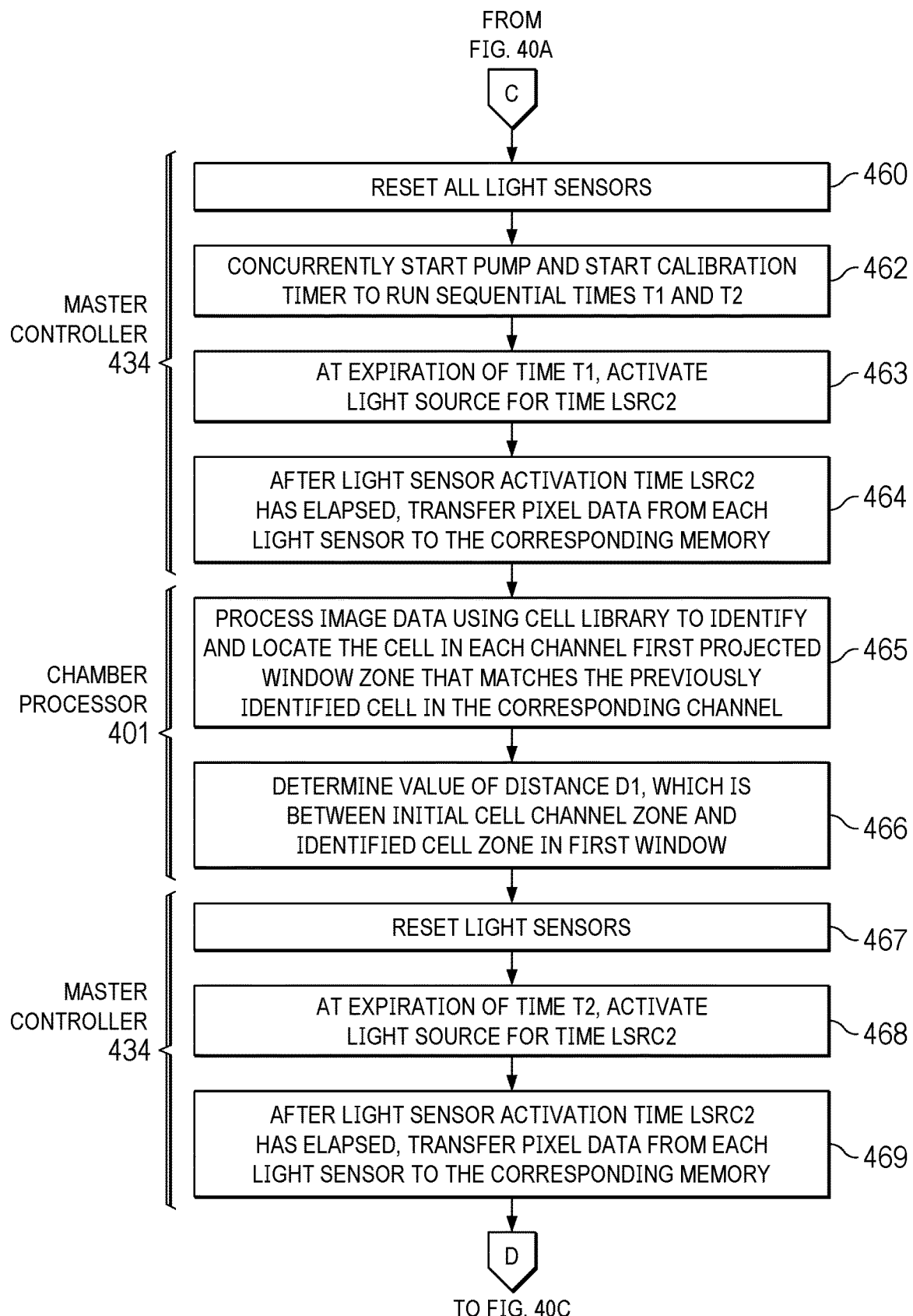
Figure 40C:
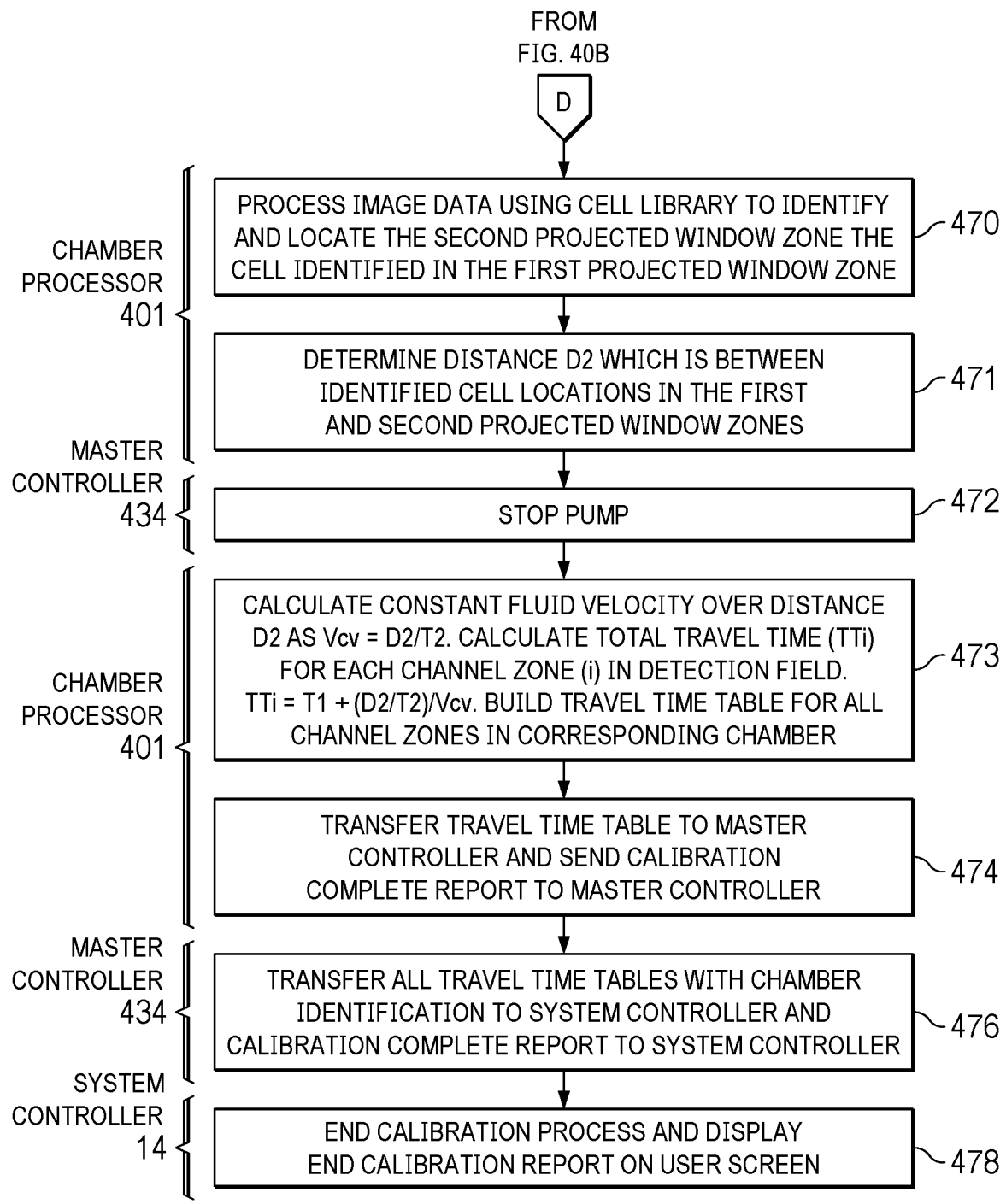

A logic flow description of the calibration process is shown in FIGS. 40A, 40B, and 40C. The calibration process is begun at step 446 at the system controller 14. The calibration parameters and data are the pump drive time to fill the chambers, for example 15 seconds, first and second light source activation times LSRC1 and LSRC2. Values of these times can be, for example, respectively 1 second and 1-5 milliseconds. The cell library is the collection of pathogen images described above. The estimated travel times can be, for example T1=1-2 seconds and T2=4-10 seconds. The start calibration command and the calibration parameters are downloaded to the master controller 434 from the system controller 14 in step 448.

Continuing reference to FIG. 40, in step 450, the master controller 434 starts the pump 62, runs the pump for the fill time and then stops the pump. Next, in step 452, the master controller 434 resets all of the light sensors so that they are prepared to receive light from the light source 54. In step 454, after the light sensors are reset, the master controller 434 activates the light source 54 for the time period LSRC1 and the light sensors receive light after it has passed through the chambers and shadow images of cells in the chambers are created in the pixel data in the light sensors. In step 456, after expiration of the time period LSRC1, the master controller 434 transfers the image data from the light sensors to the corresponding memories. See FIG. 24. In step 457, the chamber processor, for each chamber, processes the image data by performing pattern recognition with the cell library to identify pathogen cells in the channel zones. In step 458, each chamber processor selects one located pathogen cell for the calibration process. The specific location zone for this selected cell is identified. See FIG. 38.

In step 460, the master controller 434 resets all of the light sensors. See zone 427 in FIG. 38. Next, in step 462, the master controller concurrently starts the pump 62 and a calibration timer to run sequential times T1 and T2. At step 463, upon expiration of time T1, the light source 54 is activated for time period LSRC2. This takes a "stop action" image of cells in the channels in the first window 433. The fluid flow rate is slow in comparison to the on time of the light source so that a clear image is produced without stopping the fluid flow. At step 464, after the time LSRC2 has ended, the master controller 434 transfers the pixel data from each light sensor to the corresponding memory. In step 465, the chamber processors process the image data in the corresponding memories using the cell library and pattern recognition to identify and locate the cell previously identified in the channel at the initial channel zone. In step 466, the chamber processor determines the distance D1 which is between the initial channel zone location and the identified location in the first window 433.

In step 467, the master controller 434 resets all of the light sensors. Next, in step 468, when the time period T2 expires, the master controller activates the light source 54 for the time duration LSRC2. In step 469, when the time period T2 has expired, the master controller transfers the collected pixel data from each light sensor to the corresponding memory. In step 470, the chamber processors perform pattern recognition on the pixel data for pattern recognition and using the cell library as reference data, to locate the previously identified pathogen cell previously identified in the first window. Next, in step 471 the chamber processor determines the distance D2 which is the distance between the identified cell locations in the first and second windows. In step 472, the master controller 434 stops the pump.

Next, in step 473, the chamber processor calculates the fluid velocity between the two locations in the windows, using distance D2 and time T2. See FIG. 38. With this data the chamber processer determines the total travel time TTi for each channel zone (i) to the center of the processing zone. The travel times are determined for all channels in each chamber. In step 474, the chamber processors transfer the total travel time table of values for each chamber to the master controller 434. In step 476, the master controller transfers all of the travel time tables for all of the chambers to the system controller 14 and reports completion of the calibration process. In step 478, the system controller 14 displays an end of calibration report on its display screen and ends the calibration process.

By calibrating the travel time of each initially detected pathogen cell to the center of the processing zone, the duration of the valve open time can be limited so that the minimum volume of fluid is vented with the pathogen cell. If the predicted total travel time number were to be less accurate, the vented fluid volume in the processing zone would need to be larger to assure that the pathogen cell is in the processing zone when the vent valve is open. Alternatively, the travel times can be calculated by use of ump flow rate and the parameters of the flow tubes and chambers.

Figure 41B:
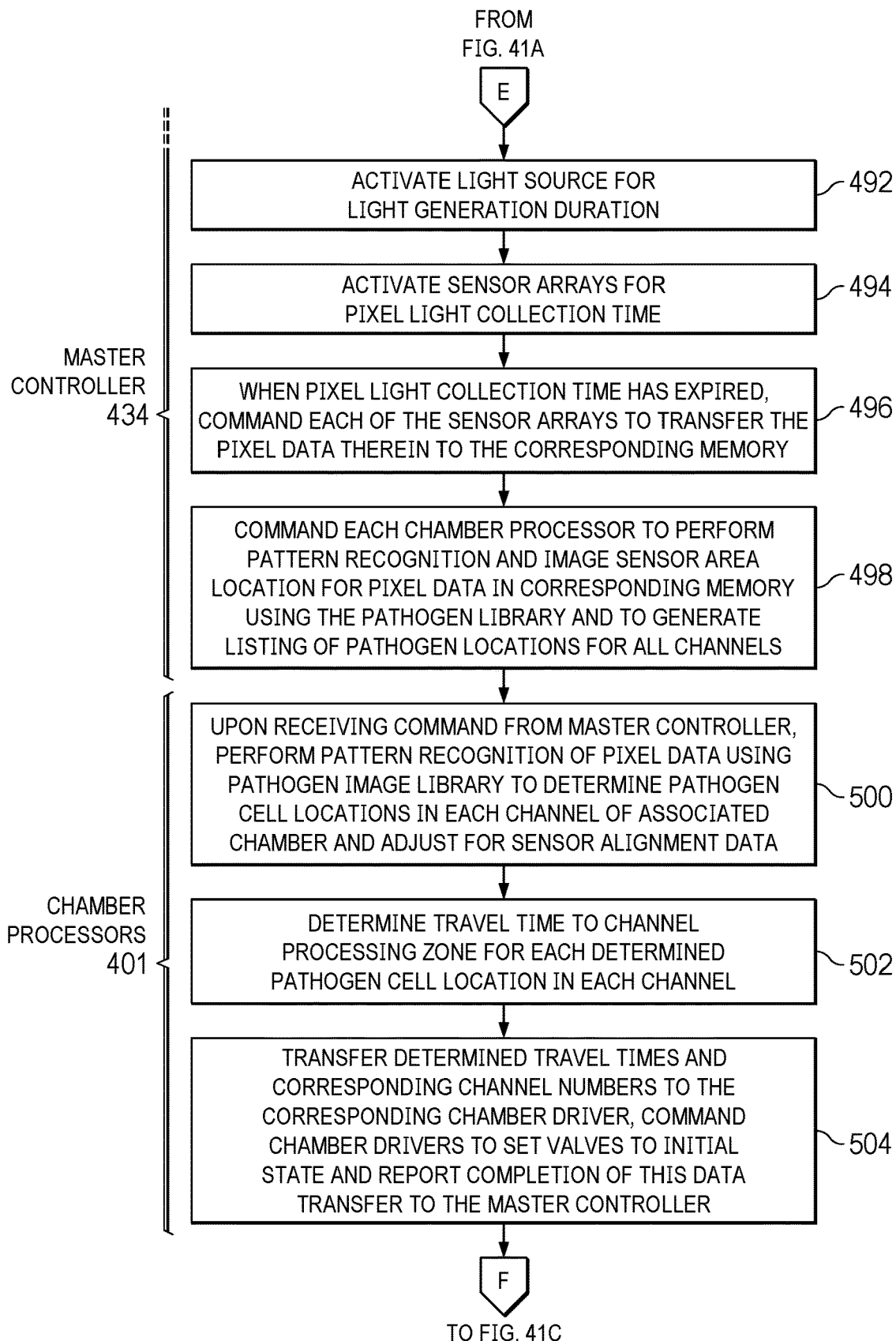
FIGS. 41A and 41B are a logic flow diagram illustrating an operational process to identify and locate pathogen cells and to move the identified cells to a processing zone in a chamber for venting to a sump.
Figure 41C:
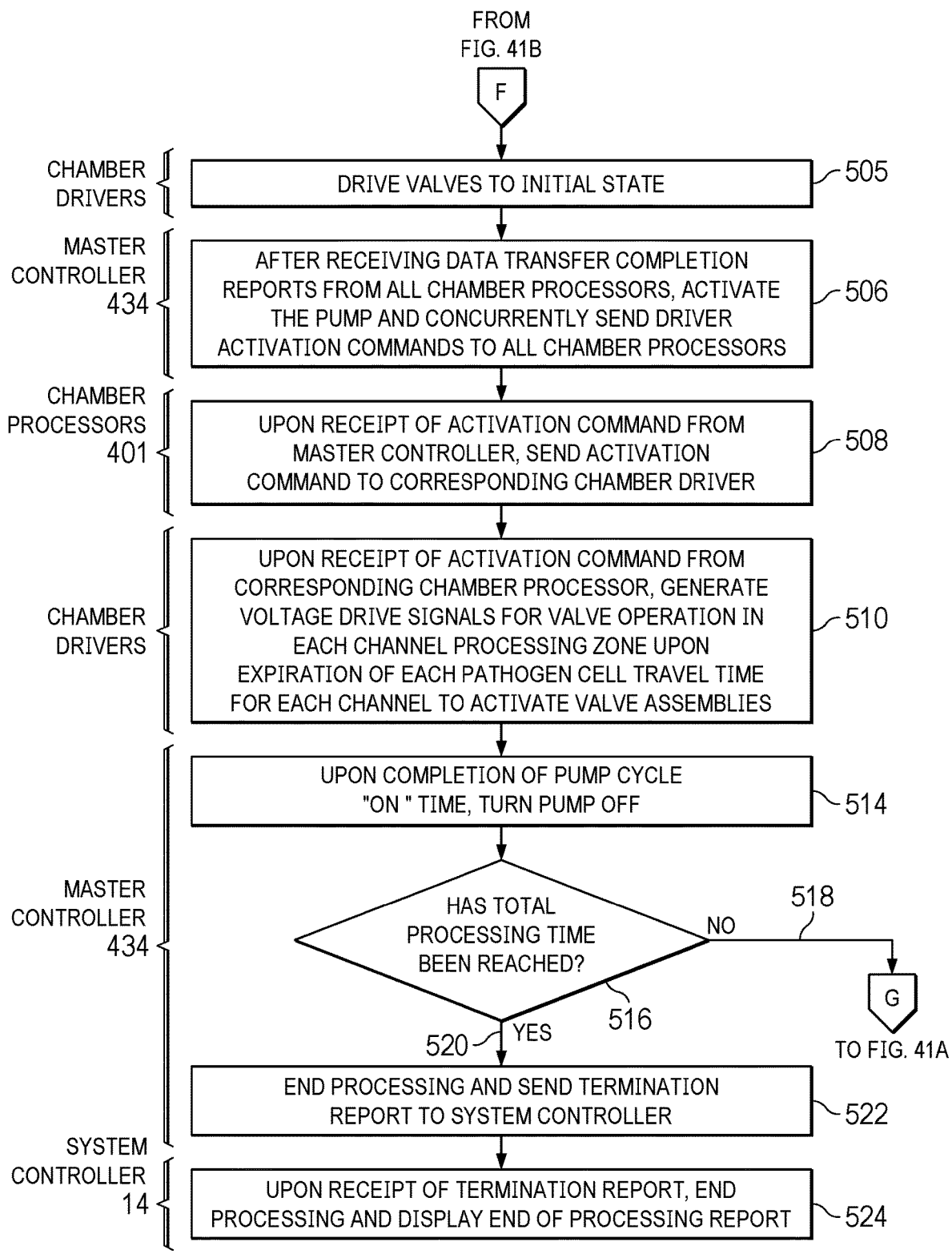

An operation process for an embodiment of the present invention is shown by the logic flow in FIGS. 41A, 41B and 41C. This process utilizes apparatus shown and described in the prior text and figures. The process begins with a start command, for example, from an operator, at the system controller 14 in step 480. The system controller 14 downloads data and processing parameters, step 482, and a start command is sent to the master controller 434. The processing data and parameters include:

1. Pathogen image cell library.
2. Initial pump flow time and pump cycle on and off times. This can be, for an example, an initial flow time of 20 seconds to completely fill all of the chambers. After the start, a flow and processing time of 10 seconds with a stop time of 2 seconds for identification of pathogen cells. The 2 second stop with 10 second flow procedure is repeated until the processing is completed.
3. A light generation time, for example, in a range of 20 to 100 milliseconds.
4. A light sensor collection time of, for example, within a range of 5 to 50 milliseconds.
5. Voltage waveforms and timing for application to the processing zone valve assemblies.
6. Alignment data for each sensor array.
7. Travel Time Table for each channel of each chamber.
8. Total processing time, for example, in the range of 6-24 hours.

In step 484, the master controller 434 sends certain data and processing parameters to the chamber processors. This includes the pathogen image library, the voltage waveforms and timing for the valve assemblies in the processing zone, the alignment data for sensor arrays and the total travel time tables for each chamber. In step 486 the voltage waveforms and travel time tables are transferred from the chamber processors to the chamber drivers for each chamber.

In step 488, the master controller 434 runs the pump for the initial pump flow time to fill the chambers and then stops the pump. The master controller 434 also starts a total processing time timer. In step 490, the master controller resets all of the light sensor arrays so they are prepared to receive light. In step 492, the master controller 434 activates the light source 54 for the light generation time. Next, in step 494, the light sensors are activated to collect light for the pixel light collection time. In step 496 the collected pixel light data is transferred from the sensor arrays to a corresponding memory. In step 498, the master controller 434 commands each chamber processor to perform pattern recognition on the stored pixel data using the pathogen cell library and to locate each identified pathogen cell in each chamber of the corresponding chamber. In step 500, each chamber processor performs the pattern recognition and generates a listing of the pathogen cell locations in each channel of the corresponding chamber. Each identified pathogen cell is in a channel zone, see FIG. 38, for example zone 428. The chamber processor also adjusts for any misalignment between cassette and sensor array with the alignment data. In step 502 each chamber processor, by use of the downloaded travel time table, determines the total travel time for each identified pathogen cell from its identified channel zone location to the vent line at the center of the processing zone.

Figure 42:
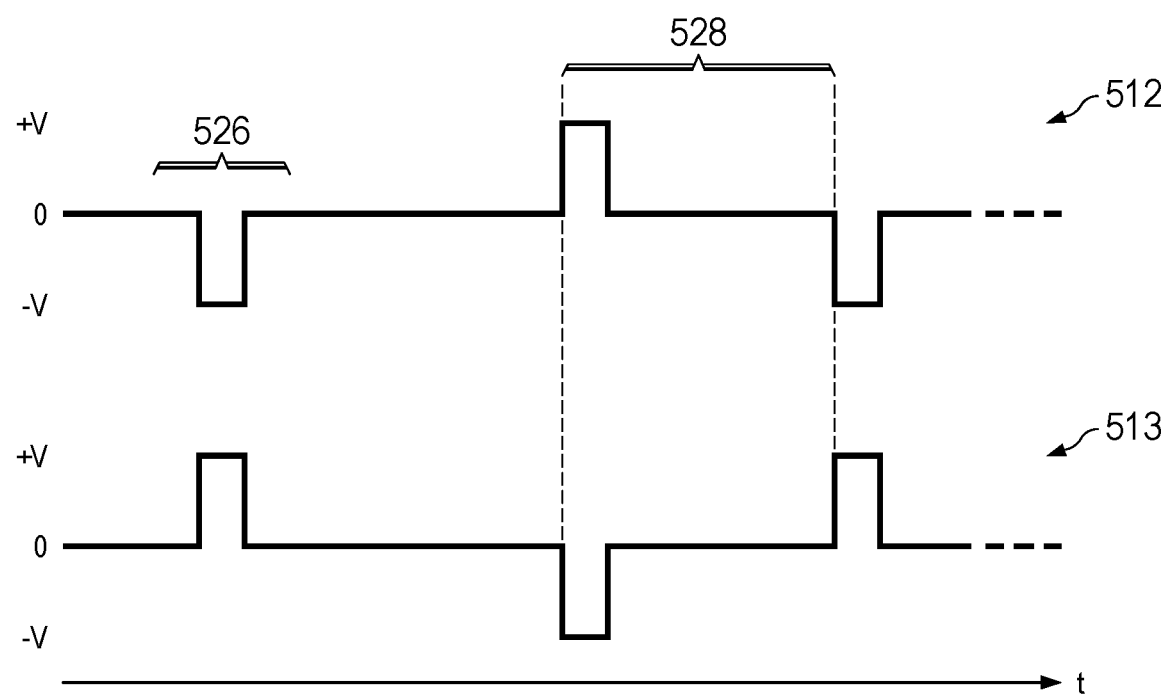
FIG. 42 is a diagram of electrical waveforms applied to valves in the processing zone of a chamber for selectively opening and closing the valves to vent identified pathogen cells to a sump.

Further referring to FIG. 41C, in step 504 the determined travel times for each identified pathogen cell and the corresponding channel are transferred to the corresponding chamber drivers. The chamber drivers are also commanded to set the valves to the initial state 526 as shown in FIG. 42. Further referring to FIG. 42, signal 512 is applied, selectively, by the chamber driver 318 to each of the channel valves 275 and signal 513 is applied, selectively, to the vent valves 276.

Further in FIG. 41B, in step 504 the chamber processors report the completion of the data transfer to the master controller 434. In step 505 of FIG. 41C, the chamber drivers apply the initial state pulses 526 (FIG. 42) to all of the channel valves and vent valves such that the channel valves allow fluid to flow in the channels and the vent valves block fluid flow in all of the vent lines.

In FIG. 42, the voltage −V causes the valve element to retract, the voltage +V causes the valve element to extend.

The data transfer and command in step 504 is done via the optical data link from the chamber processor to the chamber driver, see FIG. 24, light transmitter 409 and FIG. 21, light receiver 348. In step 506 of FIG. 41C, the master controller 434 receives the data transfer completion reports for all chamber processors and then activates the pump 62 and sends chamber driver activation commands to all of the chamber processors.

In step 508, the chamber processors send activation commands to the corresponding chamber drivers via the optical link. In step 510, in response to the activation command, each chamber driver starts the timing for the total travel times for the identified pathogen cells in each channel of each holding chamber. When a total travel time is completed for a channel, the corresponding chamber driver generates voltage signals which are applied to the control lines in that channel in the processing zone, for example, control lines 284 shown in FIG. 17. In FIG. 42 there are shown waveforms 512 and 513. These waveforms are shown as a function of time "t" along the horizontal scale. The peak positive value is +V, which can be, for example, 10 volts. These waveforms are applied to the lines 284 shown in FIG. 17. The group of lines 284 have a single wire pair going from the driver 318 to each of the valve assemblies. The pair of lines provide a differential voltage. Further referring to FIG. 42, signal 512 is applied selectively to the channel valves 275 and signal 513 is selectively applied to the vent valves 276.

In FIG. 42, the initial state 526 has a negative pulse for signal 513 which retracts the valve element for each of the channel valves to allow fluid to flow through the channels. For signal 513 in the initial state 526, the positive pulse causes each of the valve elements of the vent valves 276 to extend and thereby close the vent lines. A vent cycle 528 is initiated when each total travel time for a located pathogen cell has expired. The vent cycle for signal 512 (channel valve) has a positive pulse that extends the valve element to block the fluid flow through the corresponding channel Signal 513 has a negative pulse which causes the corresponding vent valve to retract and allow the fluid to move up the vent line from the flow channel and through the vent line to the sump 25. At the end of the vent cycle 528, the negative pulse in signal 512 causes the channel valve element to retract and allow fluid flow through the channel and concurrently the positive pulse in signal 513 causes the vent valve element to extend and block fluid flow through the vent line. The vent cycle 528 duration is the parameter "vent time."

Continuing reference to FIG. 41C, at step 514, the master controller 434 turns the pump 62 off upon expiration of the pump cycle time. This time is set to be long enough for all of the pathogen cells to flow from the most distant portion of the detection zone to the processing zone. That is, longer than the longest total travel time. When the pump 62 has been turned off, the blood previously in the chambers has been removed and replaced with a new volume of blood for processing. Following step 514 the master controller performs the question step 516 to determine if the total processing time has been reached. If the answer to this question is "NO", the exit 518 is taken and operations are transferred to step 490 to repeat the overall processing operation. If the answer to the step 516 question is "YES", exit 520 is taken to step 522. If this exit is taken, the total processing time has elapsed. In step 522, the master controller 434 terminates the processing operation and sends a report thereof to the system controller 14. In step 524 the system controller 14 ends the processing operation and sends a report thereof to its display terminal.

One embodiment described above has 30 chambers in a single cassette with a sensor, a chamber processor and memory for each chamber. However, embodiments can be implemented having different configurations which operate as described above. Further, the embodiments can be scaled by the number of chambers and/or flow rate through a chamber and/or data processing speed to provide a desired overall flow rate for blood processing. Non-limiting example embodiments are as follows:
1. 10 chambers each 2.0 cm×2.0 cm, each chamber having a corresponding light sensor with a single processor and memory serving all 10 chambers.
2. 10 chambers each 4.0 cm×4.0 cm, each chamber having a corresponding light sensor, processor and memory.
3. 30 chambers 2.0 cm×2.0 cm, each chamber having a corresponding light sensor, and a single processor and memory serving all 30 chambers.
4. 30 chambers divided into a separate 15 chamber Group A and 15 chamber Group B with a sensor for each chamber and a single processor and single memory for each group.
5. 40 chambers each 2.0 cm×2.0 cm and each chamber having a corresponding light sensor, and a processor and memory for each set of 10 chambers.
6. 100 chambers 2.0 cm×2.0 cm, each chamber having a corresponding light sensor, processor and memory.
7. 100 chambers 2.0 cm×2.0 cm, each chamber having a corresponding light sensor and having one memory and one processor for each 10 chambers.

Although several embodiments of the invention have been illustrated in the accompanying drawings and described in the foregoing Detailed Description, it will be understood that the invention is not limited to the embodiments disclosed but is capable of numerous rearrangements, modifications and substitutions without departing from the scope of the invention.

What is claimed is:

1. A cassette for processing of blood, comprising:
a chamber within said cassette, said chamber having opposed parallel walls, said chamber having an input port and an output port,
said cassette having an input port for receiving said blood, an output port for exhausting said blood from said cassette and a fluid vent port,
a distribution line coupled between said cassette input port and said chamber input port and a collection line coupled between said chamber output port and said cassette output port,
said chamber having a plurality of parallel flow channels between said chamber input port and said chamber output port,
a plurality of channel vent lines coupled respectively to said plurality of said flow channels,
a plurality of vent valves connected respectively to said plurality of channel vent lines, each said vent valve for selectively controlling fluid flow through the corresponding channel vent line, and
said cassette including a cassette vent line having a plurality of inputs coupled respectively to said channel vent lines and said cassette vent line having an output coupled to said cassette fluid vent port.

2. A cassette as recited in claim 1 including a plurality of flow channel valves respectively mounted proximate said plurality of flow channels downstream from a coupling joint of the corresponding flow line with the corresponding channel vent line, each channel valve for selectively controlling the fluid flow through the corresponding flow channel.

3. A cassette as recited in claim 2 including an electronic driver for selectively activating said channel vent valves and said flow channel valves.

4. A cassette as recited in claim 1 wherein said cassette comprises first, second and third layers of plastic bonded together, said first layer shaped to form said cassette vent line, said second layer shaped to form (a) a first one of said opposed parallel walls of said chamber and (b) said channel vent lines, and said third layer forming a second of said opposed parallel walls of said chamber.

5. A cassette as recited in claim 1 wherein said cassette comprises a plastic material which includes a blood anti-thrombogenic component.

6. A cassette as recited in claim 1 wherein said channel vent lines are positioned perpendicular to said flow channels.

7. A cassette as recited in claim 2 wherein said vent valves, said flow channel valves and an electronic driver coupled to said vent valves and said flow channel valves are mounted in a valve block assembly which valve block assembly is mounted to said cassette.

8. A cassette for processing of blood, comprising:
a plurality of chambers in said cassette, each said chamber having parallel transparent walls and each said chamber having an input port and an output port,
said cassette having an input port for receiving said blood, an output port for exhausting said blood from said cassette and a fluid vent port,
a distribution manifold coupled between said cassette input port and said chamber input ports and a collection manifold coupled between said chamber output ports and said cassette output port,
each said chamber having a plurality of parallel flow channels between said chamber input port and said chamber output port,
a plurality of flow channel valves corresponding respectively to said plurality of said flow channels and each said flow channel valve positioned to control the fluid flow through the corresponding flow channel,
a plurality of channel vent lines coupled respectively to said plurality of said flow channels,
a plurality of vent valves corresponding respectively to said plurality of channel vent lines, each said vent valve positioned to control the fluid flow through the corresponding channel vent line,
an electronic driver coupled to each of said flow channel valves and said vent valves for individually operating said flow channel valves and said vent valves,
said cassette including an exhaust vent line having a plurality of inputs connected respectively to said channel vent lines on the opposite side of the corresponding vent valve from the corresponding flow channel, and
said exhaust vent line having an output coupled to said cassette fluid vent port.

9. A cassette as recited in claim 8 wherein said plurality of flow channels are formed by a plurality of ridges extending between each said chamber input port and output port and said opposing walls of each said chamber.

10. A cassette as recited in claim 8 wherein said cassette comprises first, second and third layers of plastic bonded together, said first layer shaped to form said exhaust vent lines, said second layer shaped to form a first of said opposed walls of each said chamber and said third layer forming a second of said opposed walls of each of said chambers.

11. A cassette as recited in claim 8 wherein said vent valves, said flow channel valves and said electronic driver are mounted in a valve block assembly which valve block assembly is mounted to said cassette.

12. A cassette as recited in claim 8 wherein said cassette comprises a plastic material which includes a blood anti-thrombogenic component.

13. A cassette as recited in claim 8 including a light receiver circuit mounted to said cassette and electrically coupled to said driver, said light receiver circuit for generating electrical power which is provided to said driver.

14. A cassette as recited in claim 8 wherein the interior surfaces of said opposing walls of said chambers are separated by a distance of no more than 10 microns.

15. A cassette for processing of blood, comprising:
a chamber within said cassette, said chamber having opposed parallel walls and said chamber having an input port and an output port,
said cassette having an input port for receiving said blood, said cassette input port coupled to said chamber input port,
said cassette having an output port coupled to said chamber output port, said cassette output port coupled to said chamber output port,
said cassette having a fluid vent port,
said chamber having therein a plurality of ridges extending between said chamber input port and said chamber output port to form with said walls a plurality of parallel flow channels through said chamber,
a plurality of channel vent lines respectively coupled to said plurality of said flow channels,
a plurality of vent valves respectively proximate said plurality of channel vent lines, each said vent valve for selectively opening and closing the corresponding channel vent line to selectively provide fluid flow from the corresponding flow channel through the corresponding channel vent line, and
said cassette including an exhaust vent line having a plurality of inputs connected respectively to said channel vent lines on the opposite side of the corresponding vent valve from the corresponding flow channel, and
said exhaust vent line having an output coupled to said cassette fluid vent port.

16. A cassette as recited in claim 15 including an electronic driver coupled to each of said flow channel valves and said vent valves for individually operating said flow channel valves and said vent valves.

17. A cassette as recited in claim 15 including a plurality of said chambers and wherein said chambers are coplanar.

18. A cassette as recited in claim 15 wherein said channel vent lines are perpendicular to said flow channels.

19. A cassette as recited in claim 15 wherein said exhaust vent line is perpendicular to said channel vent lines.

20. A cassette as recited in claim 15 wherein said cassette comprises a plastic material which includes a blood anti-thrombogenic component.

* * * * *